(12) United States Patent
Maglia et al.

(10) Patent No.: US 9,562,887 B2
(45) Date of Patent: Feb. 7, 2017

(54) METHODS OF ENHANCING TRANSLOCATION OF CHARGED ANALYTES THROUGH TRANSMEMBRANE PROTEIN PORES

(71) Applicant: Isis Innovation Limited, Oxford (GB)

(72) Inventors: Giovanni Maglia, Leuven (BE); John Hagan Pryce Bayley, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/334,285

(22) Filed: Jul. 17, 2014

(65) Prior Publication Data

US 2015/0008126 A1    Jan. 8, 2015

Related U.S. Application Data

(62) Division of application No. 13/129,278, filed as application No. PCT/GB2009/002666 on Nov. 13, 2009, now abandoned.

(30) Foreign Application Priority Data

Nov. 14, 2008    (GB) .................................. 0820927.2

(51) Int. Cl.
| G01N 33/487 | (2006.01) |
|---|---|
| C07K 14/245 | (2006.01) |
| C12Q 1/68 | (2006.01) |
| G01N 33/68 | (2006.01) |
| G01N 27/447 | (2006.01) |

(52) U.S. Cl.
CPC ........ *G01N 33/48721* (2013.01); *C07K 14/245* (2013.01); *C12Q 1/6869* (2013.01); *G01N 27/447* (2013.01); *G01N 33/6872* (2013.01); *G01N 2333/705* (2013.01)

(58) Field of Classification Search
CPC ..................... G01N 33/48721; G01N 33/6872; G01N 2333/705; G01N 27/447; C07K 14/245; C12Q 1/6869; C12Q 2565/631
See application file for complete search history.

(56) References Cited

U.S. PATENT DOCUMENTS

| 5,561,043 | A | 10/1996 | Cantor et al. |
|---|---|---|---|
| 5,777,078 | A | 7/1998 | Bayley et al. |
| 5,795,782 | A | 8/1998 | Church et al. |
| 5,817,771 | A | 10/1998 | Bayley et al. |
| 5,985,834 | A | 11/1999 | Engel et al. |
| 6,015,714 | A | 1/2000 | Baldarelli et al. |
| 6,123,819 | A | 9/2000 | Peeters |
| 6,127,166 | A | 10/2000 | Bayley et al. |
| 6,251,610 | B1 | 6/2001 | Gupte et al. |
| 6,362,002 | B1 | 3/2002 | Denison et al. |
| 6,426,231 | B1 | 7/2002 | Bayley et al. |
| 6,451,563 | B1 | 9/2002 | Wittig et al. |
| 6,627,067 | B1 | 9/2003 | Branton et al. |
| 6,824,659 | B2 | 11/2004 | Bayley et al. |
| 6,863,833 | B1 | 3/2005 | Bloom et al. |
| 6,916,665 | B2 | 7/2005 | Bayley et al. |
| 6,927,070 | B1 | 8/2005 | Bayley et al. |
| 7,087,729 | B1 | 8/2006 | Prive |
| 7,238,485 | B2 | 7/2007 | Akeson et al. |
| 8,105,846 | B2 | 1/2012 | Bayley et al. |
| 8,673,550 | B2 | 3/2014 | Gundlach et al. |
| 8,785,211 | B2 | 7/2014 | Bayley et al. |
| 8,822,160 | B2 | 9/2014 | Bayley et al. |
| 9,222,082 | B2 | 12/2015 | Jayasinghe et al. |
| 2002/0028458 | A1 | 3/2002 | Lexow |
| 2002/0094526 | A1 | 7/2002 | Bayley et al. |
| 2003/0044816 | A1 | 3/2003 | Denison et al. |
| 2003/0087232 | A1 | 5/2003 | Christians et al. |
| 2003/0099951 | A1 | 5/2003 | Akeson et al. |
| 2003/0108902 | A1 | 6/2003 | Abarzua |
| 2003/0118595 | A1 | 6/2003 | Niemeyer et al. |
| 2003/0165936 | A1 | 9/2003 | Rabbani et al. |
| 2003/0166137 | A1 | 9/2003 | Zuker et al. |
| 2003/0211502 | A1 | 11/2003 | Sauer et al. |
| 2003/0215881 | A1 | 11/2003 | Bayley et al. |
| 2004/0214177 | A1 | 10/2004 | Bension |
| 2004/0229315 | A1 | 11/2004 | Lee et al. |
| 2005/0053961 | A1 | 3/2005 | Akeson et al. |
| 2005/0260655 | A1 | 11/2005 | Liu et al. |
| 2007/0015182 | A1 | 1/2007 | Abarzua |

(Continued)

FOREIGN PATENT DOCUMENTS

| GB | 2130219 | 5/1984 |
|---|---|---|
| GB | 2453377 | 4/2009 |

(Continued)

OTHER PUBLICATIONS

Henrickson, Sarah E. et al., "Driven DNA Transport into an Asymmetric Nanometer-Scale Pore," Physical Review Letters, vol. 85(14):3057-3060 (2000).

Holden, Matthew A. et al., "Direct Introduction of Single Protein Channels and Pores into Lipid Bilayers," J. Am. Chem. Soc., vol. 127:6502-6503 (2005).

Holden, Matthew A. et al., "Functional Bionetworks from Nanoliter Water Droplets," J. Am. Chem. Soc., vol. 129:8650-8655 (2007).

(Continued)

*Primary Examiner* — Ruixiang Li

(74) *Attorney, Agent, or Firm* — Nelson Mullins Riley & Scarborough LLP; Jane E. Remillard, Esq.; Adam J. Gastonguay

(57) ABSTRACT

The invention relates to enhancing translocation of a charged analyte through a transmembrane protein pore. Translocation is enhanced by increasing the net opposing charge of the barrel or channel and/or entrance of the pore. The invention also relates to pores enhanced in accordance with the invention.

4 Claims, 15 Drawing Sheets

(56) References Cited

U.S. PATENT DOCUMENTS

| | | |
|---|---|---|
| 2007/0122885 A1 | 5/2007 | Reeves et al. |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0256116 A1 | 10/2009 | Shumaker-Parry et al. |
| 2009/0298075 A1 | 12/2009 | Travers et al. |
| 2010/0221212 A1 | 9/2010 | Stagliano et al. |
| 2011/0019186 A1 | 1/2011 | Himmelhaus et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0055792 A1 | 3/2012 | Gundlach et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2013/0143802 A1 | 6/2013 | Chilkoti |
| 2013/0195908 A1 | 8/2013 | Leonetti et al. |
| 2014/0051069 A1 | 2/2014 | Jayasinghe et al. |
| 2014/0206842 A1 | 7/2014 | Majeed et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0175663 A1 | 6/2015 | Yokoi et al. |
| 2016/0076092 A1 | 3/2016 | Jayasinghe et al. |

FOREIGN PATENT DOCUMENTS

| | | |
|---|---|---|
| JP | 11-137260 | 5/1999 |
| WO | 99/05167 A1 | 2/1999 |
| WO | 00/28312 A1 | 5/2000 |
| WO | 01/40516 A2 | 6/2001 |
| WO | 01/42782 A1 | 6/2001 |
| WO | 01/59453 A2 | 8/2001 |
| WO | 02/42496 A2 | 5/2002 |
| WO | 03/012146 A1 | 2/2003 |
| WO | 03/095669 A1 | 11/2003 |
| WO | 2005/056750 A2 | 6/2005 |
| WO | 2006/020775 A2 | 2/2006 |
| WO | 2006/028508 A2 | 3/2006 |
| WO | 2006/100484 A2 | 9/2006 |
| WO | 2007/057668 A1 | 5/2007 |
| WO | 2007/075987 A2 | 7/2007 |
| WO | 2007/084103 A2 | 7/2007 |
| WO | 2008/045575 A2 | 4/2008 |
| WO | 2008/083554 A1 | 7/2008 |
| WO | 2008/102120 A1 | 8/2008 |
| WO | 2008/102121 A1 | 8/2008 |
| WO | 2008/124107 A1 | 10/2008 |
| WO | 2010/004265 A1 | 1/2010 |
| WO | 2010/034018 A2 | 3/2010 |

OTHER PUBLICATIONS

Hornblower, Breton et al., "Single-molecule analysis of DNA-protein complexes using nanopores," Nature Methods, vol. 4(4):315-317 (2007).

Howorka, S. et al., "Improved Protocol for High-Throughput Cysteine Scanning Mutagenesis," Biotechniques, vol. 25(5):764-766 (1998).

Howorka, Stefan et al., "DNA Duplex Formation of Individual DNA Strands within a Single Protein Pore," Biophysical Journal, vol. 82(1, pt. 2):508a, No. 2482-Plat (2002).

Howorka, Stefan et al., "Kinetics of duplex formation for individual DNA strands within a single protein nanopore," PNAS, vol. 98(23):12996-13001 (2001).

Howorka, Stefan et al., "Probing Distance and Electrical Potential within a Protein Pore with Tethered DNA," Biophysical Journal, vol. 83:3202-3210 (2002).

Howorka, Stefan et al., "Sequence-specific detection of individual DNA strands using engineered nanopores," Nature Biotechnology, vol. 19:636-639 (2001).

Hu, Tao et al., "Theory of DNA translocation through narrow ion channels and nanopores with charged walls," Physical Review E, vol. 78:032901, DOI: 10.11031PhysRevE.78.032901, 3 pages, (2008).

Hwang, William L. et al., "Electrical Behavior of Droplet Interface Bilayer Networks: Experimental Analysis and Modeling," J. Am. Chem. Soc., vol. 129:11854-11864 (2007).

Jayasinghe, Lakmal et al., "The leukocidin pore: Evidence for an octamer with four LukF subunits and four LukS subunits alternating around a central axis," Protein Science, vol. 14:2550-2561 (2005).

Jung, Yuni et al., "The Internal Cavity of the Staphylococcal alpha-Hemolysin Pore Accommodates ~175 Exogenous Amino Acid Residues," Biochemistry, vol. 44(25):8919-8929 (2005).

Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).

Kang, Xiao-feng et al., "Single Protein Pores Containing Molecular Adapters at High Temperatures," Angew. Chem. Int. Ed., vol. 44:1495-1499 (2005).

Kasianowicz, John J. et al., "Characterization of individual polynucleotide molecules using a membrane channel," Proc. Natl. Acad. Sci. USA, vol. 93:13770-13773 (1996).

Khulbe, Pramod K. et al., "DNA translocation through a-hemolysin nanopores with potential application to macromolecular data storage," Journal of Applied Physics, vol. 97(104317):1-7 (2005).

Kocalka, Petr et al., "Rapid and Efficient DNA Strand Cross-Linking by Click Chemistry," ChemBioChem, vol. 9:1280-1285 (2008).

Kolb, Hartmuth C. et al., "Click Chemistry: Diverse Chemical Function from a Few Good Reactions," Angew. Chem. Int. Ed., vol. 40:2004-2021 (2001).

Kovall, Rhett et al., "Toroidal Structure of Lambda-Exonuclease," Science, vol. 277:1824-1827 (1997).

Li, Jiali et al., "DNA molecules and configurations in a solid-state nanopore microscope," Nature, vol. 2:611-615 (2003).

Lovett, Susan T. et al., "Identification and purification of a single-stranded-DNA-specific exonuclease encoded by the recJ gene of *Escherichia coli*," Proc. Natl. Acad. Sci. USA, vol. 86:2627-2631 (1989).

Lovrinovic, Marina et al., "Rapid synthesis of DNA-cysteine conjugates for expressed protein ligation," Biochemical and Biophysical Research Communications, vol. 335:943-948 (2005).

Luo, Kaifu et al., "Influence of Polymer-Pore Interactions on Translocation," Physical Review Letters, vol. 99:148102, DOI: 10.1103/PhysRev Lett. 99.148102, 4 pages, (2007).

Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).

Maglia, Giovanni et al., "Enhanced translocation of single DNA molecules through alpha-hemolysin nanopores by manipulation of internal charge," PNAS, vol. 105(50):19720-19725 (2008).

Martin, Hugh et al., "Nanoscale Protein Pores Modified with PAMAM Dendrimers," J. Am. Chem. Soc., vol. 129:9640-9649 (2007).

Martinez, Javier et al., "The mRNA Cap Structure Stimulates Rate of Poly(A) Removal and Amplifies Processivity of Degradation," The Journal of Biological Chemistry, vol. 276(30):27923-27929 (2001).

Marziali, Andre et al., "New DNA Sequencing Methods," Annu. Rev. Biomed. Eng., vol. 3:195-223 (2001).

Mathe, Jerome et al., "Orientation discrimination of single-stranded DNA inside the alpha-hemolysin membrane channel," PNAS, vol. 102(35):12377-12382 (2005).

Matsuura, Shun-ichi et al., "Real-time observation of a single DNA digestion by I exonuclease under a fluorescence microscope field," Nucleic Acids Research, vol. 29(16):1-5 (2001).

Meller, Amit et al., "Rapid nanopore discrimination between single polynucleotide molecules," PNAS, vol. 97(3):1079-1084 (2000).

(56) References Cited

OTHER PUBLICATIONS

Meller, Amit et al., "Single molecule measurements of DNA transport through a nanopore," Electrophoresis, vol. 23: 2583-2591 (2002).
Meller, Amit, "Dynamics of polynucleotide transport through nanometre-scale pores," Journal of Physics: Condensed Matter, vol. 15:R581-R607 (2003).
Merzlyak, Petr G. et al., "Conductance and Ion Selectivity of a Mesoscopic Protein Nanopore Probed with Cysteine Scanning Mutagenesis," Biophysical Journal, vol. 89:3059-3070 (2005).
Mitchell, Nick et al., "Chemical Tags Facilitate the Sensing of Individual DNA Strands with Nanopores," Angew. Chem. Int Ed., vol. 47:5565-5568 (2008).
Mohammad, Mohammad M. et al., "Controlling a Single Protein in a Nanopore through Electrostatic Traps," J. Am. Chem. Soc., vol. 130:4081-4088 (2008).
Mol, Clifford D. et al., "Structure and function of the multifunctional DNA-repair enzyme exonuclease III," Nature, vol. 374:381-386 (1995).
Movileanu, Llviu et al "Detecting protein analytes that modulate transmembrane movement of a polymer chain within a single protein pore," Nature Biotechnology, vol. 18:1091-1095 (2001).
Movileanu, Liviu et al., "Location of a Construction in the Lumen of a Transmembrane Pore by Targeted Covalent Attachment of Polymer Molecules," J. Gen. Physiol., vol. 117:239-251 (2001).
Muller, Joachim et al., "Dna-directed assembly of artificial multienzyme complexes," Biochemical and Biophysical Research Communications, vol. 377:62-67 (2008).
Nakane, Jonathan et al., "A Nanosensor for Transmembrane Capture and Identification of Single Nucleic Acid Molecules," Biophysical Journal, vol. 87:615-621 (2004).
Nakane, Jonathan J. et al., "Nanopore sensors for nucleic acid analysis," J. Phys.: Condens. Matter, vol. 15:R1365-R1393 (2003).
Niemeyer, Christof M. et al., "DNA-Directed Assembly of Bienzymic Complexes from in Vivo Biotinylated NAD(P)H: FMN Oxidoreductase and Luciferase," ChemBioChem., vol. 3:242-245 (2002).
Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).
Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).
Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).
Phoenix, David A. et al., "OmpF-LPP Signal Sequence Mutants with Varying Charge Hydrophobicity Ratios Provide Evidence for a Phosphatidylglycerol-Signal Sequence Interaction during Protein Translocation across the *Escherichia coli* Inner Membrane," The Journal of Biological Chemistry, vol. 268(23):17069-17073 (1993).
Purnell, Robert F. et al., "Nucleotide Identificaiton and Orientation Discrimination of DNA Homopolymers Immobilized in a Protein Nanopore," Nano Letters, vol. 8(9):3029-3034 (2008).
Sanchez-Quesada, Jorge et al., "Cyclic Peptides as Molecular Adapters for a Pore-Forming Protein," Journal of the American Chemical Society, vol. 122(48):11757-11766 (2000).
Sanchez-Quesada, Jorge et al., "Single DNA Rotaxanes of a Transmembrane Pore Protein," Angew. Chem. Int. Ed., vol. 43:3063-3067 (2004).
Sanderson, Katherine, "Standard and Pores. Could the next generation of genetic sequencing machines be built froma collection of miniscule holes?" Nature News, vol. 456(7218):23-25 (2008).
Sauer-Budge, Alexis F. et al., "Unzipping Kinetics of Double-Stranded DNA in a Nanopore," Phys. Rev. Letters, vol. 90(23):238101-1-238101-4 (2003).
Seeman, Nadrian C., "Nucleic Acid Junctions and Lattices," J. theor. Biol., vol. 99:237-247 (1982).

Seo, Tae Seok et al., "Click Chemistry to Construct Fluorescent Oligonucleotides for DNA Sequencing," J. Org. Chem., vol. 68:609-612 (2003).
Seol, Yeonee, Stretching of Homopolymeric RNA Reveals Single-Stranded Helices and Base-Stacking, Physical Review Letters, vol. 98:158103, DOI: 10.1103/PhysRevLett.98.158103, 4 pages, (2007).
Shank, Lalida P. et al., "Redesigning Channel-Forming Peptides: Amino Acid Substitutions that Enhance Rates of Supramolecular Self-Assembly and Raise Ion Transport Activity," Biophysical Journal, vol. 90:2138-2150 (2006).
Shin, Seong-Ho et al., "Kinetics of a Reversible Covalent-Bond-Forming Reaction Observed at the Single-Molecule Level," Angew. Chem. Int. Ed., vol. 41(19):3707-3709 (2002).
Smeets, Ralph M.M. et al., "Salt Dependence of Ion Transport and DNA Translocation through Solid-State Nanopores," Nano Letters, vol. 6(1):89-95 (2006).
Song, Langzhou et al., "Structure of Staphylococcal alpha-Hemolysin, a Heptameric Transmembrane Pore," Science, vol. 274:1859-1866 (1996).
Stoddart, David et al., "Multiple base-recognition sites in a biological nanopore—two heads are better than one," Angew. Chem. Int. Ed. Engl., vol. 49(3):556-559 (2010).
Stoddart, David et al., "Single-nucleotide discrimination in immobilized DNA oligonucleotides with a biological nanopore," PNAS, vol. 106(19):7702-7707 (2009).
Sutherland, Todd C. et al., "An analysis of mismatched duplex DNA unzipping through a bacterial nanopore," Biochem. Cell Biol., vol. 82:407-412 (2004).
Tadey, Tanya et al., "Capillary electrophoretic separation of nucleotide isomers via complexation with cyclodextrin and borate," Journal of Chromatography B, vol. 657:365-372 (1994).
Thomas, Kirk R. et al., "Processivity of DNA Exonucleases," The Journal of Biological Chemistry, vol. 253(2):424-429 (1978).
Tohda, Koji et al., "Channel Mimetic Sensing Membranes for Nucleotides Based on Multitopic Hydrogen Bonding," Israel Journal of Chemistry, vol. 37:267-275 (1997).
Travers, Kevin J. et al., "A flexible and efficient template format for circular consensus sequencing and SNP detection," Nucleic Acids Research, vol. 38(15):e159, doi:10.1093/nar/gkq543 (2010).
Tung, Ching-Hsuan, "Preparation and Applications of Peptide-Oligonucleotide Conjugates," Bioconjugate Chemistry, vol. 11(5):605-618 (2000).
Van De Goor, Tom A., "Nanopore Detection: Threading DNA Through a Tiny Hole," PharmaGenomics, vol. 4(3):28-30 (2004).
Walker, Barbara et al., "Key Residues for Membrane Binding, Oligomerization and Pore Forming Activity of Staphylococcal alpha-Hemolysin Identified by Cysteine Scanning Mutagenesis and Targeted Chemical Modification," The Journal of Biological Chemistry, vol. 270 (39):23065-23071 (1995).
Wang, Hui et al., "Nanopores with a spark for single-molecule detection," Nature Biotechnology, vol. 19:622-623 (2001).
Wang, Qian et al., "Bioconjugation by Copper(I)-Catalyzed Azide-Alkyne [3+2] Cycloaddition," J. Am. Chem. Soc., vol. 125:3192-3193 (2003).
Wanunu, Meni et al., "DNA Translocation Governed by Interactions with Solid-State Nanopores," Biophysical Journal, vol. 95:4716-4725 (2008).
Wemmer, David E. et al., "Preparation and melting of single strand circular DNA loops," Nucleic Acids Research, vol. 13(23):8611-8621 (1985).
Winters-Hilt, Stephen et al., "Highly Accurate Classification of Watson-Crick Basepairs on Termini of Single DNA Molecules," Biophysical Journal, vol. 84:967-976 (2003).
Wolfe, Aaron J. et al., "Catalyzing the Translocation of Polypeptides through Attractive Interactions," J. Am. Chem. Soc., vol. 129:14034-14041 (2007).
Wong, C.T.A. et al., "Polymer capture by electro-osmotic flow of oppositely charged nanopores," The Journal of Chemical Physics, vol. 126:164903-1-164903-6 (2007).
Wu, Hai-Chen et al., "Protein Nanopores with Covalently Attached Molecular Adapters," J. Am. Chem. Soc., vol. 129:16142-16148 (2007).

(56) References Cited

OTHER PUBLICATIONS

Xie, Hongzhi et al., "Single-Molecule Observation of the Catalytic Subunit of cAMP-Dependent Protein Kinase Binding to an Inhibitor Peptide," Chemistry & Biology, vol. 12:109-120 (2005).
Yamagata, Atsushi et al., "Overexpression, purification and characterization of RecJ protein from Thermus thermophilus HB8 and its core domain," Nucleic Acids Research, vol. 29(22):4617-4624 (2001).
International Preliminary Report on Patentability and Written Opinion for Application No. PCT/GB2009/001679, 6 pages, dated Jan. 11, 2011.
International Preliminary Report on Patentability and Written Opinion for Appliction No. PCT/GB2009/001690, 9 pages, dated Jan. 11, 2011.
International Preliminary Report on Patentability for Application No. PCT/GB2006/004265, 7 pages, dated May 20, 2008.
International Preliminary Report on Patentability for Application No. PCT/GB2008/003372, 6 pages, dated Apr. 7, 2010.
International Search Report for Application No. PCT/GB2009/001679, 3 pages, dated Nov. 5, 2009.
International Search Report for Application No. PCT/GB2009/001690, 3 pages, dated Oct. 13, 2009.
Akeson, Mark et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77:3227-3233 (1999).
Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).
Ashkenasy, Nurit et al., "Recognizing a Single Base in an Individual DNA Strand: A Step Toward DNA Sequencing in Nanopores," Angew. Chem. Int. Ed., vol. 44:1401-1404 (2005).
Ashkenasy, Nurit et al., "Single Nucleobase Sensitivity of a-Hemolysin (a-HL) Transmembrane Protein Pore: Toward Single DNA Sequencing," ACS National Meeting, vol. 45(13), Abstract No. 74 (2005).
Astier, Yann et al., "Stochastic Detection of Motor Protein-RNA Complexes by Single-Channel Current Recording," ChemPhysChem, vol. 8:2189-2194 (2007).
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc., vol. 128:1705-1710 (2006).
Bayley, Hagan et al., "Stochastic sensors inspired by biology," Nature, vol. 413:226-230 (2001).
Bayley, Hagan, "Sequencing single molecules of DNA," Current Opinion in Chemical Biology, vol. 10:628-637 (2006).
Benner, Seico et al., "Sequence-specific detection of individual DNA polymerase complexes in real time using a nanopore," Nature Nanotechnology, vol. 2:718-724 (2007).
Braha, Orit et al., "Carriers versus Adapters in Stochastic Sensing," ChemPhysChem., vol. 6:889-892 (2005).
Braha, Orit et al., "Designed protein pores as components for biosensors," Chemistry & Biology, vol. 4:497-505 (1997).
Branton, Daniel et al., "The potential and challenges of nanopore sequencing," Nat. Biotechnol., vol. 26 (10):1146-1153 (2008).
Braslavsky, Ido et al., "Sequence information can be obtained from single DNA molecules," PNAS, vol. 100 (7):3960-3964 (2003).
Budanova, Natalia et al., "Heptakis(6-amino-6-deoxy)-beta-cyclodextrin as a chiral selector for the separation of anionic analyte enantiomers by capillary electrophoresis," Electrophoresis, vol. 25:2795-2800 (2004).
Busam, Robert D., "Structure of *Escherichia coli* exonuclease I in complex with thymidine 5'-monophosphate," Acta Cryst., vol. D64:206-210 (2008).
Butler, Tom Z. et al., "Determination of RNA Orientation during Translocation through a Biological Nanopore," Biophysical Journal, vol. 90:190-199 (2006).
Butler, Tom Z. et al., "Single-molecule DNA detection with an engineered MspA protein nanopore," PNAS, vol. 105 (52):20647-20652 (2008).
Chan, Eugene Y., "Advances in sequencing technology," Mutation Research, vol. 573:13-40 (2005).
Cheley, Stephen et al., "A functional protein pore with a 'retro' transmembrane domain," Protein Science, vol. 8:1257-1267 (1999).
Cheley, Stephen et al., "A Genetically Encoded Pore for the Stochastic Detection of a Protein Kinase," ChemBioChem, vol. 7:1923-1927 (2006).
Cheley, Stephen et al., "Spontaneous oligomerization of a staphylococcal alpha-hemolysin conformationally constrained by removal of residues that form the transmembrane beta-barrel," Protein Engineering, vol. 10 (12):1433-1443 (1997).
Cheley, Stephen et al., "Stochastic Sensing of Nanomolar Inositol 1,4,5-Trisphosphate with an Engineered Pore," Chemistry & Biology, vol. 9:829-838 (2002).
Chen, Min et al., "Outer membrane protein G: Engineering a quiet pore for biosensing," PNAS, vol. 105 (17):6272-6277 (2008).
Chen, Peng et al., "Atomic Layer Deposition to Fine-Tune the Surface Properties and Diameters of Fabricated Nanopores," Nano Letters, vol. 4(7):1333-1337 (2004).
Clarke, James et al., "Continuous base identification for single-molecule nanopore DNA sequencing," Nature Nanotechnology, vol. 4:265-270 (2009).
Cockroft, Scott L. et al., "A Single-Molecule Nanopore Device Detects DNA Polymerase Activity with Single-Nucleotide Resolution," J. Am. Chem. Soc., vol. 130:818-820 (2008).
Comai, Massimiliano et al., "Protein engineering modulates the transport properties and ion selectivity of the pores formed by staphylococcal gamma-haemolysins in lipid membranes," Molecular Microbiology, vol. 44(5):1251-1257 (2002).
Cudic, Predrag et al., "Binding of Nucleotides in Water by Phenathridinium Bis(intercaland) Receptor Molecules," J. Chem. Soc., Chem. Commun., pp. 1073-1075 (1995).
Dapprich, Johannes, "Single-Molecule DNA Digestion by Lambda-Exonuclease," Cytometry, vol. 36:163-168 (1999).
Deamer, David W. et al., "Characterization of Nucleic Acids by Nanopore Analysis," Ac. Chem. Res., vol. 35:817-825 (2002).
Deamer, David W. et al., "Nanopores and nucleic acids: prospects for ultrarapid sequencing," TIBTECH, vol. 18:147-151 (2000).
Dorre, Klaus et al., "Techniques for single molecule sequencing," Bioimaging, vol. 5:139-152 (1997).
Eid, John et al., "Real-Time DNA Sequencing from Single Polymerase Molecules," Science, vol. 323:133-138 (2009).
Eliseev, Alexey V. et al., "Aminocyclodextrins as Selective Hosts with Several Binding Sites for Nucleotides," Angew. Chem. Int. Ed. Engl., vol. 32(9)1331-1333 (1993).
Eliseev, Alexey V. et al., "Molecular Recognition of Nucleotides, Nucleosides, and Sugars by Aminocyclodextrins," J. Am. Chem. Soc., vol. 116:6081-6088 (1994).
Erie, Dorothy et al., "A Dumbell-Shaped, Double-Hairpin Structure of DNA: A Thermodynamic Investigation," Biochemistry, vol. 26:7150-7159 (1987).
Flomenbom, O. et al., "Single stranded DNA translocation through a nanopore: A master equation approach," Physical Review E, vol. 68:041910-1-041910-7 (2003).
Flusberg, Benjamin A. et al., "Direct detection of DNA methylation during single-molecule, real-time sequencing," Nature Methods, vol. 7(6):461-465 (2010).
Genschel, Jochen et al., "Interaction of *E. coli* Single-Stranded DNA Binding Protein (SSB) with Exonuclease I. The Carboxy-Terminus of SSB Is the Recognition Site fo the Nuclease," Biol. Chem., vol. 381:183-192 (2000).
Gershow, Marc et al., "Recapturing and trapping single molecules with a solid-state nanopore," Nature Nanotechnology, vol. 2:775-779 (2007).
Ghosal, Sandip, "Electrokinetic-flow-induced viscous drag on a tethered DNA inside a nanopore," Physical Review E, vol. 76:061916-1-061916-3 (2007).
Gu, Li-Qun et al., "Capture of a Single Molecule in a Nanocavity," Science, vol. 291:636-640 (2001).

(56) References Cited

OTHER PUBLICATIONS

Gu, Li-Qun et al., "Electroosmotic enhancement of the binding of a neutral molecule to a transmembrane pore," PNAS, vol. 100(26):15498-15503 (2003).
Gu, Li-Qun et al., "Prolonged Residence Time of a Noncovalent Molecular Adapter, beta-Cyclodextrin, within the Lumen of Mutant alpha-Hemolysin Pores," J. Gen. Physiol., vol. 118:481-493 (2001).
Gu, Li-Qun et al., "Reversal of charge selectivity in transmembrane protein pores by using noncovalent molecular adapters," PNAS, vol. 97(8):3959-3964 (2000).
Gu, Li-Qun et al., "Stochastic sensing of organic analytes by a pore-forming protein containing a molecular adapter," Nature, vol. 398:686-690 (1999).
Guan, Xiyun et al., "Stochastic Sensing of Tnt with a Genetically Engineered Pore," ChemBioChem, vol. 6:1875-1881 (2005).
Han, Eugene S. et al., "RecJ exonuclease: substrates, products and interaction with SSB," Nucleic Acids Research, vol. 34(4):1084-1091 (2006).
Han, Jongyoon et al., "Characterization and Optimization of an Entropic Trap for DNA Separation," Anal. Chem., vol. 74:394-401 (2002).
Hein, Christopher D. et al., "Click Chemistry, a Powerful Tool for Pharmaceutical Sciences," Pharm. Res., vol. 25 (10):2216-2230 (2008).
U.S. Appl. No. 14/391,660, filed Oct. 9, 2014, Mark Bruce.
U.S. Appl. No. 13/968,778, Mar. 20, 2015.
U.S. Appl. No. 13/002,717, Dec. 3, 2014.
U.S. Appl. No. 13/147,159, Mar. 20, 2015.
U.S. Appl. No. 13/147,176, May 8, 2015.
U.S. Appl. No. 13/147,176, Oct. 20, 2014.
U.S. Appl. No. 13/260,178, Feb. 26, 2015.
Akeson (2013), PNAS, Error rates for nanopore discrimination CmC HOMC.
Astier et al., Chemical Biology, 2005, 9, 576-584.
Ball, K. et al, RUE 2006 Student Presenations and Paper, Jun. 19-Aug. 25, 2006, pp. 1-31.
Bayley & Jayasinghe, Molecular Membrane Biology, 2004, 21, 209-220.
Bayley at al., Nature Structural & Molecular Biology, 2005, 2, 385-386.
Bayley et al., Angew. Chem. Int. Ed., 2003, 42, 3766-3771.
Bayley et al., Angew. Chem. Int. Ed., 2005, 44, 1495-1499.
Bayley H., Biotechnology, 1999, 10, 94-103.
Bayley H., Journal of Cellular Biochemistry, 1994, 56, 177-182.
Braha et al., Nature Biotechnology, 2000, 18, 105-107.
Butler, T., Nanopore Analysis of Nucleic Acids Thesis, University of Washington, 2007, pp. 1-120.
Chang et al., Chemistry & Biology, 1995, 2, 391-400.
Cheri et al., Nat Biotechnol., 2012, 30(4), 344-348.
Dahl et al., J. Biol. Chem., 2012, 287, 3407-13421.
Danilchanka et al., Antimicrobial Agents and Chemotherapy, 52, 2008, p. 3127-3134.
DeGuzman et al., Nucleic Acids Research, 2006, 34,6425-6437.
Derrington et al., PNAS, 2010, 107, 16060-16065.
Engelhardt et al.,The Journal of Biological Chemistry, 2002, 277, 37567-37572.
Fang et al., Biochemistry, 1997, 36, 9518-9522.
Garalde et al., Journal of Biological Chemistry, 2011, 286, 14480-14492.
Gouaux et al., Proc. Natl. Acad. Sci. USA, 1994, 91, 12828-12831.
Gouaux et al., Science, 1996, 274, 1859-1866.
Gu et l., Biophysical Journal, 2000, 79, 1967-1975.
Gundlach, J. Engineering MspA for Nanopore Sequencing, Sep. 26, 2006-Aug. 31, 2008, Abstract, p. 1.
Gyarfas et al., ACS Nano, 2009, 3, 1457-1466.
Gyarfas et al., Annu. Rev. Biophys., 2010, 39, 79-90.
Heinz et al., Analytical Biochemistry, 2000, 285, 113-120.
Heinz et al., Journal of Chromatography B, 2003, 790, 337-348.
Heinz et al., The Journal of Biological Chemistry, 2003, 10, 8678-8685.
Howorka et al., Angew. Chem. Int. Ed., 2004, 43, 842-842.
Hurt et al., J. Am. Chem. Soc., 2009, 131(10), 3772-3778.
Jayasinghe et al., The Journal of Biological Chemistry, 2006, 281, 2195-2204.
Kang et al., Angew. Chem. Int. Ed., 2005, 44, 1401-1404.
Kang et al., J. Am.Chem.Soc., 2006, 128, 10684-10685.
Kasianowicz et al., Biophysical Journal Volume, 1999, 76, 837-845.
Krishnasastry,et al., FEBS Letters, 1994, 356, 66-71.
Langford et al., American Society for Biochemistry and Molecular Biology, Inc., 52, 2011, 272-277.
Laszlo et al., PNAS, 2013, 110 (47), 18904-18909.
Liberman et al., J. Am.Chem.Soc., 2010, 132, 17961-17972.
Lieberman et al., Am. Chem. Soc., 2013, 135(24), 9149-9155.
Lieberman et al., J. Am.Chem.Soc., 2012, 134(45), 18816-18823.
Luchian et al., Angew. Chem. Int. Ed., 2003, 42, 1925-1929.
Mahfoud et al., The Journal of Biological Chemistry, 2006, 281, 5908-5915.
Mailaender et al., Microbiology, 2004, 853-864.
Manrao et al., NIH, 2012, 30(4), 349-353.
Manrao et al., Plos One, 2011, 6(10), 1-7.
Michael Faller et al., Science, 2004, 303, 1189-1192.
Miles et al., Biochemistry 2001, 40, 8514-8522.
Miles et al., Journal of Biological Chemistry, 2006, 281, 2205-2214.
Miles et al., Protein Science, 2002, 11, 894-902.
Movileanu & Bayley, PNAS, 2001, 98, 10137-10141.
Movileanu et al., Biophysical Journal Volume, 2003, 85, 897-910.
Movileanu et al., Nature Biotechnology, 2000, 18, 1091-1095.
Nakane et al., Electrophoresis, 2002, 23, 2592-2601.
Niederweis et al., Molecular Microbiology, 1999, 33(5), 933-945.
Niederweis M., Molecular Microbiology, 2003, 49(5), 1167-1177.
Niederweis, M., Mycobacterial porins—new channel proteins in unique membranes, Lecture Abstract, No date available, pp. 1-69.
Nivala et al. Nat Biotechnol., 2013, 31(3), 247-250.
Olasagasti et al., Nature Nanotechnology, 2010, 5, 798-806.
Panchal &Bayley, The Journal of Biological Chemistry, 1995, 270, 23072-23076.
Pavlenok et al., Pos One, 2012, 7(6), 1-12.
Schreiber et al., PNAS, 2013, 110 (47), 18910-18915.
Song et al., NIH, 2008 ,88(6), 526-544.
Stahl et al., Molecular Biology, 2001, 40(2), 451-464.
Stephan et al., Molecular Microbiology, 2005, 58 (3), 714-730.
Szabo et al., J. Biol. Chem., 1997, 272, 25275-25282.
Tobkes et al., Biochemistry, 1985, 24, 1915-1920.
Trias et al., Molecular Biology, 1994, 14(2), 283-290.
Trias et al., Science, 1992, 258, 1479-1481.
Valeva et al., Proc. Natl. Acad. Sci. USA, 1997, 94, 11607-11611.
Valeva et al., The EMBO Journal, 1996, 15, 1857-1864.
Vercoutere et al. Nucleic Acids Research, 2003, 31, 1311-1318.
Vercoutere et al., Nature Biotechnology, 2001, 19, 248-252.
Vercoutere W. & Akeson M., Chemical Biology 2002, 6, 816-822.
Walker et al., Protein Engineering, 1994, 7(5), 655-662.
Walker et al., Chemistry & Biology, 1995, 2, 99-105.
Walker et al., Journal of Cellular Biochemistry, 1994, 56, 177-182.
Walker et al., Protein Engineering, 1994, 7, 91-97.
Walker et al., The Journal of Biological Chemistry, 1992, 267, 21782-21766.
Walker et al., The Journal of Biological Chemistry, 1993, 268, 5285-5292.
Wang et al., PNAS, 2004, 101, 13472-13477.
Wilson et al., 2008, Conf Proc. IEEE—Feedback control of a DNA molecule.
Wilson et al., ACS Nano., 2009, 3(4), 995-1003.
Winters-Hilt et al., BMC Bioinformatics 2006, 7, 1-18.
Winters-Hilt. S & Akeson M., DNA and Cell Biology, 2004, 23, 675-683.
Wong, R., Engineering *Mycobacterium smegmatis* Porin A (MspA) for DNA Analysis, University of Washington Summer Research Poster Session, pamphlet cover, program description, schedule of events, abstract and poster, presentation date Aug. 16, 2007, 5 pages.
Worner, et al., Small, 2007, 3, 1084.

(56) References Cited

OTHER PUBLICATIONS

Avrameas et al., "Coupling of Enzymes to Proteins with Glutaraldehyde: Use of the Conjugates for the Detection of Antigens and Antibodies," Immunochemistry, vol. 6, pp. 43-52, (1969).
U.S. Appl. No. 13/147,176, Lakmal Jayasinghe, filed Nov. 18, 2011, Aug. 31, 2015.
U.S. Appl. No. 14/858,138, filed Sep. 18, 2015, L. Jayasinghe.
U.S. Appl. No. 13/147,159, B. Mckeown, filed Nov. 15, 2011, Oct. 20, 2015.
U.S. Appl. No. 14/455,394, L. Jayasinghe, filed Aug. 8, 2014, Oct. 2, 2015.
U.S. Appl. No. 13/002,717, Jan. 22, 2016.
U.S. Appl. No. 13/002,717, Jul. 21, 2015.

SEQUENCE LISTING

<160> NUMBER OF SEQ ID NOS: 15

<210> SEQ ID NO 1
<211> LENGTH: 882
<212> TYPE: DNA
<213> ORGANISM: Staphylococcus aureus

<400> SEQUENCE: 1

| | | | | | |
|---|---|---|---|---|---|
| atggcagatt | ctgatattaa | tattaaaacc | ggtactacag | atattggaag | caatactaca | 60 |
| gtaaaaacag | gtgatttagt | cacttatgat | aaagaaaatg | gcatgcacaa | aaaagtattt | 120 |
| tatagtttta | tcgatgataa | aaatcacaat | aaaaaactgc | tagttattag | aacaaaaggt | 180 |
| accattgctg | gtcaatatag | agtttatagc | gaagaaggtg | ctaacaaaag | tggtttagcc | 240 |
| tggccttcag | cctttaaggt | acagttgcaa | ctacctgata | tgaagtagc | tcaaatatct | 300 |
| gattactatc | caagaaattc | gattgataca | aaagagtata | tgagtacttt | aacttatgga | 360 |
| ttcaacggta | atgttactgg | tgatgataca | ggaaaaattg | gcggccttat | tggtgcaaat | 420 |
| gtttcgattg | gtcatacact | gaaatatgtt | caacctgatt | tcaaaacaat | tttagagagc | 480 |
| ccaactgata | aaaagtagg | ctggaaagtg | atatttaaca | atatggtgaa | tcaaaattgg | 540 |
| ggaccatacg | atcgagattc | ttggaacccg | gtatatggca | atcaactttt | catgaaaact | 600 |
| agaaatggtt | ctatgaaagc | agcagataac | ttccttgatc | ctaacaaagc | aagttctcta | 660 |
| ttatcttcag | gttttcacc | agacttcgct | acagttatta | ctatggatag | aaaagcatcc | 720 |
| aaacaacaaa | caaatataga | tgtaatatac | gaacgagttc | gtgatgatta | ccaattgcat | 780 |
| tggacttcaa | caaattggaa | aggtaccaat | actaaagata | aatggacaga | tcgttcttca | 840 |
| gaaagatata | aaatcgattg | ggaaaaagaa | gaaatgacaa | at | | 882 |

```
<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin RL2

<400> SEQUENCE: 3
atggcagatt ctgatattaa tattgcaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
```

```
accattgctg gtcaatatag agtttatagc gaagaaggtg ctaacaaaag tggtttagcc    240
tggccttcag cctttaaggt acagttgcaa ctacctgata atgaagtagc tcaaatatct    300
gattactatc cgcggaattc gattgataca aagagtata tgagtacgtt aacgtacgga     360
ttcaacggta accttactgg tgatgatact agtaaaattg gaggccttat tggggcccag    420
gtttccctag gtcatacact taagtatgtt caacctgatt tcaaaacaat tctcgagagc    480
ccaactgata aaaagtagg ctggaaagtg atatttaaca atatggtgaa tcaaaattgg     540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga gtaatatac gaacgagttc gtgatgatta ccaattgcat     780
tggacttcaa caaattggaa aggtaccaat actaaagata aatggacaga tcgttcttca    840
gaaagatata aaatcgattg ggaaaaagaa gaaatgacaa attaa                   885
```

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin RL2

<400> SEQUENCE: 4

```
Ala Asp Ser Asp Ile Asn Ile Ala Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240
```

-continued

```
Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290
```

<210> SEQ ID NO 5
<211> LENGTH: 885
<212> TYPE: DNA
<213> ORGANISM: Artificial sequence
<220> FEATURE:
<223> OTHER INFORMATION: alpha-hemolysin M113R-WT

<400> SEQUENCE: 5

| | | | | | |
|---|---|---|---|---|---|
| atggcagatt | ctgatattaa | tattaaaacc | ggtactacag | atattggaag | caatactaca | 60 |
| gtaaaaacag | gtgatttagt | cacttatgat | aaagaaaatg | gcatgcacaa | aaaagtattt | 120 |
| tatagttta | tcgatgataa | aaatcacaat | aaaaaaactgc | tagttattag | aacaaaaggt | 180 |
| accattgctg | gtcaatatag | agtttatagc | gaagaaggtg | ctaacaaaag | tggtttagcc | 240 |
| tggccttcag | cctttaaggt | acagttgcaa | ctacctgata | atgaagtagc | tcaaatatct | 300 |
| gattactatc | caagaaattc | gattgataca | aaagagtata | ggagtacttt | aacttatgga | 360 |
| ttcaacggta | atgttactgg | tgatgataca | ggaaaaattg | gcggccttat | tggtgcaaat | 420 |
| gtttcgattg | gtcatacact | gaaatatgtt | caacctgatt | tcaaaacaat | tttagagagc | 480 |
| ccaactgata | aaaagtagg | ctggaaagtg | atatttaaca | atatggtgaa | tcaaaattgg | 540 |
| ggaccatacg | atcgagattc | ttggaacccg | gtatatggca | tcaacttttt | catgaaaact | 600 |
| agaaatggtt | ctatgaaagc | agcagataac | ttccttgatc | ctaacaaagc | aagttctcta | 660 |
| ttatcttcag | ggttttcacc | agacttcgct | acagttatta | ctatggatag | aaaagcatcc | 720 |
| aaacaacaaa | caaatataga | tgtaatatac | gaacgagttc | gtgatgatta | ccaattgcat | 780 |
| tggacttcaa | caaattggaa | aggtaccaat | actaaagata | aatggacaga | tcgttcttca | 840 |
| gaaagatata | aaatcgattg | ggaaaaagaa | gaaatgacaa | attaa | | 885 |

<210> SEQ ID NO 6
<211> LENGTH: 293
<212> TYPE: PRT
<213> ORGANISM: Artificial sequence
<220> FEATURE:
<223> OTHER INFORMATION: alpha-hemolysin M113R-WT

<400> SEQUENCE: 6

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
```

|  |  | 85 |  |  |  | 90 |  |  |  | 95 |  |
|---|---|---|---|---|---|---|---|---|---|---|---|

Gln Ile Ser Asp Tyr Tyr Pro Arg Asn Ser Ile Asp Thr Lys Glu Tyr
                        100                 105                 110

Arg Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                    180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                    245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn
        290

```
<210> SEQ ID NO 7
<211> LENGTH: 885
<212> TYPE: DNA
<213> ORGANISM: Artificial sequence
<220> FEATURE:
<223> OTHER INFORMATION: alpha-hemolysin E111N-WT

<400> SEQUENCE: 7
```

| | | |
|---|---|---|
| atggcagatt ctgatattaa tattaaaacc ggtactacag atattggaag caatactaca | | 60 |
| gtaaaaacag gtgatttagt cacttatgat aaagaaaatg gcatgcacaa aaagtatttt | | 120 |
| tatagtttta tcgatgataa aaatcacaat aaaaaactgc tagttattag aacaaaaggt | | 180 |
| accattgctg tcaatatag agtttatagc gaagaaggtg ctaacaaaag tggtttagcc | | 240 |
| tggccttcag cctttaaggt acagttgcaa ctacctgata tgaagtagc tcaaatatct | | 300 |
| gattactatc caagaaattc gattgataca aaaactata tgagtacttt aacttatgga | | 360 |
| ttcaacggta atgttactgg tgatgataca ggaaaaattg gcggccttat tggtgcaaat | | 420 |
| gtttcgattg gtcatacact gaaatatgtt caacctgatt tcaaaacaat tttagagagc | | 480 |
| ccaactgata aaaagtagg ctggaaagtg atatttaaca atatggtgaa tcaaaattgg | | 540 |
| ggaccatacg atcgagattc ttggaacccg gtatatggca atcaactttt catgaaaact | | 600 |
| agaaatggtt ctatgaaagc agcagataac ttccttgatc ctaacaaagc aagttctcta | | 660 |
| ttatcttcag ggttttcacc agacttcgct acagttatta ctatggatag aaaagcatcc | | 720 |
| aaacaacaaa caaatataga tgtaatatac gaacgagttc gtgatgatta ccaattgcat | | 780 |
| tggacttcaa caaattggaa aggtaccaat actaaagata aatggacaga tcgttcttca | | 840 | gaaagatata aaatcgattg ggaaaaagaa gaaatgacaa attaa                                   885

<210> SEQ ID NO 8
<211> LENGTH: 293
<212> TYPE: PRT
<213> ORGANISM: Artificial sequence
<220> FEATURE:
<223> OTHER INFORMATION: alpha-hemolysin E111N-WT

<400> SEQUENCE: 8

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 9
<211> LENGTH: 885
<212> TYPE: DNA
<213> ORGANISM: Artificial sequence
<220> FEATURE:
<223> OTHER INFORMATION: alpha-hemolysin A8R-RL2

<400> SEQUENCE: 9

```
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct    300
gattactatc cgcggaattc gattgataca aaagagtata tgagtacgtt aacgtacgga   360
ttcaacggta accttactgg tgatgatact agtaaaattg gaggcctttat tggggcccag   420
gtttccctag gtcatacact taagtatgtt caacctgatt tcaaaacaat tctcgagagc   480
ccaactgata aaaagtagg ctggaaagtg atatttaaca atatggtgaa tcaaaattgg    540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaatatac gaacgagttc gtgatgatta ccaattgcat   780
tggacttcaa caaattggaa aggtaccaat actaaagata aatggacaga tcgttcttca   840
gaaagatata aaatcgattg ggaaaaagaa gaaatgacaa attaa              885
```

<210> SEQ ID NO 10
<211> LENGTH: 293
<212> TYPE: PRT
<213> ORGANISM: Artificial sequence
<220> FEATURE:
<223> OTHER INFORMATION: alpha-hemolysin A8R-RL2

<400> SEQUENCE: 10

```
Ala Asp Ser Asp Ile Asn Ile Arg Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205
```

```
Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 11
<211> LENGTH: 885
<212> TYPE: DNA
<213> ORGANISM: Artificial sequence
<220> FEATURE:
<223> OTHER INFORMATION: alpha-hemolysin M113K-RL2

<400> SEQUENCE: 11

```
atggcagatt ctgatattaa tattgcaacc ggtactacag atattggaag caatactaca      60
gtaaaaacag gtgatttagt cacttatgat aagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct     300
gattactatc cgcggaattc gattgataca aagagtata agagtacgtt aacgtacgga     360
ttcaacggta accttactgg tgatgatact agtaaaattg gaggccttat tggggcccag     420
gtttccctag gtcatacact taagtatgtt caacctgatt tcaaaacaat tctcgagagc     480
ccaactgata aaaagtagg ctggaaagtg atatttaaca atatggtgaa tcaaaattgg     540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag gttttcacc agacttcgct acagttatta ctatggatag aaaagcatcc     720
aaacaacaaa caaatataga tgtaatatac gaacgagttc gtgatgatta ccaattgcat     780
tggacttcaa caaattggaa aggtaccaat actaaagata atggacaga tcgttcttca     840
gaaagatata aaatcgattg ggaaaaagaa gaaatgacaa attaa                     885
```

<210> SEQ ID NO 12
<211> LENGTH: 293
<212> TYPE: PRT
<213> ORGANISM: Artificial sequence
<220> FEATURE:
<223> OTHER INFORMATION: alpha-hemolysin M113K-RL2

<400> SEQUENCE: 12

```
Ala Asp Ser Asp Ile Asn Ile Ala Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60
```

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Lys Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 13
<211> LENGTH: 885
<212> TYPE: DNA
<213> ORGANISM: Artificial sequence
<220> FEATURE:
<223> OTHER INFORMATION: alpha-hemolysin M113R-RL2

<400> SEQUENCE: 13
atggcagatt ctgatattaa tattgcaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaaactg ctagttatta aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300 gattactatc cgcggaattc gattgataca aaagagtata gaagtacgtt aacgtacgga     360
ttcaacggta accttactgg tgatgatact agtaaaattg gaggccttat tggggcccag     420
gtttccctag tcatacact taagtatgtt caacctgatt tcaaaacaat tctcgagagc      480
ccaactgata aaaagtagg ctggaaagtg atatttaaca atatggtgaa tcaaaattgg      540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720

```
aaacaacaaa caaatataga tgtaatatac gaacgagttc gtgatgatta ccaattgcat      780
tggacttcaa caaattggaa aggtaccaat actaaagata aatggacaga tcgttcttca      840
gaaagatata aatcgattg ggaaaaagaa gaaatgacaa attaa                       885
```

<210> SEQ ID NO 14
<211> LENGTH: 293
<212> TYPE: PRT
<213> ORGANISM: Artificial sequence
<220> FEATURE:
<223> OTHER INFORMATION: alpha-hemolysin M113R-RL2

<400> SEQUENCE: 14

```
Ala Asp Ser Asp Ile Asn Ile Ala Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 15
<211> LENGTH: 92
<212> TYPE: DNA
<213> ORGANISM: Artificial sequence -continued

```
<220> FEATURE:
<223> OTHER INFORMATION: Test DNA Sequence

<400> SEQUENCE: 15
aaaaaaaaaa aaaaaaaaaa attcccccccc cccccccccc cccctttaaaa aaaaaattcc      60 cccccccctt aaaaaaaaaa ttcccccccc cc                                     92
```

METHODS OF ENHANCING TRANSLOCATION OF CHARGED ANALYTES THROUGH TRANSMEMBRANE PROTEIN PORES

RELATED APPLICATIONS

This application is a divisional application of U.S. patent application Ser. No. 13/129,278, filed Aug. 26, 2011, which is a 35 U.S.C. 371 national stage filing of International Application No. PCT/GB2009/002666 filed Nov. 13, 2009, which claims priority to GB Application No. 0820927.2 filed Nov. 14, 2008. The contents of the aforementioned applications are hereby incorporated by reference.

FIELD OF THE INVENTION

The invention relates to enhancing translocation of a charged analyte through a transmembrane protein pore. Translocation is enhanced by increasing the net opposing charge of the barrel or channel and/or entrance of the pore. The invention also relates to a pore enhanced in accordance with the invention.

BACKGROUND OF THE INVENTION

Stochastic detection is an approach to sensing that relies on the observation of individual binding events between analyte molecules and a receptor. Stochastic sensors can be created by placing a single pore of nanometer dimensions in an insulating membrane and measuring voltage-driven ionic transport through the pore in the presence of analyte molecules. The frequency of occurrence of fluctuations in the current reveals the concentration of an analyte that binds within the pore. The identity of an analyte is revealed through its distinctive current signature, notably the duration and extent of current block (Braha, O., Walker, B., Cheley, S., Kasianowicz, J. J., Song, L., Gouaux, J. E., and Bayley, H. (1997) *Chem. Biol.* 4, 497-505; and Bayley, H., and Cremer, P. S. (2001) *Nature* 413, 226-230).

Engineered versions of the bacterial pore-forming toxin α-hemolysin (α-HL) have been used for stochastic sensing of many classes of molecules (Bayley, H., and Cremer, P. S. (2001) *Nature* 413, 226-230; Shin, S.-H., Luchian, T., Cheley, S., Braha, O., and Bayley, H. (2002) *Angew. Chem. Int. Ed.* 41, 3707-3709; and Guan, X., Gu, L.-Q., Cheley, S., Braha, O., and Bayley, H. (2005) *ChemBioChem* 6, 1875-1881). In the course of these studies, it was found that attempts to engineer α-HL to bind small organic analytes directly can prove taxing, with rare examples of success (Guan, X., Gu, L.-Q., Cheley, S., Braha, O., and Bayley, H. (2005) *ChemBioChem* 6, 1875-1881).

SUMMARY OF THE INVENTION

When analytes translocate through a transmembrane protein pore, they are capable of affecting the current flowing through the pore in a manner specific for that analyte. This allows the analyte to be detected using stochastic sensing. The analyte usually affects the current flowing through a pore by interacting with the pore. A distinctive current flows through the pore whenever the analyte interacts with the pore.

The inventors have surprisingly demonstrated that increasing the net opposing charge of the barrel or channel and/or entrance of a pore enhances the translocation of charged analytes through the pore. For instance, increasing the net positive charge of the barrel or channel and/or entrance of a pore enhances the translocation of negatively charged analytes through the pore. Increasing the net opposing charge of the barrel or channel and/or entrance increases the frequency of translocation of the analyte through the pore. It also decreases the threshold voltage for translocation of the analyte through the pore. It also decreases the translocation speed of the analyte through the pore. Further, events in which the analyte enters the pore, but is not translocated, are almost eliminated. Pores enhanced in this way are useful tools for stochastic sensing of charged analytes, especially for sequencing nucleic acids.

The invention therefore provides a method of enhancing translocation of a charged analyte through a transmembrane protein pore, comprising:
 (a) increasing the net opposing charge of the barrel or channel and/or entrance of the pore; and
 (b) determining whether or not translocation of the analyte through the resulting pore is enhanced.

The invention also provides:
 use of an increase in net opposing charge of the barrel or channel and/or entrance of a transmembrane protein pore to enhance translocation of a charged analyte through the pore;
 a transmembrane protein pore enhanced by a method of the invention;
 a transmembrane protein pore in which the net opposing charge of its barrel or channel and/or entrance has been increased to enhance the translocation of a charged analyte through the pore;
 a polynucleotide encoding a transmembrane protein pore of the invention;
 a polynucleotide encoding a transmembrane protein pore subunit having the sequence of SEQ ID NO: 6, 8 or 10 or a variant thereof;
 a method of determining presence or absence of an analyte in a sample, comprising:
 (a) contacting the sample with a transmembrane protein pore of the invention under conditions that allow the analyte, if present, to translocate through and interact with the pore; and
 (b) measuring the current passing through the pore during the interaction and thereby determining the presence or absence of the analyte;
 a method of sequencing a target nucleic acid sequence, comprising:
 (a) pushing or pulling the target sequence through a transmembrane protein pore of the invention so that a proportion of the nucleotides in the target sequence interact with the pore; and
 (b) measuring the current passing through the pore during each interaction and thereby determining the sequence of the target sequence; and
 a kit for sequencing a nucleic acid, comprising a transmembrane protein pore of the invention and a nucleic acid handling enzyme.

DESCRIPTION OF THE SEQUENCE LISTING

Figure 1:
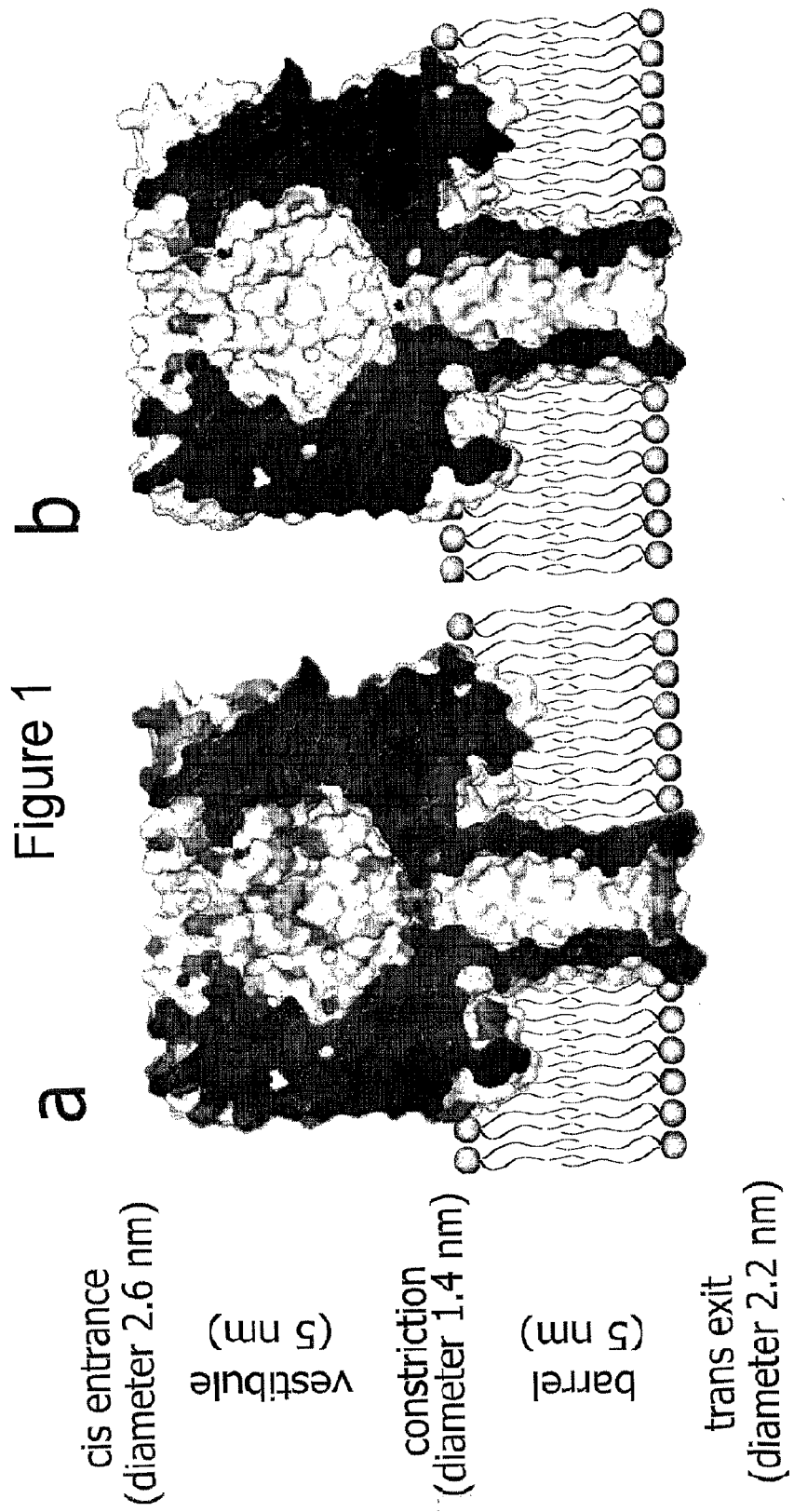
FIG. 1 shows sections through the α-hemolysin (α-HL) nanopore (PDB: 7AHL). (a) Charge distribution in the WT α-HL nanopore. Positively charged amino acids of α-HL are coloured in blue and negatively charged amino acids in red. (b) Sites in the α-HL nanopore modified in this work. Lys-8 is in purple. The constriction formed by the ion pair Glu-111/Lys-147 is coloured in green. Met-113, Thr-115, Thr-117, Gly-119, Asn-121, Asn-123 and Thr-125 are in orange.

SEQ ID NO: 1 shows the polynucleotide sequence that encodes one subunit of wild-type (WT) α-hemolysin.

SEQ ID NO: 2 shows the amino acid sequence of one subunit of WT α-hemolysin. Amino acids 2 to 6, 73 to 75, 207 to 209, 214 to 216 and 219 to 222 form α-helices. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 form β-strands. All the other non-terminal amino acids, namely 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 form loop regions. Amino acids 1 and 294 are terminal amino acids.

SEQ ID NO: 3 shows the polynucleotide sequence that encodes one subunit of α-hemolysin RL2. RL2 is the product of a semisynthetic gene that was devised to permit cassette mutagenesis of the sequence encoding the transmembrane β barrel (Cheley, S., Braha, O., Lu, X., Conlan, S., and Bayley, H. (1999) *Protein Sci.* 8, 1257-1267). It contains six silent restriction sites and five altered amino acids in the encoded polypeptide sequence (K8A, V124L, G130S, N139Q and I142L). D8RL2 is RL2 with an octa-aspartate tail.

SEQ ID NO: 4 shows the amino acid sequence of one subunit of α-hemolysin RL2. The same amino acids discussed above for SEQ ID NO: 2 form α-helices, β-strands, loop regions and terminal amino acids.

SEQ ID NO: 5 shows the polynucleotide sequence that encodes one subunit of α-hemolysin M113R-WT.

SEQ ID NO: 6 shows the amino acid sequence of one subunit of α-hemolysin M113R-WT.

SEQ ID NO: 7 shows the polynucleotide sequence that encodes one subunit of α-hemolysin E111N-WT.

SEQ ID NO: 8 shows the amino acid sequence of one subunit of α-hemolysin E111N-WT.

SEQ ID NO: 9 shows the polynucleotide sequence that encodes one subunit of α-hemolysin A8R-RL2 used in the Example.

SEQ ID NO: 10 shows the amino acid sequence of one subunit of α-hemolysin A8R-RL2 used in the Example.

SEQ ID NO: 11 shows the polynucleotide sequence that encodes one subunit of α-hemolysin M113K-RL2 used in the Example.

SEQ ID NO: 12 shows the amino acid sequence of one subunit of α-hemolysin M113K-RL2 used in the Example.

SEQ ID NO: 13 shows the polynucleotide sequence that encodes one subunit of α-hemolysin M113R-RL2 used in the Example.

SEQ ID NO: 14 shows the amino acid sequence of one subunit of α-hemolysin M113R-RL2 used in the Example.

SEQ ID NO: 15 shows the DNA sequence used in the Example.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an analyte" includes "analytes", reference to "a transmembrane protein pore" includes two or more such pores, reference to "nucleic acid sequence" includes two or more such sequences, and the like.

All publications, patents and patent applications cited herein, whether supra or infra, are hereby incorporated by reference in their entirety.

Method of Enhancing Translocation

The present invention provides a method of enhancing translocation of a charged analyte through a transmembrane protein pore. The transmembrane protein pore is typically for use in detecting the analyte via stochastic sensing. As the analyte translocates through the pore, it typically interacts with the pore and affects the current flowing through the pore in a manner specific for that analyte. A distinctive current flows through the pore whenever the analyte interacts with the pore. This allows the analyte to be detected using stochastic sensing.

The method may enhance the translocation of the analyte in any way. The method preferably (1) increases the frequency of translocation of the analyte through the pore, (2) decreases the threshold voltage for translocation of the analyte through the pore, (3) decreases the speed of translocation of the analyte through the pore or (4) decreases the number of non-translocation interactions between the analyte and the pore. Non-translocation interactions are events where the analyte enters the pore and interacts with the pore, but does not translocate through the pore. In some instance, the non-translocation interactions are eliminated. The method more preferably increases (1) and (2); (1) and (3); (1) and (4); (2) and (3); (2) and (4); (3) and (4); (1), (2) and (3); (1), (3) and (4); (1), (2) and (4); or (2), (3) and (4). The method most preferably increases (1), (2), (3) and (4). In other words, the method most preferably increases the frequency of translocation of the analyte through the pore, decreases the threshold voltage for translocation of the analyte through the pore, decreases the speed of translocation of the analyte through the pore and decreases the number of non-translocation interactions between the analyte and the pore.

It is straightforward for a person skilled in the art to determine whether or not the increase in net opposing charge enhances translocation of the analyte through the pore. For instance, the analyte may be contacted with a non-enhanced or wild-type pore and the same type of pore in which the net opposing charge of its barrel or channel and/or entrance has been increased and any difference in translocation of the analyte between the two pores may be determined. Analyte translocation may be measured using any method known in the art. One method is described in the Examples.

By enhancing translocation of the analyte through the pore, the method of the invention provides an improved pore for stochastic sensing of the analyte. An enhanced translocation through the pore results in a more sensitive system that: (1) allows the detection of the analyte at both high and low concentrations; (2) allows the detection of the analyte even amongst impurities; (3) allows more rapid detection of the analyte; (4) reduces the background noise produced by non-translocation interactions and (5) allows the detection of the analyte at a lower voltage. Most importantly for the sequencing of nucleic acid sequences, an enhanced translocation, and in particular an enhanced frequency of translocation, results in a reduced deadtime between reads of the consecutive nucleotides in the sequence. This allows nucleic acids to be sequenced more quickly. A decreased translocation speed through the pore increases the read time of the consecutive nucleotides in the nucleic acid sequence and so allows the sequence of the nucleic acid to be determined more accurately.

Analyte

The analyte can be any charged substance. An analyte is charged if it has a net charge. The analyte may be negatively charged or positively charged. An analyte is negatively charged if it has a net negative charge. An analyte is positively charged if it has a net positive charge.

Suitable analytes include, but are not limited to, metal ions, inorganic salts, polymers, such as a polymeric acids or bases, dyes, bleaches, pharmaceuticals, diagnostic agents, recreational drugs, explosives and environmental pollutants.

The analyte can be an analyte that is secreted from cells. Alternatively, the analyte can be an analyte that is present inside cells such that the analyte must be extracted from cells.

The analyte is preferably a polymer. The polymer is preferably a nucleic acid sequence. Nucleic acids are negatively charged. A nucleic acid is a macromolecule comprising two or more nucleotides. The nucleic acid handled by the enzyme may comprise any combination of any nucleotides. The nucleotides can be naturally occurring or artificial. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are preferably selected from AMP, TMP, GMP, UMP, dAMP, dTMP, dGMP or dCMP.

The nucleic acid is preferably double stranded, such as DNA. The nucleic acid may be single stranded, such as cDNA or RNA.

The polymer can be a peptide, polypeptide or a protein. The peptide, polypeptide or protein can be naturally-occurring or non-naturally-occurring. The polypeptide or protein can include within it synthetic or modified amino acids. A number of different types of modification to amino acids are well known in the art. For the purposes of the invention, it is to be understood that the analyte can be modified by any method available in the art.

The protein can be an enzyme, antibody, hormone, growth factor or growth regulatory protein, such as a cytokine. The cytokine may be selected from an interleukin, preferably IFN-1, IL-2, IL-4, IL-5, IL-6, IL-10, IL-12 or IL-13, an interferon, preferably IL-γ or other cytokines such as TNF-α. The protein may be a bacterial protein, fungal protein, virus protein or parasite-derived protein. Before it is contacted with the pore, the protein may be unfolded to form a polypeptide chain and thereby allow it to enter the barrel or channel of the pore and interact with the pore.

The analyte may be an amino acid. Charged amino acids are well known in the art and are discussed in more detail below. The amino acid can be naturally-occurring or non-naturally-occurring. The amino acid may be synthetic or modified. A number of different types of modification to amino acids are well known in the art.

The analyte may be an individual nucleotide or a single nucleotide. An individual nucleotide is one which is not bound to another polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide sequence of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. Nucleotides are negatively charged. The nucleotide may be any of those discussed above.

The nucleotide may be derived from the digestion of a nucleic acid sequence such as ribonucleic acid (RNA) or deoxyribonucleic acid. Nucleic acid sequences can be digested using any method known in the art. Suitable methods include, but are not limited to, those using enzymes or catalysts. Catalytic digestion of nucleic acids is disclosed in Deck et al., Inorg. Chem., 2002; 41: 669-677.

Individual nucleotides from a single nucleic acid sequence may be contacted with the pore in a sequential manner in order to sequence the whole or part of the nucleic acid. Sequencing nucleic acids in accordance with the second embodiment of the invention is discussed in more detail below.

The nucleotide is typically unmodified, such as when the nucleotide is derived from the digestion of a nucleic acid sequence. Alternatively, the nucleotide may be modified or damaged. The nucleotide is typically methylated or oxidised. The nucleotide may be labelled with a revealing label. The revealing label may be any suitable label which allows the nucleotide to be detected. Suitable labels include fluorescent molecules, radioisotopes, e.g. $^{125}$I, $^{35}$S, and linkers such as biotin.

The nucleotide is typically present in any suitable biological sample. Suitable biological samples are discussed below.

Transmembrane Protein Pore

A transmembrane protein pore is a polypeptide that permits ions to flow from one side of the membrane to the other along an applied potential. The pore preferably permits the analyte to flow from one side of the membrane to the other along the applied potential.

The pore is typically an oligomer. The pore is preferably made up of several repeating subunits, such as 6, 7 or 8 subunits. The pore is more preferably heptameric. The pore typically comprises a barrel or channel through which the ions may flow. The subunits of the pore typically surround a central axis and contribute strands to a transmembrane β barrel or channel or a transmembrane α-helix bundle or channel.

Pores for use in accordance with the invention can be β-barrel pores or α-helix bundle pores. β-barrel pores comprise a barrel or channel that is formed from β-sheets. Suitable β-barrel pores include, but are not limited to, β-toxins, such as α-hemolysin and leukocidins, and outer membrane proteins/porins of bacteria, such as *Mycobacterium smegmatis* porin A (MspA), outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA.

The most preferred pore for use in the invention is α-hemolysin or a variant thereof. The α-hemolysin pore is formed of seven identical subunits (i.e. it is heptameric). The sequence of one subunit of wild-type α-hemolysin is shown in SEQ ID NO: 2. The sequence of one subunit of α-hemolysin RL2 is shown in SEQ ID NO: 4. A variant is a heptameric pore in which one or more of the seven subunits has an amino acid sequence which varies from that of SEQ ID NO: 2 or 4 and which retains pore activity. A variant may include modifications that facilitate interaction with the analyte.

1, 2, 3, 4, 5, 6 or 7 of the subunits in a variant α-hemolysin may have an amino acid sequence that varies from that of SEQ ID NO: 2 or 4. All seven subunits within a variant pore are typically identical but may be different, particularly if one or more of the subunits has been modified to facilitate interaction with the analyte.

The variant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO: 2 or 4, a subunit of a variant will preferably be at least 50% homologous to that sequence based on amino acid identity. More preferably, the subunit polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 or 4 over the entire sequence. There may be at least 80%, for example at least 85%, 90% or 95%, amino acid identity over a stretch of 200 or more, for example 230, 250, 270 or 280 or more, contiguous amino acids ("hard homology"). Preferred variants are shown in SEQ ID NOs: 6, 8, 10, 12 and 14.

Amino acid substitutions may be made to the amino acid sequence of SEQ ID NO: 2 or 4, for example up to 1, 2, 3, 4, 5, 10, 20 or 30 substitutions. Conservative substitutions may be made, for example, according to Table 1 below.

TABLE 1

Conservative substitutions
Amino acids in the same block in the second column and preferably
in the same line in the third column may be substituted for each other.

| NON-AROMATIC | Non-polar | G A P |
| | | I L V |
| | Polar - uncharged | C S T M |
| | | N Q |
| | Polar - charged | D E |
| | | H K R |
| AROMATIC | | H F W Y |

One or more amino acid residues of the amino acid sequence of SEQ ID NO: 2 or 4 may alternatively or additionally be deleted. Up to 1, 2, 3, 4, 5, 10, 20 or 30 residues may be deleted, or more.

Variants may include subunits made of fragments of SEQ ID NO: 2 or 4. Such fragments retain pore forming activity. Fragments may be at least 50, 100, 200 or 250 amino acids in length. Such fragments may be used to produce chimeric pores. A fragment preferably comprises the pore forming domain of SEQ ID NO: 2 or 4.

Variants include chimeric protein pores comprising fragments or portions of SEQ ID NO: 2 or 4. Chimeric protein pores are formed from subunits each comprising fragments or portions of SEQ ID NO: 2 or 4. The pore or channel part of a chimeric protein pore is typically formed by the fragments or portions of SEQ ID NO: 2 or 4.

One or more amino acids may be alternatively or additionally added to the polypeptides described above. An extension may be provided at the N-terminus or C-terminus of the amino acid sequence of SEQ ID NO: 2 or 4 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention.

As discussed above, a variant of SEQ ID NO: 2 or 4 is a subunit that has an amino acid sequence which varies from that of SEQ ID NO: 2 or 4 and which retains its ability to form a pore. A variant typically contains the regions of SEQ ID NO: 2 or 4 that are responsible for pore formation. The pore forming ability of α-HL, which contains a β-barrel, is provided by β-sheets in each subunit. A variant of SEQ ID NO: 2 or 4 typically comprises the regions in SEQ ID NO: 2 or 4 that form β-sheets. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 of SEQ ID NO: 2 and 4 form β-sheets. One or more modifications can be made to the regions of SEQ ID NO: 2 or 4 that form β-sheets as long as the resulting variant retains its ability to form a pore. Specific modifications that can be made to the β-sheet regions of SEQ ID NO: 2 or 4 in accordance with the invention are discussed below.

A variant of SEQ ID NO: 2 or 4 preferably includes one or more modifications, such as substitutions, additions or deletions, within its α-helices and/or loop regions. Amino acids 2 to 6, 73 to 75, 207 to 209, 214 to 216 and 219 to 222 of SEQ ID NO: 2 and 4 form α-helices. Amino acids 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 of SEQ ID NO: 2 and 4 form loops. Amino acids 1 and 294 are terminal amino acids. Specific modifications that can be made to the loop regions of SEQ ID NO: 2 or 4 in accordance with the invention are discussed below.

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A transmembrane protein pore may be modified for example by the addition of histidine or aspartic acid residues to assist their identification or purification or by the addition of a signal sequence to promote their secretion from a cell where the polypeptide does not naturally contain such a sequence.

A pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

The pore may be derived from a pore producing organism, such as *Staphylococcus aureus*, or made synthetically or by recombinant means. For example, the pore may be synthesized by in vitro transcription and translation (IVTT). In addition to the modifications discussed in detail below that increase the opposing charge of the barrel or channel and/or entrance of the pore, the amino acid sequence of the pore may be modified to include non-naturally occurring amino acids, for instance to increase the stability of the pore. When the pore is produced by synthetic means, such amino acids may be introduced during production. Methods for including non-naturally-occurring amino acids in the pore are well known in the art and are discussed in more detail below with reference to increasing the net opposing charge.

The pore may also be produced using D-amino acids. For instance, the pore may comprise a mixture of L-amino acids and D-amino acids. This is conventional in the art for producing such proteins or peptides.

The pore can also be altered following either synthetic or recombinant production. The pore may contain other non-specific modifications as long as they do not interfere with translocation of the analyte. A number of non-specific side chain modifications are well known in the art and may be made to the side chains of the pore. Such modifications include, for example, reductive alkylation of amino acids by reaction with an aldehyde followed by reduction with NaBH$_4$, amidination with methylacetimidate and thiol-specific modifications using ethyleneamine.

The pore can be produced using standard methods known in the art. Polynucleotide sequences encoding a pore or a pore subunit may be derived and replicated using standard methods in the art. Such sequences are discussed in more detail below. Polynucleotide sequences encoding a pore or a pore subunit may be expressed in a bacterial host cell using standard techniques in the art. The pore or pore subunit may be produced in a cell by in situ expression of the polypeptide from a recombinant expression vector. The expression vector optionally carries an inducible promoter to control the expression of the polypeptide.

A pore subunit may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system. The naturally occurring or recombinantly-produced pore or pore subunit may then be inserted into a naturally occurring or artificial membrane for use in accordance with the invention. Methods for inserting pore into membranes are discussed below.

The transmembrane pore may comprise a molecular adaptor, such as a cyclodextrin, a cyclic peptide or a cucurbituril, that facilitates the interaction between the pore and the analyte by improving the host-guest chemistry of the pore and the analyte. Suitable adaptors are well known in the art. The molecular adaptor may be covalently attached to the pore.

Increasing the Net Opposing Charge

The method of the invention comprises increasing the net opposing charge of the barrel or channel and/or entrance of the pore. The opposing charge is the opposite charge to the charge of the analyte. If the analyte is negatively charged, the method involves increasing the net positive charge of the barrel or channel and/or entrance of the pore. If the analyte is positively charged, the method comprises increasing the net negative charge of the barrel or channel and/or entrance of the pore. The net opposing charge may be increased by any means known in the art.

The net opposing charge is increased in a manner that does not interfere with translocation of the analyte through the pore. The net opposing charge is increased in a manner that does not interfere with the interaction between the analyte and the pore.

In a preferred embodiment, the analyte is negatively charged and the method involves increasing the net positive charge of the barrel or channel and/or entrance of the pore. The net positive charge is preferably increased by introducing one or more positively charged amino acids into the barrel or channel and/or entrance of the pore. The one or more positively charged amino acids may be introduced by addition. The one or more positively charged amino acids are preferably introduced by substitution.

A positively charged amino acid is an amino acid with a net positive charge. The positively charged amino acid(s) can be naturally-occurring or non-naturally-occurring. The positively charged amino acids may be synthetic or modified. For instance, modified amino acids with a net positive charge may be specifically designed for use in the invention. A number of different types of modification to amino acids are well known in the art.

Preferred naturally-occurring positively charged amino acids include, but are not limited to, histidine (H), lysine (K) and arginine (R). Any number and combination of H, K and/or R may be introduced into the barrel or channel and/or entrance of the pore.

Methods for adding or substituting naturally-occurring amino acids are well known in the art. For instance, methionine (M) may be substituted with arginine (R) by replacing the codon for methionine (ATG) with a codon for arginine (AGA) at the relevant position in a polynucleotide encoding the pore. The polynucleotide can then be expressed as discussed below.

Methods for adding or substituting non-naturally-occurring amino acids are also well known in the art. For instance, non-naturally-occurring amino acids may be introduced by including synthetic aminoacyl-tRNAs in the IVTT system used to express the pore. Alternatively, they may be introduced by expressing the pore in E. coli that are auxotrophic for specific amino acids in the presence of synthetic (i.e. non-naturally-occurring) analogues of those specific amino acids. They may also be produced by naked ligation if the pore is produced using partial peptide synthesis.

Any amino acid may be substituted with a positively charged amino acid. One or more uncharged amino acids, non-polar amino acids and/or aromatic amino acids may be substituted with one or more positively charged amino acids. Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Preferably, one or more negatively charged amino acids are substituted with one or more positively charged amino acids. Suitable negatively charged amino acids include, but are not limited to, aspartic acid (D) and glutamic acid (E).

Preferred introductions include, but are not limited to, substitution of M with R, substitution of M with H, substitution of M with K, substitution of D with R, substitution of D with H, substitution of D with K, substitution of E with R, substitution of E with H, substitution of E with K, substitution of N with R, substitution of T with R and substitution of G with R.

Any number of positively charged amino acids may be introduced. For instance, 1, 2, 5, 10, 15, 20, 25 or more positively charged amino acids may be introduced. If the pore is oligomeric, the one or more positively charged amino acids may be introduced into one, some or all of the subunits of the pore. In the case of α-HL (i.e. SEQ ID NO: 2 and 4 and variants thereof discussed above), the one or more positively charged amino acids may be introduced into 1, 2, 3, 4, 5, 6 or 7 of the subunits in the pore. In each of the seven subunits, the one or more positively charged amino acids may be introduced at the same or different positions. Preferably, the pore is a homoheptamer and one or more positive amino acids are introduced at the same position(s) in each subunit.

The net positive charge may also be increased by replacing by substitution one or more negatively charged amino acids with one or more uncharged amino acids, non-polar amino acids and/or aromatic amino acids. The removal of negative charge from the barrel or channel and/or entrance increases the net positive charge. The uncharged amino acids, non-polar amino acids and/or aromatic amino acids can be naturally-occurring or non-naturally-occurring. They may be synthetic or modified. Suitable uncharged amino acids, non-polar amino acids and aromatic amino acids are discussed above. Preferred substitutions include, but are not limited to, substitution of E with N, substitution of D with N, substitution of E with T, substitution of D with T, substitution of E with G and substitution of D with G.

Any number and combination of uncharged amino acids, non-polar amino acids and/or aromatic amino acids may substituted into the barrel or channel and/or entrance. For instance, 1, 2, 5, 10, 15, 20, 25 or more uncharged amino acids, non-polar amino acids and/or aromatic amino acids may be may substituted into the barrel or channel and/or entrance. If the pore is oligomeric, the uncharged amino acids, non-polar amino acids and/or aromatic amino acids may be substituted into one, some or all of the subunits of the pore. In the case of α-HL, (i.e. SEQ ID NO: 2 and 4 and variants thereof discussed above), the uncharged amino acids, non-polar amino acids and/or aromatic amino acids may be substituted into 1, 2, 3, 4, 5, 6 or 7 of the subunits in the pore. In each of the seven subunits, the one or more uncharged amino acids, non-polar amino acids and/or aromatic amino acids may be substituted into the same or different positions. Preferably, the pore is a homoheptamer and uncharged amino acids, non-polar amino acids and/or aromatic amino acids are substituted into the same position(s) in each subunit. Negatively charged amino acids may be substituted with (1) uncharged amino acids; (2) non-polar amino acids; (3) aromatic amino acids; (4) uncharged amino acids and non-polar amino acids; (5)

uncharged amino acids and aromatic amino acids; and (5) non-polar amino acids and aromatic amino acids; or (6) uncharged amino acids, non-polar amino acids and aromatic amino acids.

In another embodiment, the analyte is positively charged and the method involves increasing the net negative charge of the barrel or channel and/or entrance of the pore. The net negative charge is preferably increased by introducing one or more negatively charged amino acids into the barrel or channel and/or entrance of the pore. The one or more negatively charged amino acids may be introduced by addition. The one or more negatively charged amino acids are preferably introduced by substitution. Methods for adding and substituting amino acids are well known in the art.

Suitable negatively charged amino acids are discussed above. The negatively charged amino acid(s) can be naturally-occurring or non-naturally-occurring. The negatively charged amino acids may be synthetic or modified.

Any amino acid may be substituted with a negatively charged amino acid. One or more uncharged amino acids, non-polar amino acids and/or aromatic amino acids may be substituted with one or more negatively charged amino acids. Preferably, one or more positively charged amino acids are substituted with one or more negatively charged amino acids. Any number of negatively charged amino acids may be introduced as discussed above.

The net negative charge may also be increased by replacing by substitution one or more positively charged amino acids with one or more uncharged amino acids, non-polar amino acids and/or aromatic amino acids. A preferred substitution is substitution of K with N. The removal of positive charge from the barrel or channel and/or entrance increases the net negative charge. The uncharged amino acids, non-polar amino acids and/or aromatic amino acids can be naturally-occurring or non-naturally-occurring. They may be synthetic or modified.

Any number and combination of uncharged amino acids, non-polar amino acids and/or aromatic amino acids may substituted into the barrel or channel and/or entrance as discussed above.

Barrel or Channel and/or Entrance

In one embodiment, the net opposing charge of the barrel or channel of the pore is increased. The barrel or the channel of the pore is the portion of the pore through which ions travel through the pore across the membrane. The analyte also translocates through the barrel or the channel. The barrel or channel may be formed from α-helices or β-strands depending on the type of pore. Preferably, the net opposing charge of the lumen of the barrel or channel is increased.

As described above, the net opposing charge is increased by introducing or replacing by substitution one or more amino acids. Amino acid(s) may be introduced or substituted at any position in the barrel or channel as long as translocation of the analyte is enhanced. Amino acid(s) are preferably introduced or substituted at position(s) that form part of the lumen of the barrel or channel. In other words, it is preferred that amino acid(s) are not introduced or substituted at positions in the barrel or channel that are buried in the pore or hidden from the lumen.

Amino acid(s) are preferably introduced or substituted towards the end of the barrel or channel through which the analyte enters. The end of the pore through which the analyte enters may be the cis end or the trans end. The end is preferably the cis end. Amino acid(s) are preferably introduced or substituted near a constriction of the barrel or channel. Amino acid(s) are more preferably introduced or substituted near a constriction of the lumen of the barrel or channel.

In another embodiment, the net opposing charge of the entrance of the pore is increased. An entrance of the pore is the portion of the pore through which the analyte enters into the barrel or channel. Entrances are typically formed primarily from loop regions in the pore.

As described above, the net opposing charge is increased by introducing or replacing by substitution one or more amino acids. Amino acid(s) may be introduced or substituted at any position in the entrance as long as translocation of the analyte is enhanced. Preferably, amino acid(s) are introduced or substituted at position(s) that form part of the lumen of the entrance. In other words, it is preferred that amino acid(s) are not introduced or substituted at positions in the entrance that are buried in the pore or hidden from the lumen.

Amino acid(s) may be introduced or substituted in one or both entrances. Amino acid(s) are typically introduced or substituted near the entrance through which the analyte enters the pore. Amino acid(s) may be introduced or substituted in the barrel or channel and in one or both entrance(s).

In SEQ ID NOs: 2 and 4, amino acid(s) may be introduced or substituted at any of positions 1 to 22, 35 to 41, 54 to 59, 100 to 155 and 218 to 229 to increase the net opposing charge. All of these positions form part of the lumen of the barrel or channel or part of the lumen of an entrance of SEQ ID NOs: 2 and 4. Positions 111 to 147 form part of the lumen of the barrel or channel. Positions 1 to 22, 35 to 41, 54 to 59, 100 to 110, 148 to 155 and 218 to 229 form part of the lumen of an entrance. Amino acid(s) are preferably introduced or substituted at positions of SEQ ID NO: 2 or 4 located near the constriction of the barrel or channel. Such positions include, but are not limited to, positions 111, 113, 115, 117, 119, 121, 123, 125, 127, 145 and 147. A preferred position in the entrance of SEQ ID NO: 2 is position 8.

Preferred substitutions located near the constriction of the barrel or channel of SEQ ID NO: 2 or 4 include, but are not limited to, M113R, E111N, M113K, T115R, T117R, G119R, N121R, N123R, M113D, K147N, D127R, T125R and T145R. Preferred substitutions located in the entrance of SEQ ID NO: 4 include, but are not limited to, A8R and A8K.

Transmembrane Protein Pore of the Invention

The present invention also provides a transmembrane protein pore enhanced in accordance with the invention. Such a pore will have an increased net opposing charge in its barrel or channel and/or entrance. An increased net positive charge enhances translocation of a negatively charged analyte through the pore. An increased net negative charge enhances translocation of a positively charged analyte through the pore. The pore may be enhanced using any method described above.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. Alternatively, a pore of the invention may be present in a lipid bilayer.

A pore of the invention may be present as an individual or single pore. Alternatively, a pore of the invention may be present in a homologus or heterologous population of two or more pores.

The transmembrane pore preferably comprises at least one subunit comprising SEQ ID NO: 6, 8, 10 or a variant thereof. The transmembrane pore is more preferably a homoheptamer comprising seven subunits comprising SEQ ID NO: 6, 8 or 10 or a variant thereof. Variants of SEQ ID NO: 6, 8 and 10 may differ from SEQ ID NO: 6, 8 and 10 to the same extent discussed above for variants of SEQ ID NOs: 2 and 4.

Variants of SEQ ID NO: 6 must comprise arginine at position 113 (M113R). The variant of SEQ ID NO: 6 is preferably not M113R-RL2 (SEQ ID NO: 14). Variants of SEQ ID NO: 8 must comprise asparagine at position 111 (E111N). Variants of SEQ ID NO: 10 must comprise arginine at position 8 (A8R-RL2).

Polynucleotide

The present invention also provides a polynucleotide sequence which encodes a transmembrane protein pore of the invention. The polynucleotide will encode a pore having an increased net opposing charge in its barrel or channel and/or entrance. An increased net positive charge enhances translocation of a negatively charged analyte through the pore. An increased net negative charge enhances translocation of a positively charged analyte through the pore. The pore may be enhanced using any method described above.

The present invention also provides a polynucleotide sequence encoding a transmembrane protein pore subunit having the sequence of SEQ ID NO: 6, 8 or 10 or a variant thereof. The polynucleotide sequence preferably comprises the sequence shown in SEQ ID NO: 5, 7 or 9 or a variant thereof. A variant of SEQ ID NO: 5, 7 or 9 is a sequence at least 50%, 60%, 70%, 80%, 90% or 95% homologous based on nucleotide identity to sequence of SEQ ID NO: 5, 7 or 9 over the entire sequence. There may be at least 80%, for example at least 85%, 90% or 95% nucleotide identity over a stretch of 600 or more, for example 700, 750, 850 or 900 or more, contiguous nucleotides ("hard homogly"). Homology may be calculated as described above. The variant may comprise a sequence that differs from SEQ ID NO: 5, 7 or 9 on the basis of the degeneracy of the genetic, code.

A variant of SEQ ID NO: 5 must encode a pore subunit comprising an arginine at position 113 (M113R) of SEQ ID NO: 6 or at the position equivalent to position 113 (M113R) of SEQ ID NO: 6. A variant of SEQ ID NO: 5 preferably does not encode M113R-RL2 (SEQ ID NO: 14).

A variant of SEQ ID NO: 7 must encode a pore subunit comprising asparagine at position 111 (E111N) of SEQ ID NO: 8 or at the position equivalent to position 111 (E111N) of SEQ ID NO: 8.

A variant of SEQ ID NO: 9 must encode a pore subunit comprising arginine at the position 8 (A8R) of SEQ ID NO: 10 or at the position equivalent to position 8 (A8R) of SEQ ID NO: 10.

Polynucleotide sequences may be derived and replicated using standard methods in the art. Chromosomal DNA may be extracted from a pore producing organism, such as Staphylococcus aureus. The gene encoding the pore subunit may be amplified using PCR involving specific primers. The amplified sequence may then be incorporated into a recombinant replicable vector such as a cloning vector. The vector may be used to replicate the polynucleotide in a compatible host cell. Thus polynucleotide sequences encoding a pore subunit may be made by introducing a polynucleotide encoding a pore subunit into a replicable vector, introducing the vector into a compatible host cell, and growing the host cell under conditions which bring about replication of the vector. The vector may be recovered from the host cell. Suitable host cells for cloning of polynucleotides encoding a pore subunit are well known in the art and described in more detail below.

The polynucleotide sequence encoding a pore subunit may be cloned into suitable expression vector. In an expression vector, the polynucleotide sequence encoding a pore subunit is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different pore subunit sequences may be introduced into the vector.

The expression vector may then be introduced into a suitable host cell. Thus, a pore subunit can be produced by inserting a polynucleotide sequence encoding a pore subunit into an expression vector, introducing the vector into a compatible bacterial host cell, and growing the host cell under conditions which bring about expression of the polynucleotide sequence encoding the pore subunit. The recombinantly-expressed pore subunit may self-assemble into a pore in the host cell membrane. Alternatively, the recombinant pore produced in this manner may be removed from the host cell and inserted into another membrane. When producing a heptameic pore comprising at least two different subunits, the different subunits may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the pore subunit at a high level. Host cells transformed with a polynucleotide sequence encoding a pore subunit will be chosen to be compatible with the expression vector used to transform the cell. The host cell is typically bacterial and preferably Escherichia coli. Any cell with a λ DE3 lysogen, for example C41 (DE3), BL21 (DE3), JM109 (DE3), B834 (DE3), TUNER, Origami and Origami B, can express a vector comprising the T7 promoter.

Method of Detecting Analytes

The present invention also relates to a method of determining the presence or absence of an analyte in a sample. The analyte is charged. The analyte may be any of those discussed above. The method comprises (1) contacting the sample with a transmembrane protein pore of the invention under conditions that allow the analyte, if present, to translocate through and interact with the pore and (2) measuring the current passing through the pore during the interaction and thereby determining the presence or absence of the analyte. Any transmembrane protein pore of the invention can be used. The benefits associated with using a transmembrane protein pore of the invention to detect an analyte are discussed above. In a preferred embodiment, the method further comprises enhancing translocation of the analyte through the pore as described above. The enhancement is of course carried out before the analyte is detected.

The analyte is present if the current flows through the pore in a manner specific for the analyte (i.e. if a distinctive current associated with the analyte is detected flowing through the pore). The analyte is absent if the current does not flow through the pore in a manner specific for the analyte.

The invention therefore involves stochastic sensing of an analyte. The invention can be used to differentiate analytes of similar structure on the basis of the different effects they have on the current passing through a transmembrane protein pore. The invention can also be used to measure the concentration of a particular analyte in a sample.

The invention may also be used in a sensor that uses many or thousands of pores of the invention in bulk sensing applications.

The method may be carried out using any suitable membrane/pore system in which a transmembrane protein pore of the invention is inserted into a membrane. The method is typically carried out using (i) an artificial membrane comprising a transmembrane protein pore of the invention, (ii) an isolated, naturally-occurring membrane comprising a transmembrane protein pore of the invention, or (iii) a cell expressing a transmembrane protein pore that has been modified in accordance with the invention. The method is preferably carried out using an artificial membrane. The membrane may comprise other transmembrane and/or intramembrane proteins as well as other molecules in addition to the transmembrane protein pore of the invention.

The method of the invention is typically carried out in vitro.

Membrane

The membrane forms a barrier to the flow of ions, nucleotides and nucleic acids. The membrane is preferably a lipid bilayer. Lipid bilayers suitable for use in accordance with the invention can be made using methods known in the art. For example, lipid bilayer membranes can be formed using the method of Montal and Mueller (1972). Lipid bilayers can also be formed using the method described in International Application No. PCT/GB08/000563.

The method of the invention may be carried out using lipid bilayers formed from any membrane lipid including, but not limited to, phospholipids, glycolipids, cholesterol and mixtures thereof. Any of the lipids described in International Application No. PCT/GB08/000563 may be used.

Methods are known in the art for inserting pores into membranes, such as lipid bilayers. For example, the pore may be suspended in a purified form in a solution containing a lipid bilayer such that it diffuses to the lipid bilayer and is inserted by binding to the lipid bilayer and assembling into a functional state. Alternatively, the pore may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

The method of the invention is typically carried out in vitro.

Interaction Between the Pore and Analyte

The analyte may be contacted with the pore on either side of the membrane. The analyte may be introduced to the pore on either side of the membrane. The analyte may be contacted with the side of the membrane that allows the analyte to pass through the pore to the other side of the membrane. For example, the analyte is contacted with an end of the pore, which in its native environment allows the entry of ions or small molecules, such as analytes, into the barrel or channel of the pore such that the analyte may pass through the pore. In such cases, the analyte interacts with the pore as it passes across the membrane through the barrel or channel of the pore. Alternatively, the analyte may be contacted with the side of the membrane that allows the analyte to interact with the pore, dissociate from the pore and remain on the same side of the membrane.

The analyte may interact with the pore in any manner and at any site. The analyte may reversibly bind to the pore.

During the interaction between the analyte and the pore, the analyte affects the current flowing through the pore in a manner specific for that analyte. For example, a particular analyte will reduce the current flowing through the pore for a particular mean time period and to a particular extent. In other words, the current flowing through the pore is distinctive for a particular analyte. Control experiments may be carried out to determine the effect a particular analyte has on the current flowing through the pore. Results from carrying out the method of the invention on a test sample can then be compared with those derived from such a control experiment in order to identify a particular analyte in the sample or determine whether a particular analyte is present in the sample. The frequency at which the current flowing through the pore is affected in a manner indicative of a particular analyte can be used to determine the concentration of that analyte in the sample.

Apparatus

The method may be carried out using any apparatus that is suitable for investigating a membrane/pore system in which a transmembrane protein pore is inserted into a membrane. The method may be carried out using any apparatus that is suitable for stochastic sensing. For example, the apparatus comprises a chamber comprising an aqueous solution and a barrier that separates the chamber into two sections. The barrier has an aperture in which the membrane containing the pore is formed. The analyte may be contacted with the pore by introducing the analyte into the chamber. The analyte may be introduced into either of the two sections of the chamber.

The method may be carried out using the apparatus described in International Application No. PCT/GB08/000562.

The method of the invention involves measuring the current passing through the pore during interaction with the analyte. Therefore the apparatus also comprises an electrical circuit capable of applying a potential and measuring an electrical signal across the membrane and pore. The method may be carried out using a patch clamp or a voltage clamp. The method preferably involves the use of a voltage clamp. The Example discloses one way to carry out a voltage clamp method.

Sample

The analyte is present in any suitable sample. The invention is typically carried out on a sample that is known to contain or suspected to contain the analyte. The invention may be carried out on a sample that contains one or more analytes whose identity is unknown. Alternatively, the invention may be carried out on a sample to confirm the identity of one or more analytes whose presence in the sample is known or expected.

The sample may be a biological sample. The invention may be carried out in vitro on a sample obtained from or extracted from any organism or microorganism. The organism or microorganism is typically prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Conditions

The method of the invention involves the measuring of a current passing through the pore during interaction with the analyte. Suitable conditions for measuring ionic currents through transmembrane protein pores are well known in the art and disclosed in the Example. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 120 mV to 170 mV. Enhancing translocation of the analyte through the pore in accordance with the invention allows lower voltages to be used.

The method is carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. The salt concentration is preferably from 150 to 500 mM. High salt concentrations provide a high signal to noise ratio and allow for currents indicative of the presence of a analyte to be identified against the background of normal current fluctuations. Lower salt concentrations must be used if analyte detection is carried out in the presence of an enzyme, such as when sequencing nucleic acids. The salt concentration is preferably from 150 to 500 mM. Good nucleotide discrimination at these low salt concentrations can be achieved by carrying out the method at temperatures above room temperature, such as from 30° C. to 40° C.

The method is typically carried out in the presence of a buffer. In the exemplary apparatus discussed above, the buffer is present in the aqueous solution in the chamber. Any buffer may be used in the method of the invention. One suitable buffer is Tris-HCl buffer. The method is typically carried out at a pH of from 4.0 to 10.0, from 4.5 to 9.5, from 5.0 to 9.0, from 5.5 to 8.8, from 6.0 to 8.7 or from 7.0 to 8.8 or 7.5 to 8.5. The pH used is preferably about 7.5.

The method is typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The method may be carried out at room temperature. The method is preferably carried out at a temperature that supports enzyme function, such as about 37° C. Good analyte discrimination can be achieved at low salt concentrations if the temperature is increased.

In addition to increasing the solution temperature, there are a number of other strategies that can be employed to increase the conductance of the solution, while maintaining conditions that are suitable for enzyme activity, for example when sequencing nucleic acids. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

Method of Sequencing Nucleic Acids

The present invention also relates to a method of sequencing a target nucleic acid sequence. The method comprises (a) pushing or pulling the target sequence through a transmembrane pore of the invention so that a proportion of the nucleotides in the target sequence interacts with the pore and (b) measuring the current passing through the pore during each interaction and thereby determining the sequence of the target sequence. Hence, the method involves stochastic sensing of a proportion of the nucleotides in a target nucleic acid sequence as the nucleotides pass through the barrel or channel in a successive manner in order to sequence the target sequence.

Any pore of the invention may be used. A pore of the invention in which the net positive charge of the barrel or channel and/or entrance has been increased is particularly suited to this method. For instance, the enhanced translocation of the negatively charged nucleic acid through the pore reduces the non-translocation events and deadtime between reads of each nucleotide in the sequence and/or increases the read time for each nucleotide in the sequence. In a preferred embodiment, the method further comprises enhancing translocation of the analyte through the pore as described above. The enhancement is of course carried out before the nucleic acid is sequenced.

The whole or only part of the target nucleic acid sequence may be sequenced using this method. The nucleic acid sequence can be any length. For example, the nucleic acid sequence can be at least 10, at least 50, at least 100, at least 150, at least 200, at least 250, at least 300, at least 400 or at least 500 nucleotides in length. The nucleic acid sequence is preferably DNA or RNA. The nucleic acid sequence can be naturally occurring or artificial. For instance, the method may be used to verify the sequence of a manufactured oligonucleotide. The method is typically carried out in vitro.

The method may be carried out using any of the samples, membrane/pore systems and conditions discussed above.

Interaction Between the Pore and Nucleotides

The nucleic acid may be contacted with the pore on either side of the membrane. The nucleic acid may be introduced to the pore on either side of the membrane. The nucleotide or nucleic acid is typically contacted with the side of the membrane on which an enzyme is attached to the pore. This allows the enzyme to handle the nucleic acid during the method as discussed below.

A proportion of the nucleotides of the target nucleic acid sequence interact with the pore as it passes across the membrane through the barrel or channel of the pore.

The nucleotides may interact with the pore in any manner and at any site. As discussed above, the nucleotides preferably reversibly bind to the pore.

During the interaction between the nucleotides and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide.

Pushing or Pulling the Nucleic Acid Through the Pore

Strand sequencing in accordance with the invention involves the controlled and stepwise translocation of nucleic acid polymers through a pore. The nucleic acid may be pushed or pulled through the pore in any manner known to a person skilled in the art. For instance, the nucleic acid could be pushed or pulled through the pore using an electroosmotic effect. The nucleic acid is preferably pushed or pulled through the pore using a DNA handling enzyme.

The majority of nucleic acid handling enzymes are suitable for use in this application provided they hydrolyse, polymerise or process single stranded nucleic acids, such as DNA or RNA. Preferred enzymes that are capable of pushing or pulling the target nucleic acid sequence through the pore include polymerases, exonucleases, helicases and topoisomerases, such as gyrases. The polymerase is preferably a member of any of the Enzyme Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The helicase is preferably a member of any of the Enzyme Classification (EC) groups 3.6.1.- and 2.7.7.-. The helicase is preferably an ATP-dependent DNA helicase (EC group 3.6.1.8), an ATP-dependent RNA helicase (EC group 3.6.1.8) or an ATP-independent RNA helicase. The topoisomerase is preferably a member of any of the Enzyme Classification (EC) groups 5.99.1.2 and 5.99.1.3.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore with an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Kit

The present invention also relates to a kit that may be used to carry out the method of sequencing a target nucleic acid sequence. The kit is therefore suitable for sequencing nucleic acids. The kit comprises a transmembrane pore of the invention and a nucleic acid handling enzyme. The pore and the enzyme may be any of those discussed above.

The kit may additionally comprise one or more other reagents or instruments which enable any of the embodiments of the method mentioned above to be carried out. Such reagents or instruments include one or more of the following: suitable buffer(s) (aqueous solutions), means to obtain a sample from a subject (such as a vessel or an instrument comprising a needle), means to amplify nucleic acid sequences as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Examples illustrate the invention:

Example 1

Here, by augmenting the internal positive charge within the α-hemolysin pore and altering its distribution, we increase the capture rate of a 92-nt single-stranded DNA by ~10-fold over the wild-type pore at +120 mV and dramatically lower the voltage threshold at which the DNA is translocated through the pore, e.g. by 50 mV for 1 event $s^{-1}$ $mM^{-1}$. Further, events in which DNA enters the pore, but is not translocated, are almost eliminated. These engineered nanopores provide a basis for improved nucleic acid analysis and may assist in implementing ultrarapid nanopore sequencing.

1. Materials and Methods 1.1 Protein Preparation

α-HL was produced as described elsewhere (Cheley S, Braha O, Lu X, Conlan S, Bayley H: A functional protein pore with a "retro" transmembrane domain. *Protein Sci.* 1999, 8:1257-1267). The sequence of one subunit of α-HL is shown in SEQ ID NO: 2. In short, the protein was expressed in the presence of [$^{35}$S]methionine in an *E. coli* in vitro transcription and translation (IVTT) system (*E. coli* T7 S30 Extract System for Circular DNA, Cat. # L1130, Promega, Madison, Wis.). IVTT reactions (100 μl) containing α-HL monomers were incubated with rabbit red blood cell membranes for 1 h at 37° C. The solution was spun at 25,000×g and the pellet containing α-HL heptamers was loaded onto a 5% SDS-polyacrylamide gel. The gel was run for 4 h at 100 V and vacuum dried for 3 to 4 h without heating onto Whatman 3M filter paper. The dried gel was exposed to photographic film for 2 h and the developed film was used to locate the position of the heptameric protein in the gel. This region of the gel was cut out, rehydrated and crushed in 400 μL of 10 mM Tris.HCl, pH 8.0, containing 100 μM EDTA. After 20 min at room temperature, the polyacrylamide was removed by centrifuging the suspension at 25,000×g for 7 min at room temperature through a cellulose micro spin column (Microfilterfuge tubes, Cat. #7016-024, Rainin, Oakland, Calif.). Aliquots of the purified protein were stored at −80° C.

Mutants α-HL genes were prepared either by using a site-directed mutagenesis kit (QuickChange® II XL, Cat. #200522-5, Stratagene, Cedar Creek, Tex.) or by cassette mutagenesis (Cheley S, Gu L-Q, Bayley H: Stochastic sensing of nanomolar inositol 1,4,5-trisphosphate with an engineered pore. *Chem. Biol.* 2002, 9:829-838). The RL2 gene encodes four amino acid replacements in the barrel domain (Val-124→Leu, Gly-130→Ser, Asn-139→Gln, Ile-142→Leu) and one in the amino latch region of the pore (Lys-8→Ala). The sequence of one subunit of α-HL-RL2 is shown in SEQ ID NO: 4. The DNA sequence of each new gene was verified.

1.2 Planar Bilayer Recordings

A bilayer of 1,2-diphytanoyl-sn-glycero-3-phosphocholine (Avanti Polar Lipids) was formed on an aperture (~100 μm in diameter) in a 25-μm thick polytetrafluoroethylene film (Goodfellow Cambridge Limited, Cat. no. FP301200/10, Huntingdon, UK) that divided a chamber into cis and trans compartments. Both compartments contained 0.4 mL of 1 M KCl, 25 mM Tris.HCl, pH 8, containing 100 μM EDTA. Planar bilayer current recordings were performed with a patch clamp amplifier (Axopatch 200B, Axon Instruments, Foster City, Calif.). The protein and subsequently the DNA were added to the cis compartment, which was connected to ground. The DNA was prepared and PAGE-purified by Sigma Genosys, UK. The concentration of the DNA was determined by measuring the absorbance at 260 nm of the solution in the cis chamber at the end of each experiment. The DNA sequence was: 5'-AAAAAAAAAAAAAAAAAAAAAATTC-CCCCCCCCCCCCCCCCCCCTTAAAAAAAAAATT CCCCCCCCCTTAAAAAAAAAATTCCCCCCCCCC-3' (SEQ ID NO: 15).

At applied potentials above +120 mV, the amplified signal arising from the ionic current passing through the α-HL pore was low-pass filtered at 50 kHz and sampled at 250 kHz with a computer equipped with a Digidata 1440A digitizer (Molecular Devices, Sunnyvale, Calif.). At applied potentials of +100 mV and +80 mV the signal was filtered at 40 kHz, while at +60 mV and +40 mV the signal was filtered at 30 kHz and 20 kHz, respectively. The sampling rate was at least five times the filtering rate. The data used in Table 2 were analyzed with pClamp 10.1 software (Axon Instruments), by using three different current levels. Level 0 corresponded to the open channel current, level 1 to the mid-amplitude event current and level 2 to the low-amplitude event current. The assignment to each level was checked manually.

TABLE 2

Distribution of the types of event as a percentage of the total. The error is the standard error of the mean for four (WT, E111N-WT and M113R-WT) or five (M113R-RL2 and RL2) experiments.

| | Type A | Type B | Type C | Type D | Type E |
|---|---|---|---|---|---|
| WT | 67.6 ± 2.9 | 19.6 ± 2.7 | 10.2 ± 1.2 | 2.0 ± 0.5 | 0.6 ± 0.3 |
| M113R-WT | 94.1 ± 1.7 | 1.2 ± 0.3 | 3.3 ± 1.2 | 1.4 ± 0.2 | 0 |
| E111N-WT | 97.5 ± 0.5 | 0.6 ± 0.1 | 1.1 ± 0.4 | 0.8 ± 0.2 | 0 |
| RL2 | 84.0 ± 3.2 | 7.3 ± 2.3 | 4.8 ± 0.7 | 3.5 ± 0.7 | 0.4 ± 0.2 |
| M113R-RL2 | 91.4 ± 1.3 | 1.7 ± 0.5 | 4.1 ± 0.8 | 2.6 ± 0.2 | 0.2 ± 0.1 |

Figure 2:
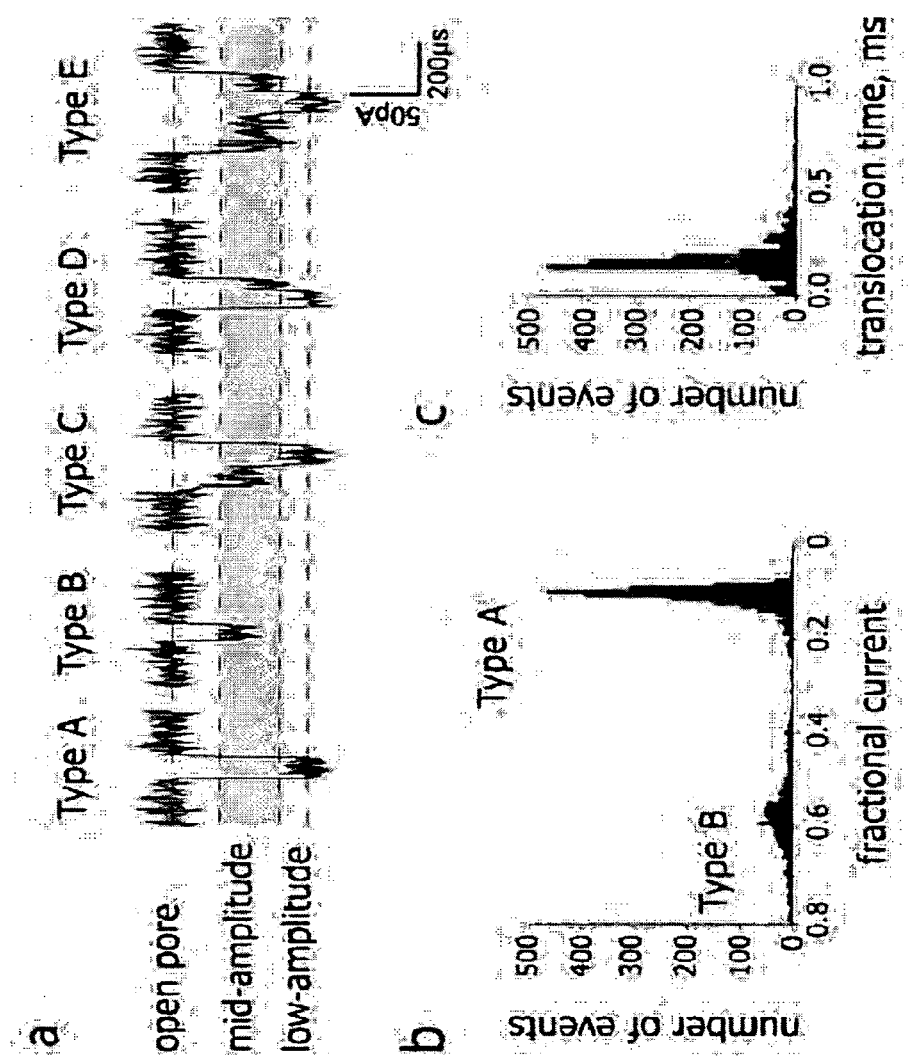
FIG. 2 shows DNA translocation through the α-HL pore at +120 mV. (a) The five types of interaction of DNA with the WT α-HL pore. Type A event: a simple low-amplitude event (interpreted as the passage of DNA straight through the pore); type B: a simple mid-amplitude event (DNA is captured in the vestibule and exits the pore from the side of entry, the cis side); type C: a mid-amplitude signal, followed by a low-amplitude signal within the same event (DNA is detained in the vestibule before it passes through the β barrel to exit at the trans side); type D: a low-amplitude signal, followed by a mid-amplitude signal within the same event (DNA enters the β barrel directly and then retracts into the vestibule to exit the pore from the cis side); type E: a mid-amplitude signal, followed by a low-amplitude signal, followed by a second mid-amplitude signal within the same event (DNA explores the vestibule, threads into the β barrel, but retracts back into the vestibule and exits the pore from cis side). (b) Events histogram showing mean residual currents for 2,500 events expressed as fractions of the open pore current through the WT α-HL pore. The peaks representing type A and type B events are labelled. The type C, D and E events, characterized by their mean event currents, appear between the two major peaks. (c) Histogram of the DNA translocation times for the type A events. DNA (0.95 μM) was presented from the cis chamber in 1 M KCl, 100 μM EDTA, 25 mM Tris.HCl at pH 8.0.

The data used in FIG. 2b were analyzed and prepared for presentation by using only two levels: level 0 was set to the open channel current, and level 1 was placed between the mid-amplitude and low-amplitude event currents. The frequency of DNA translocations was calculated by fitting the interevent intervals to a single exponential (logarithmic binning, 10 bin/decade) and normalizing the mean value of the duration to a DNA concentration of 1 μM. The DNA translocation time was calculated from the peak of a histogram of the distribution of the translocation times (Meller A, Nivon L, Brandin E, Golovchenko J, Branton D: Rapid nanopore discrimination between single polynucleotide molecules. *Proc. Natl. Acad. Sci. USA* 2000, 97:1079-1084).

1.3 Curve Fitting

The values of $f_{max}$, b and $V_0$ (Table 3) were determined by fitting the voltage dependence of the frequency of DNA translocation for the WT and mutated α-HL nanopores to equation 1 (FIG. 5) by using Origin data analysis software (OriginLab, Northampton, Mass.). The errors in these values are expressed as standard errors. The curve fittings were adjusted for the experimental error of each point by using the instrumental weight.

TABLE 3

Values of '$f_{max}$', 'b' and '$V_0$' for various α-HL pores. The values were derived by fitting the data to equation 1 (see Methods). Additional conditions are described in the legend to FIG. 2.

| | $f_{max}$ | b | $V_0$ | $V_1{}^a$ |
|---|---|---|---|---|
| M113R-WT | 7,300 ± 2,200 | 1200 ± 100 | −90 ± 7 | 45 |
| E111N-WT | 1,600 ± 200 | 780 ± 40 | −56 ± 3 | 50 |
| M113R-RL2 | 990 ± 300 | 990 ± 90 | −67 ± 7 | 77 |
| WT | 300 ± 60 | 420 ± 40 | 25 ± 6 | 100 |
| RL2 | 300 ± 150 | 980 ± 130 | 20 ± 17 | 151 |

2. Results and Discussion 2.1 Electrical Recording of DNA Translocation Through the WT α-HL Nanopore Single-channel electrical recordings in planar lipid bilayers were carried out in 1 M KCl, 25 mM Tris.HCl at pH 8.0, containing 100 μM EDTA. Under these conditions, the WT α-HL pore had a unitary conductance of 1.04±0.01 nS (+120 mV, n=23). After the addition of a 92-nucleotide synthetic ssDNA to the cis compartment (0.5 to 2.5 μM), the current through a single pore was interrupted by short-lived blockades owing to the translocation of the ssDNA (Kasianowicz J J, Brandin E, Branton D, Deamer D W: Characterization of individual polynucleotide molecules using a membrane channel. *Proc. Natl. Acad. Sci. USA* 1996, 93:13770-13773). At +120 mV, the interactions of the DNA molecules with the WT nanopore produced five different current patterns (type A, B, C, D and E) that are combinations of three conductance levels: the open state, a mid-amplitude state and a low-amplitude state (FIG. 2a) (Butler T Z, Gundlach J H, Troll M A: Determination of RNA orientation during translocation through a biological nanopore. *Biophys J* 2006, 90:190-199). Events with a duration of shorter than 10 μs were judged to represent the transient interaction of DNA with the mouth of the pore and were ignored in our analysis. As substantiated below, in all five types of event, DNA is captured by the pore, but only in type A and C events is the DNA translocated through the pore, from the cis to the trans side.

In a histogram displaying the mean current associated with each event (FIG. 2b), the current levels are separated into two peaks centered at 0.11 times (low amplitude) and 0.58 times (mid amplitude) the open-pore current. The type A events characterized by a fractional current of 0.11 (FIG. 2b) had a most likely duration of 0.14±0.01 ms (n=7) as determined from the peak of a Gaussian fit to a histogram of the event durations (FIG. 2c) (Meller A, Nivon L, Brandin E, Golovchenko J, Branton D: Rapid nanopore discrimination between single polynucleotide molecules. *Proc. Natl. Acad. Sci. USA* 2000, 97:1079-1084). The peak in the events histogram at a fractional current of 0.58 comprises type B current blockades, which show a mid-state current level only (FIG. 2b). Type C, D and E events contain both mid-amplitude and low-amplitude current levels. Type C events corresponded to 10% of the total number of events, type D events 2% of the total and type E events, which displayed a mid-low-mid pattern, were only 0.6% of the total. The type C, D and E events are scattered between the two main peaks in the histogram, reflecting their wide distribution of mean currents.

2.2 DNA Interactions with Engineered Nanopores

We made a variety of homoheptameric α-HL pores in which the charge distribution within the lumen was altered. The pores examined were homoheptamers, so the mutations appear in all seven subunits, e.g. M113R has a ring of seven positively charged side chains at position 113. The mutants were made by using the WT or RL2 genes as templates. The RL2 gene encodes four amino acid replacements in the barrel domain (Val-124→Leu, Gly-130→Ser, Asn-139→Gln, Ile-142→Leu) and one in the cis entrance of the pore (Lys-8→Ala). The properties of the mutants differed significantly from the WT pore with respect to the open-pore current and the frequency of occurrence of DNA translocation events (Table 4).

TABLE 4

DNA translocation through the αHL nanopore. τ is the most probable translocation time; f is the frequency of translocation (type A and C events) normalized to 1 μM DNA; $I_B$ is the fractional residual current during a type A event and $I_{+120mV}$ is the open-pore current at +120 mV. The errors are expressed as the standard error of the mean and the number of experiments is in parentheses. For $I_B$ the errors were all within ±0.01.

| | τ (ms) | f ($s^{-1} \mu M^{-1}$) | $I_B$ | $I_{+120mV}$ (pA) |
|---|---|---|---|---|
| WT | 0.141 ± 0.004 (n = 6) | 3.0 ± 0.2 (n = 12) | 0.11 (n = 7) | 125 ± 1 (n = 23) |
| RL2 | 0.147 ± 0.003 (n = 4) | 0.28 ± 0.04 (n = 5) | 0.10 (n = 4) | 124 ± 2 (n = 16) |
| A8R-RL2 | 0.15 ± 0.01 (n = 7) | 7.6 ± 0.7 (n = 5) | 0.10 (n = 7) | 125 ± 3 (n = 10) |
| A8K-RL2 | 0.16 ± 0.03 (n = 3) | 3.0 ± 0.3 (n = 3) | 0.11 (n = 3) | 123 ± 3 (n = 7) |
| M113R-WT | 0.138 ± 0.003 (n = 5) | 23 ± 2 (n = 9) | 0.04 (n = 5) | 140 ± 2 (n = 13) |
| E111N-WT | 0.28 ± 0.04 (n = 10) | 18 ± 1 (n = 9) | 0.11 (n = 10) | 137 ± 3 (n = 15) |
| M113K-RL2 | 0.092 ± 0.002 (n = 3) | 4.0 ± 0.3 (n = 3) | 0.05 (n = 3) | 129 ± 2 (n = 10) |
| M113R-RL2 | 0.141 ± 0.004 (n = 4) | 4.4 ± 0.6 (n = 7) | 0.03 (n = 5) | 131 ± 2 (n = 18) |
| T115R-RL2 | 0.23 ± 0.02 (n = 3) | 2.2 ± 0.1 (n = 7) | 0.02 (n = 3) | 122 ± 2 (n = 16) |
| T117R-RL2 | 0.35 ± 0.04 (n = 8) | 1.6 ± 0.1 (n = 7) | 0.03 (n = 4) | 113 ± 6 (n = 9) |
| G119R-RL2 | 0.292 ± 0.002 (n = 4) | 1.3 ± 0.1 (n = 7) | 0.02 (n = 4) | 111 ± 1 (n = 8) |
| N121R-RL2 | 0.30 ± 0.01 (n = 9) | 0.43 ± 0.03 (n = 10) | 0.03 (n = 6) | 96 ± 2 (n = 13) |
| N123R-RL2 | 0.22 ± 0.02 (n = 5) | 0.43 ± 0.04 (n = 8) | 0.03 (n = 4) | 77 ± 2 (n = 10) |
| M113D-RL2 | not observed (n = 3) | not observed (n = 3) | not observed (n = 3) | 112 ± 3 (n = 3) |

The homoheptamers formed from M113R-WT (seven subunits of SEQ ID NO: 6) and E111N-WT (seven subunits of SEQ ID NO: 8) showed the largest increases in ionic current at +120 mV with respect to the WT pore (11% and 9%, respectively), while N123R-RL2 showed the largest current decrease (38%, Table 4). After the addition of DNA to the cis chamber at +120 mV, current blockades were observed for all the mutants tested except for M113D-RL2, in which case the addition of 2 μM DNA did not produce any blockades at up to +300 mV (n=3).

Figure 7:
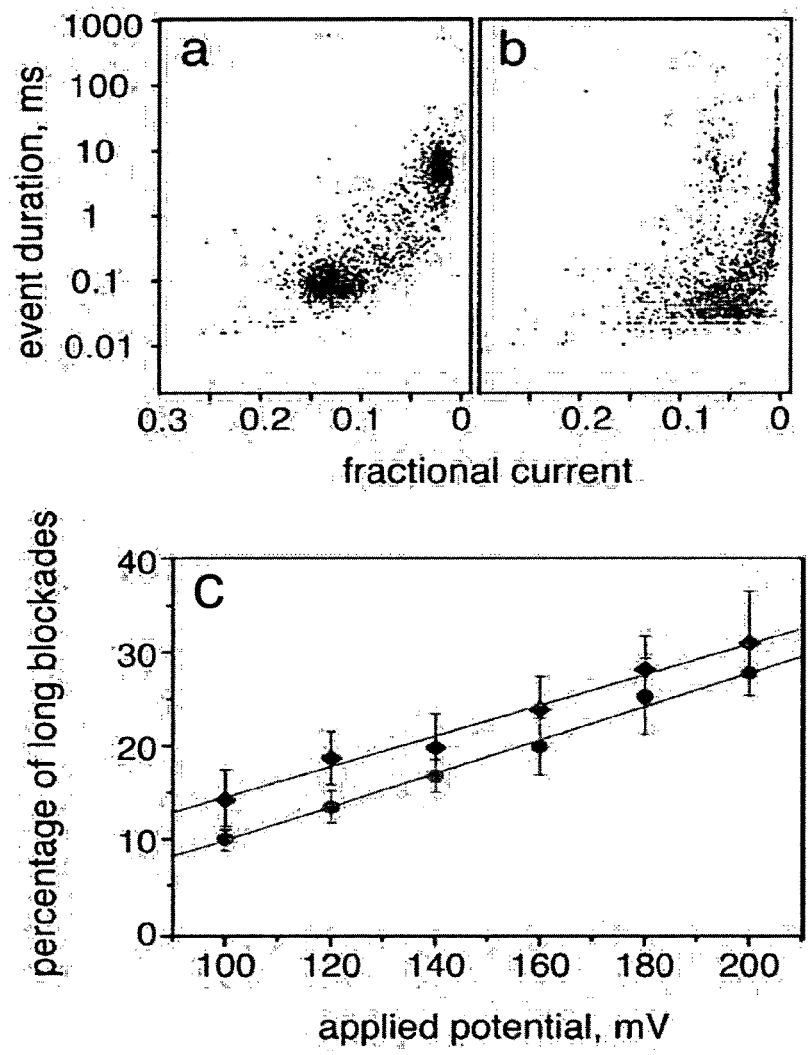
FIG. 7 shows DNA blockades for the homoheptameric mutant α-HL pores E111N-WT and M113R-WT. (a) Currents through E111N-WT during DNA-induced blockades at +200 mV, expressed as a fraction of the open-pore current, versus the event duration displayed on a semilogarithmic scale. (b) Corresponding plot for M113R-WT. (c) Long blockades for E111N-WT (diamonds) and M113R-WT (circles) as a percentage of the total for applied potentials from +100 to +200 mV. The DNA was added to the cis chamber at ~0.5 μM; the exact concentration was determined after each experiment. For further conditions, see FIG. 2, legend.

The distribution of the five types of interaction of DNA with the nanopore (FIG. 2a) depended on the mutant (see also FIG. 7). For pores other than WT, RL2, A8R-RL2 and A8K-RL2, the numbers of captures without translocation were negligible and therefore the term "translocation" is used henceforth. Nevertheless, in all cases, the number of type A and type C events was used to determine the frequency of DNA translocation.

Substitution of Lys-8 with an amino acid with a neutral side chain (mutant RL2) increased the relative proportion of type A events (84% versus 68% in WT) and decreased the type B and C events (7% and 5% in RL2, respectively, compared to 20% and 10% in WT). The elimination of the charge at the central constriction or the addition of a positive charge to the interior of the β barrel also increased the percentage of the type A events, and again the type B and C events were less well represented by comparison with the WT pore (Table 2). Recordings from E111N-WT, M113R-WT and M113R-RL2 (seven subunits of SEQ ID NO: 14) showed more than 90% of type A events (98%, 94% and 91%, respectively) and less than 6% of type B and C events (2%, 5% and 6%, respectively). The fraction of the minor type D and E events was similar in WT, RL2 and M113R-RL2, but lower in M113R-WT and E111N-RL2 (Table 2).

The translocation times of DNA through the α-HL nanopores were not changed considerably by the point mutations. The mutant with the slowest mean translocation time was N117R-RL2 at 0.35±0.04 ms, which is only twice the mean translocation time observed for the WT pore (Table 4). The various mutants showed different extents of current block during the translocation of DNA through the pore (as determined from the type A events or the lowest level of type C events). WT, RL2, A8K-RL2 and E111N-WT showed fractional residual currents of 0.10 of the open channel current, while the introduction of positive charges in the β barrel produced higher extents of block (Table 4).

2.3 Effects of Point Mutations on the DNA Capture Rate

Figure 3:
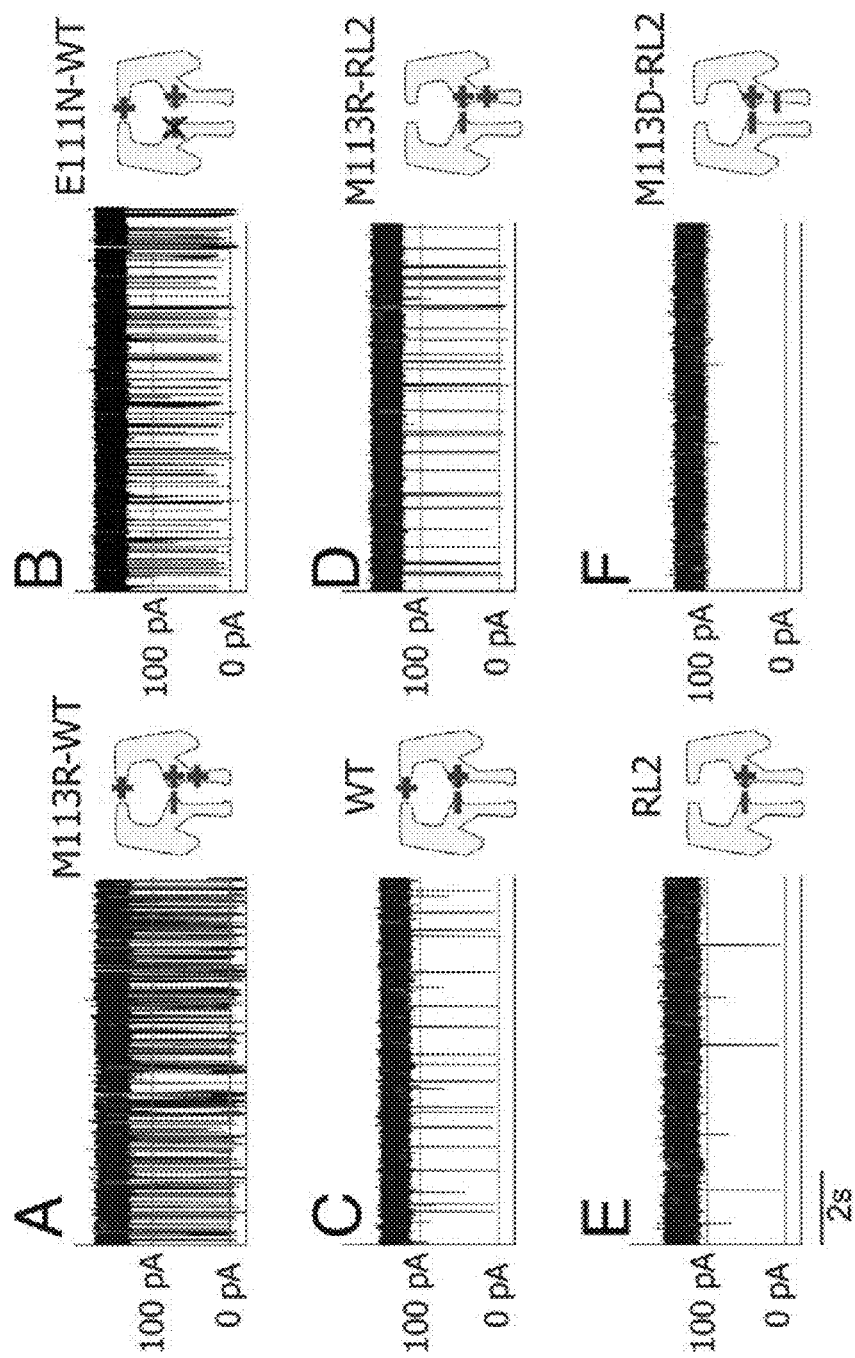
FIG. 3 shows the effects of charged side-chains, introduced or removed by mutagenesis, on the frequency of DNA translocation at +120 mV. (a) M113R-WT (0.46 μM DNA, cis), (b) E111N-WT (0.47 μM), (c) WT (0.53 μM), (d) M113R-RL2 (0.74 μM), (e) RL2 (0.60 μM) and (f) M113D-RL2 (2.0 μM). M113D-RL2 showed no current blockades at up to +300 mV. Additional conditions are described in the legend to FIG. 2.
Figure 8:
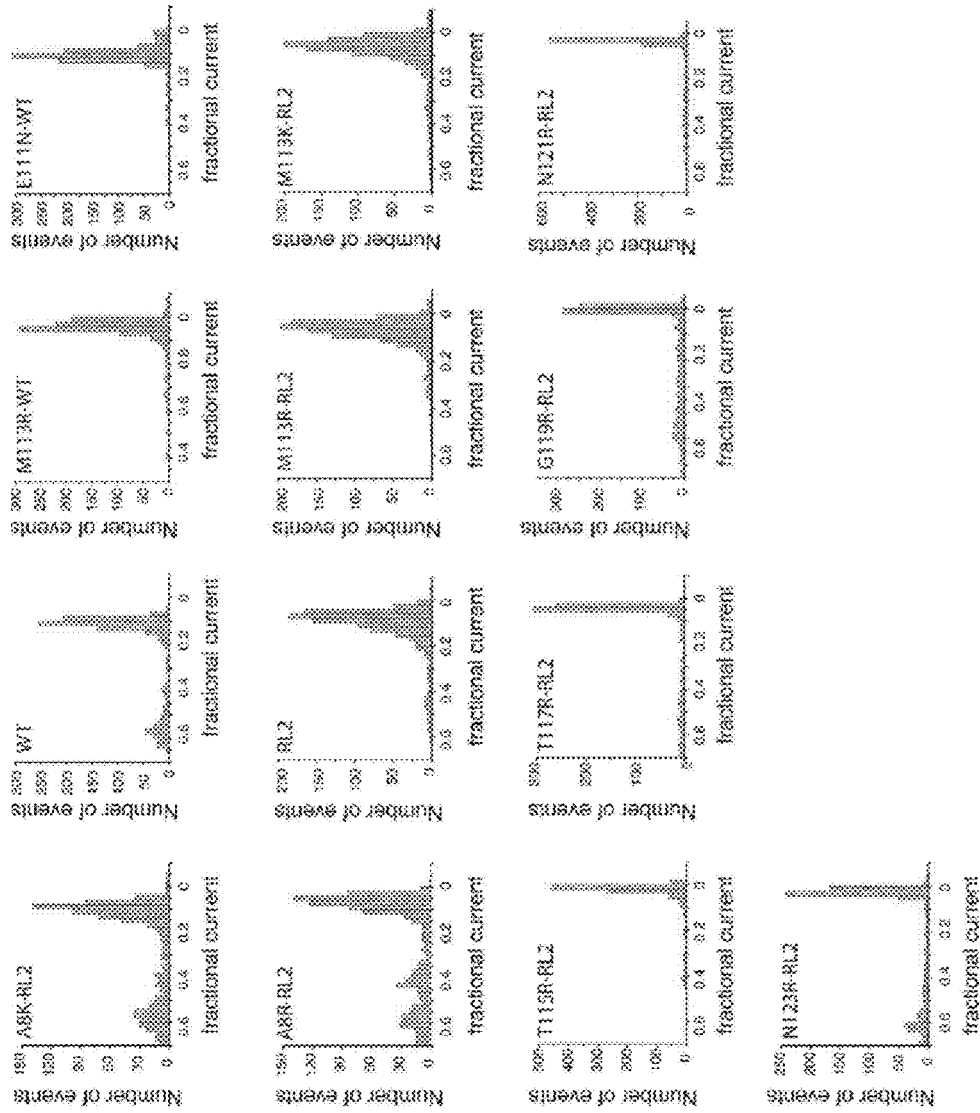
FIG. 8 shows amplitude histograms of mean event currents for DNA blockades of various α-HL pores. The main peak represents the type A events (DNA translocation). Each plot comprises 1000 events. The conditions are described in the legend to FIG. 2.

The effects of charged amino acid side chains on the passage of DNA through the α-HL pore were examined at +120 mV (FIG. 3). Lys-8 is the charged residue in the closest proximity to entering DNA. The substitution of Lys-8 with Ala (in the mutant RL2) decreased the number of translocation events per unit time by almost an order of magnitude, while substitution with Arg (in A8R-RL2 i.e. seven subunits of SEQ ID NO: 10) produced a three-fold increase in the translocation rate (Table 4). The additional mutations in RL2 (with respect to WT) did not affect DNA translocation, as confirmed by reintroducing Lys-8 into the RL2 background (A8K-RL2, Table 4 and FIG. 8).

Removal of the positive charge from the cis entrance of the pore combined with the introduction of a positive charge just below the constriction restored (M113K-RL2 i.e. seven subunits of SEQ ID NO: 12) or even slightly enhanced (M113R-RL2) the frequency of translocation (FIG. 3 and Table 4). The effect of charge is cumulative as showed by the ten-fold increase in translocation frequency of M113R-WT compared to WT and the increase of two orders of magnitude when M113R-WT is compared to RL2 (FIG. 3 and Table 4). By contrast with the effects of positive charge, the placement of negative charge just below the constriction (M113D-RL2) eliminated DNA translocation at all potentials tested (+100 to +300 mV). In accord with these findings, removal of the negative charge at the constriction (E111N-WT) increased the frequency of translocation six-fold.

Figure 4:
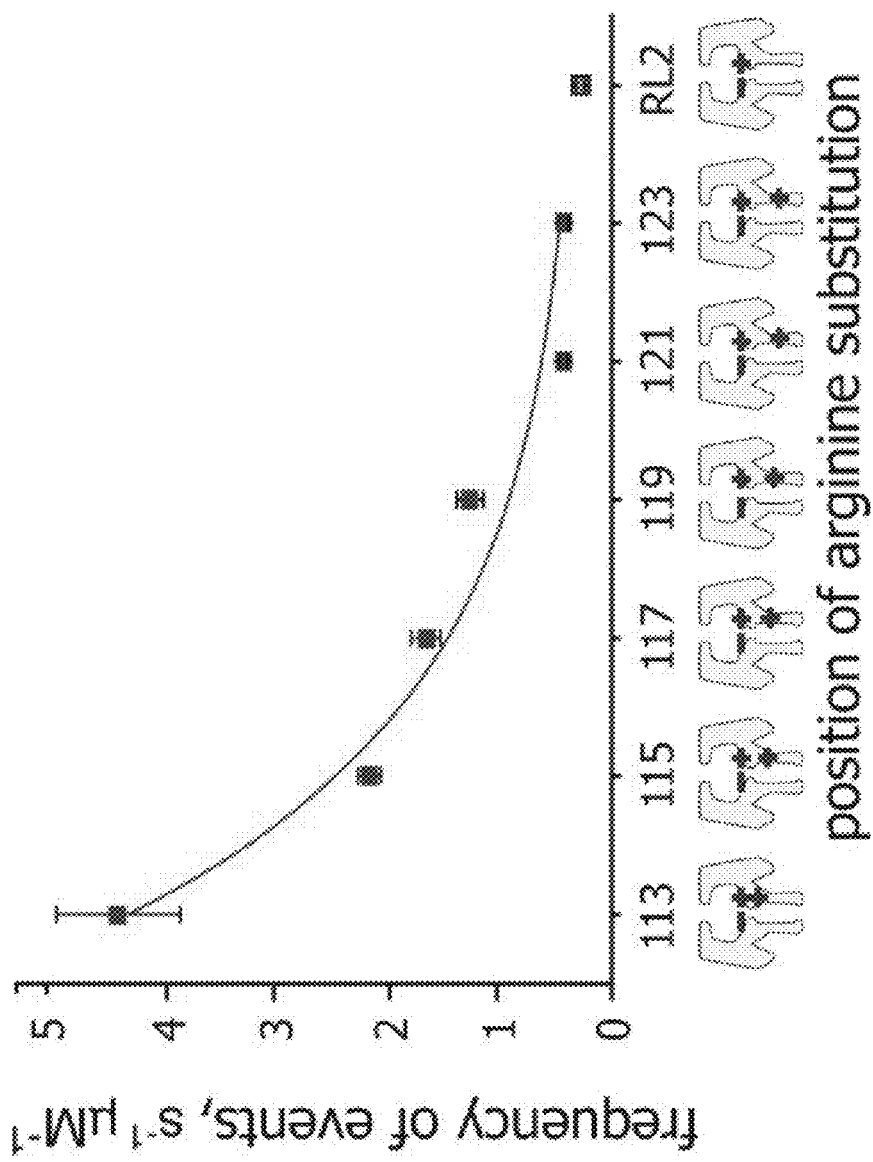
FIG. 4 shows the effects of arginine substitution in the β barrel of α-HL on the frequency of DNA translocation through the pore +120 mV. The frequency of DNA translocation is normalized to 1 μM DNA. The line is a single exponential fit of the frequency of DNA translocation versus the distance of the arginine substitution from the constriction as represented by residue number. The mutants are in the RL2 background. Additional conditions are described in the legend to FIG. 2.
Figure 9:
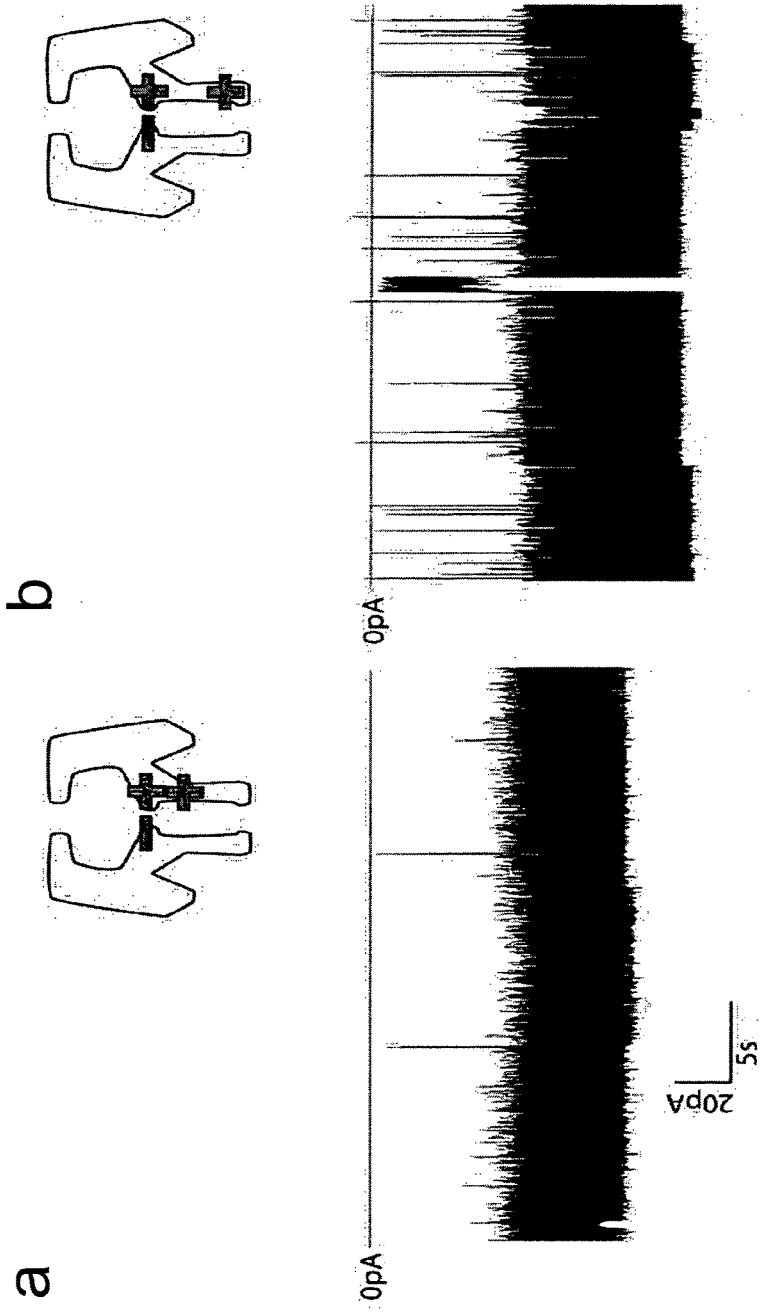
FIG. 9 shows current blockades after DNA addition (1.0 μM) to the trans chamber for: (a) M113R-RL2 and (b) N121R-RL2. The applied potential was −120 mV. For these mutants the currents through the open pores are much noisier at negative potentials than at positive potentials. Further conditions are described in the legend to FIG. 2.

Amino acid substitutions within the β barrel of α-HL also affected the frequency of DNA translocation. Individual replacements of the amino acids at positions 111, 113, 115, 117, 119, 121 and 123 with Arg (in the RL2 background) produced α-HL pores that showed a progressive decrease in the translocation frequency as the Arg residue became located further from the cis entrance (FIG. 4 and Table 4). By contrast, when DNA was added to the trans side of the protein, the effect was reversed; the translocation of DNA molecules through the pore was enhanced by a ring of arginines close to the trans entrance when compared with one near the constriction site (FIG. 9).

Figure 5:
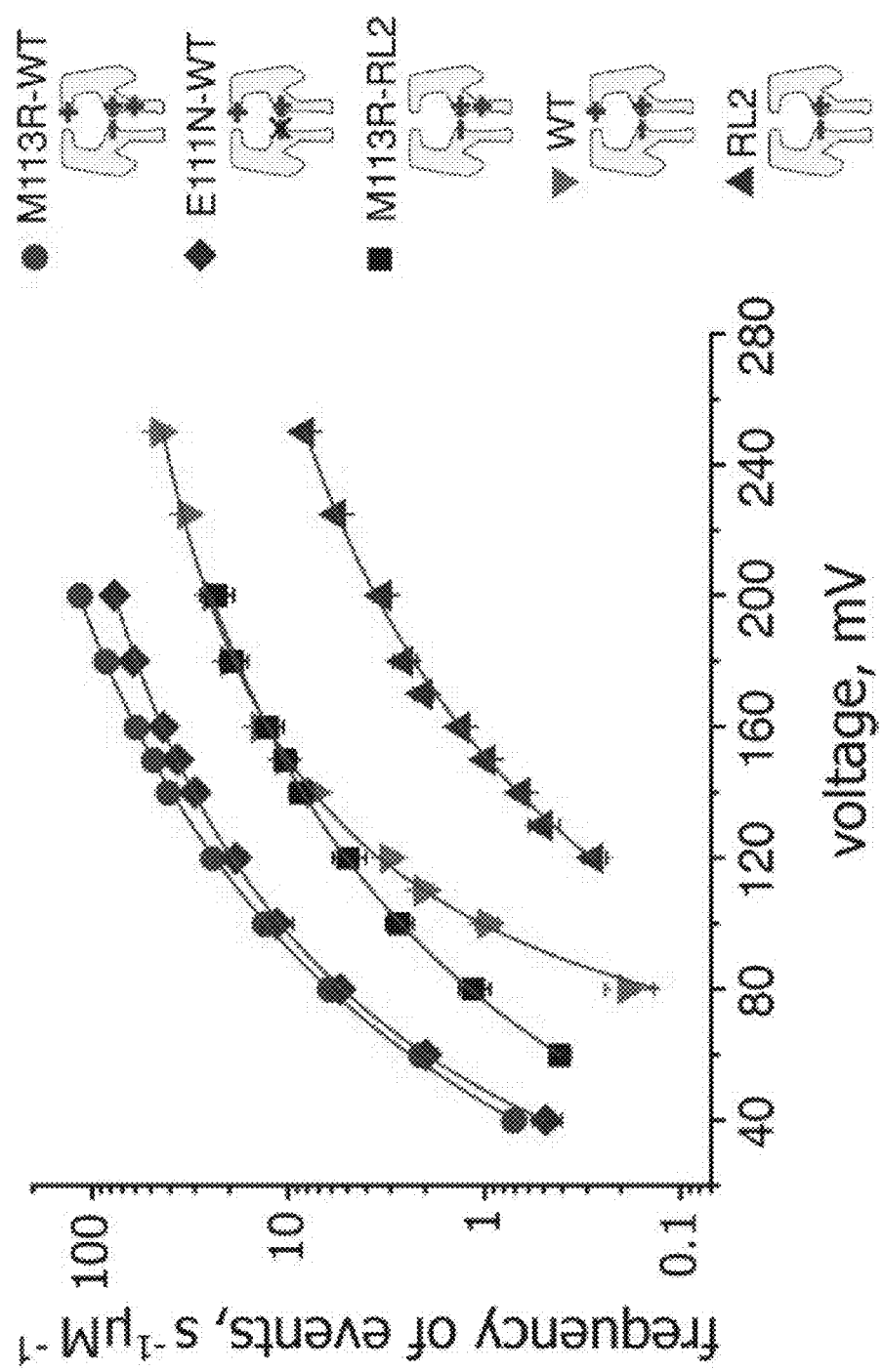
FIG. 5 shows the voltage dependence of the DNA capture rates. The DNA translocation frequency is plotted on a logarithmic scale and normalized to 1 μM DNA. Only the translocation events (i.e. type A and C) are included in the analysis. M113R-WT (red circles), E111N-WT (blue diamonds), M113R-RL2 (black squares), WT (green triangles down) and RL2 (blue triangles up). The lines show fits of the data with equation 1.

2.4 Voltage Dependence of DNA Translocation and Reduction of the Voltage Threshold for Translocation We found that the frequency of DNA translocation f(V) was described well by:

$$f(V) = f_{max} e^{\frac{b}{V_0 - V}} \text{ for } V > V_0, \quad (1)$$

where '$f_{max}$' is the rate of DNA translocation at a hypothetical infinite applied potential, '$V_0$' is the threshold for DNA translocation, and a larger value of 'b' gives a faster approach to '$f_{max}$' (FIG. 5). More positive charge produced pores with a greatly reduced threshold and a steeper approach to $f_{max}$ (Table 3). Further, pores with no additional charge at the constriction had lower values of $f_{max}$ (300±60 s$^{-1}$ μM$^{-1}$ and 300±150 s$^{-1}$ μM$^{-1}$ for WT and RL2, respectively), while additional positive charge at both the constriction and the cis entrance gave high values of $f_{max}$ (7,300±2,200 s$^{-1}$ μM$^{-1}$ and 1,600±200 s$^{-1}$ μM$^{-1}$ for M113R-WT and E111N-WT, respectively). A pore formed with a ring of additional charge at the constriction, but no charge at the cis entrance (M113R-RL2), displayed an intermediate value of $f_{max}$ (990±300 s$^{-1}$ μM$^{-1}$).

2.5 Dwell-Time/Amplitude Distributions of the Events for M113R-WT and E111N-WT

Dwell-time/amplitude distributions of the events for the M113R-WT and E111N-WT homoheptamers (but not the other mutants) yielded two distinct clusters of current blockades at 100 to 200 mV (FIG. 7). The relative intensities of the two peaks in the distributions were voltage dependent, with the longer events increasing with the applied potential (FIG. 7c). The first peak comprised blockades with a fast translocation time and a fractional residual current at +120 mV of 0.96 for M113R-WT and 0.89 for E111N-WT. The second cluster of current blockades included events with a longer dwell time and almost full current block. It is unlikely that the two clusters can be accounted for by 5' versus 3' threading (Mathe J, Aksimentiev A, Nelson D R, Schulten K, Meller A: Orientation discrimination of single-stranded DNA inside the alpha-hemolysin membrane channel. *Proc Natl Acad Sci USA* 2005, 102:12377-12382), because the differences in dwell times are too great (~100-fold).

In this study, the blockades at +120 mV are considered. At this potential, the short-lived events dominate in the dwell-time/amplitude distributions for M113R-WT and E111N-WT and it is these events, which are predominantly type A (Table 2), that are considered. To determine the frequency of DNA translocation both short and long events were included, but the contribution of the latter is minor.

2.6 Assignment of Intermediate V

The assignment of intermediate V is supported by the findings of Kasianowicz and co-workers, who showed that, under a positive applied potential, the cis addition of ssDNA produces short lived current blockades of 85-100% of the open pore current. PCR analysis of the trans chamber revealed that DNA had passed through the α-HL nanopore (Kasianowicz J J, Brandin E, Branton D, Deamer D W: Characterization of individual polynucleotide molecules using a membrane channel. *Proc. Natl. Acad. Sci. USA* 1996, 93:13770-13773).

Further, Movileanu and colleagues observed that individual PEG molecules covalently attached inside the β barrel produce a much higher reduction of the open pore current (70%) than when they are attached within the vestibule (20%) (Movileanu L, Cheley S, Howorka S, Braha O, Bayley H: Location of a constriction in the lumen of a transmembrane pore by targeted covalent attachment of polymer molecules. *J. Gen. Physiol.* 2001, 117:239-251).

Howorka and Bayley found that DNA duplexes covalently attached near the cis entrance with overhangs that protrude into the β barrel produce a current reduction of ~90% of the open pore current (Howorka S, Bayley H: Probing distance and electrical potential within a protein pore with tethered DNA. *Biophys. J.* 2002, 83:3202-3210). Finally, DNA immobilized inside the β barrel as part of a DNA-α-HL rotaxane structure causes a 85% block of the pore current (Sánchez-Quesada J, Saghatelian A, Cheley S, Bayley H, Ghadiri M R: Single molecule DNA rotaxanes of a transmembrane pore protein. *Angew. Chem. Int. Ed Engl.* 2004, 43:3063-3067).

2.7 Assignment of the Mid-Level Events

Occupancy of the vestibule is associated with a reduced conductance (but not to the extent caused by occupancy of the barrel). For example, when high molecular weight PEG molecules (Movileanu L, Cheley S, Howorka S, Braha O, Bayley H: Location of a constriction in the lumen of a transmembrane pore by targeted covalent attachment of polymer molecules. *J. Gen. Physiol.* 2001, 117:239-251) or PAMAM dendrimers with a hydrodynamic diameter of 4.1 nm (Martin H, Kinns H, Mitchell N, Astier Y, Madathil R, Howorka S: Nanoscale protein pores modified with PAMAM dendrimers. *J Am Chem Soc* 2007, 129:9640-9649) are tethered within the vestibule, the current is reduced by 20% and 45%, respectively. Second, when DNA duplexes are tethered within the vestibule, a 38% reduction of the pore current is observed (Howorka S, Bayley H: Probing distance and electrical potential within a protein pore with tethered DNA. *Biophys. J.* 2002, 83:3202-3210). Finally, when the α-HL pore was genetically engineered so that the vestibule was filled with flexible polypeptides chains, the current was reduced by up to 70%, the reduction depending on the number of amino acids inserted (Jung Y, Cheley S, Braha O, Bayley H: The internal cavity of the staphylococcal α-hemolysin pore accommodates ~175 exogenous amino acid residues. *Biochemistry* 2005, 44:8919-8929).

2.8 Discussion

We have enhanced the frequency of translocation of DNA molecules by the αHL pore by using site-directed mutagenesis. The introduction or removal of charged groups within the lumen had a profound effect on DNA translocation. Increasing the positive charge near the internal constriction increased the DNA translocation frequency at +120 mV by almost an order of magnitude (FIG. 3), and greatly decreased the threshold voltage for DNA translocation (FIG. 5). By contrast, eliminating the positive charge at the cis entrance decreased the frequency of DNA translocation by ten-fold. The effect of charge at the constriction on the DNA translocation frequency is surprising, as the cis entrance of the pore is 5 nm away and under the experimental conditions of 1 M KCl the Debye length is 0.3 nm. Therefore, charged residues at the constriction are not expected to affect the capture of DNA through electrostatic interactions that extend into the bulk solution. Rather some form of "action at a distance" must be proposed, the most likely being rapid, reversible sampling of the lumen of the pore by DNA from the cis compartment or electroosmosis, both of which are discussed here.

A Scheme for the Interaction of DNA with the α-HL Pore

Figure 6:
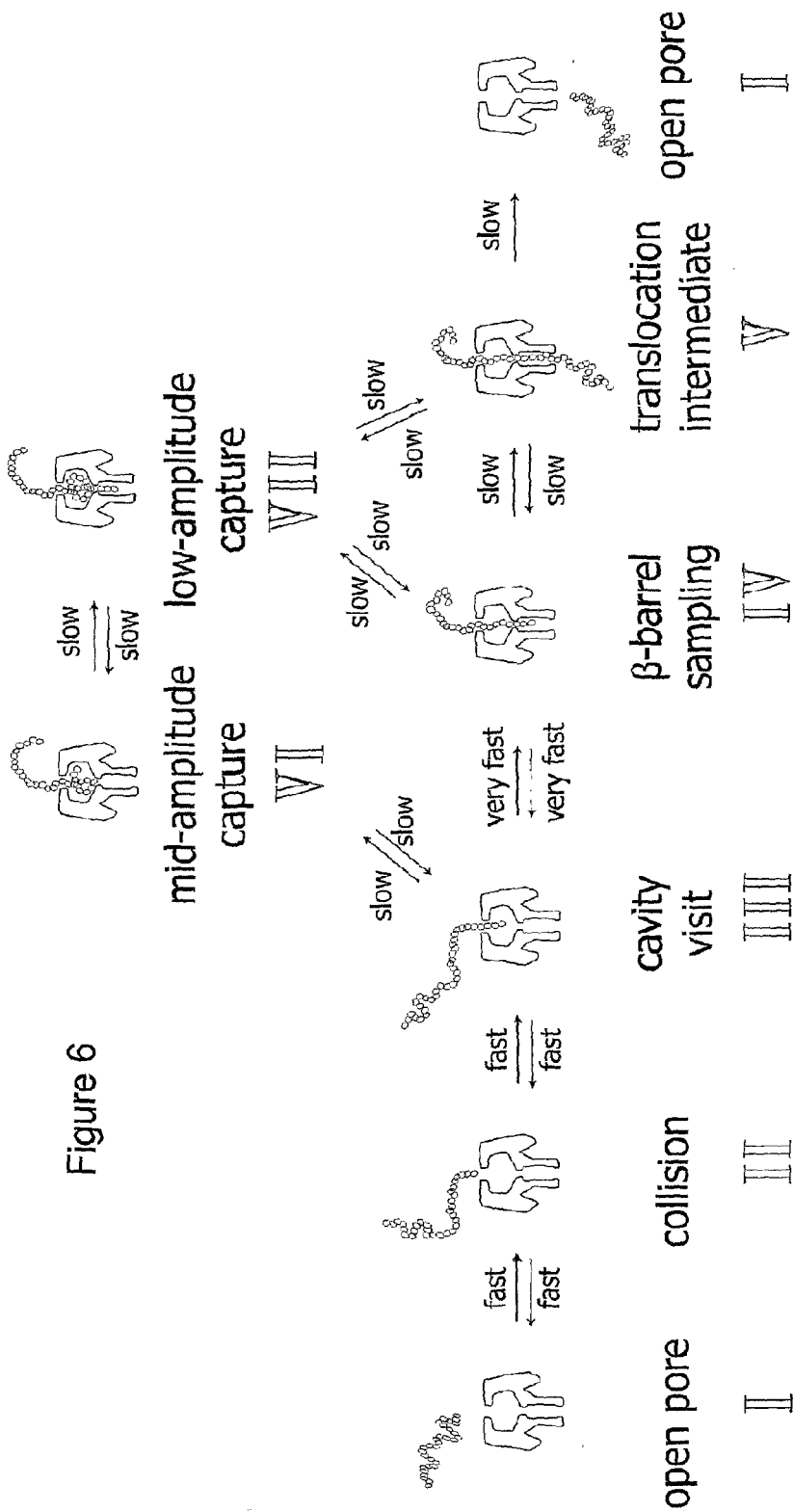
FIG. 6 shows the model for the translocation of DNA through the α-HL pore. To pass through the pore (V), DNA must first collide with the cis entrance of the pore (II), be transported through the vestibule (III) and enter the β barrel (IV). The DNA can prolong its visit within the vestibule and produce mid-amplitude and low-amplitude events corresponding to VI and VII. The processes that can be observed experimentally are labelled as events and are shown with slow interevent rates. All steps are reversible with exception of translocation. In type A events, DNA collides with the pore, enters the vestibule and then directly translocates through the β barrel to exit on the trans side of the pore. Sampling of the barrel (III↔IV) during this process is too fast to observe. In type B events, DNA enters the pore but instead of penetrating the β barrel it has a prolonged interaction with the vestibule to produce the mid-amplitude event (I→II→III→VI). In this case, DNA exits the pore from the same cis entrance from which it entered (VI→I-II→II→I). Like type B events, type C events first show a mid-amplitude current (I→II→III→VI), but then one end of the DNA enters the β barrel (VII) and a translocation event occurs (VII→V→I). In type D events, the DNA most likely enters the β barrel (I→II→III→IV) but then stops translocating (VII), retracts back into the vestibule (VI) and exits the pore from the cis side (VI→III→II→I). Finally, in type E events, the DNA begins to translocate through the β barrel as in type C events (I→II→III→VI→VII→V), but then retracts into the vestibule (V→VII→VI) and exits the pore from the cis side as in type D events (VI→III→II→I). Intermediates expected to give mid-amplitude events are numbered in yellow, although II and III would be too short for observation. Intermediates expected to give low-amplitude events are numbered in red, although IV would be too short for observation.

A scheme for DNA capture and translocation that incorporates reversible sampling of the lumen is depicted (FIG. 6). Prior to a typical translocation event (via intermediate V, FIG. 6), a DNA molecule first collides with the pore (II). Upon visiting the vestibule (III), the DNA is transported by electrophoresis into the narrow β barrel (IV). Because the pores used here are anion selective, electroosmotic solvent flow will occur in the same direction (cis to trans) and assist DNA transport. At this point, the effect of the applied field on the DNA molecule is strongest and the polymer is pulled through the pore into the trans compartment (V→I), the only irreversible step in our scheme. The translocation intermediate (V) was observed experimentally by the abrupt reduction of the current to 90% of the open pore value (during type A and C events), an assignment that is supported by several observations in the literature. For example, Kasianowicz and co-workers showed that the cis addition of ssDNA produces short-lived current blockades of 85-100% of the open pore current. PCR analysis of the trans chamber revealed that DNA had passed through the αHL pore (Kasianowicz, J. J., Brandin, E., Branton, D., & Deamer, D. W. (1996) Characterization of individual polynucleotide molecules using a membrane channel. *Proc. Natl. Acad. Sci. USA* 93, 13770-13773).

In the case of the WT-αHL pore, not all the current blockades were due to straightforward DNA translocation. In one-third of the events, a mid-amplitude event was observed (FIG. 2a). This current signature is interpreted to represent DNA molecules during a prolonged occupancy of the α-HL vestibule (intermediate VI, FIG. 6), as supported by the fact that occupancy of the vestibule is associated with a lower conductance, but not one reduced to the extent caused by occupancy of the barrel. For example, when DNA duplexes are tethered within the vestibule, a 38% reduction of the pore current is observed (Howorka, S. & Bayley, H. (2002) Probing distance and electrical potential within a protein pore with tethered DNA. *Biophys. J.* 83, 3202-3210). Capture within the vestibule is similar to the phenomenon of entropic trapping described by Han and Craighead (Han, J. & Craighead, H. G. (2002) Characterization and optimization of an entropic trap for DNA separation. *Anal Chem* 74, 394-401).

Figure 10:
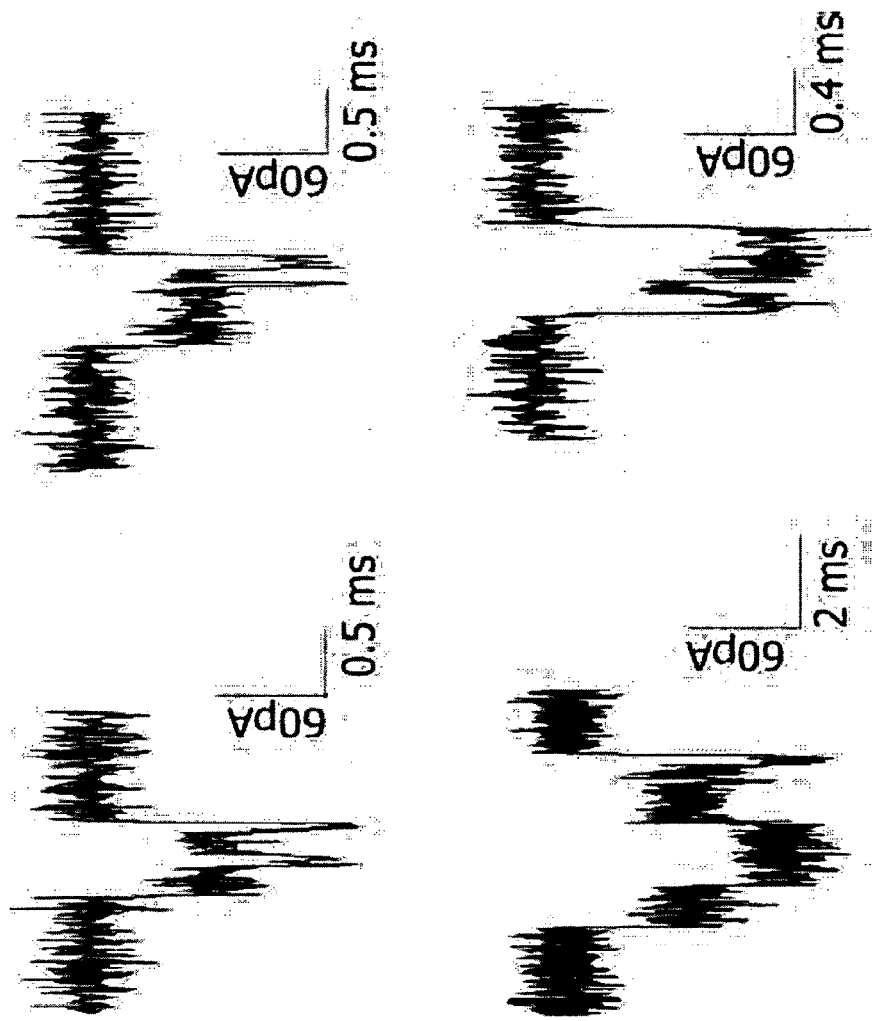
FIG. 10 shows rare (<1%) current blockade events for DNA translocation through WT-α-HL nanopores at +120 mV showing multiple transitions between the mid-amplitude and low-amplitude states. The conditions are described in the legend to FIG. 2.

DNA molecules captured in the mid-amplitude configuration (VI, FIG. 6) can either exit the pore from the cis compartment (type B event, FIG. 2a), or proceed into the β barrel producing a low-amplitude signal (intermediate VII). From this configuration, the DNA can either complete translocation through the pore and exit on the trans side of the bilayer (type C event, FIG. 2a, via intermediate V, FIG. 6) or retract back into the vestibule and exit on the cis side (type E event, FIG. 2a). Finally, DNA can visit the vestibule, move at once into the β barrel to produce a low-amplitude signal, but instead of proceeding through the pore (type A event) reverse into the vestibule to produce a mid-amplitude signal, before exiting on the cis side (type D, FIG. 2a). Butler and colleagues recently observed the same phenomena and came to similar conclusions (Butler T Z, Gundlach J H, Troll M A: Determination of RNA orientation during translocation through a biological nanopore. *Biophys J* 2006, 90:190-199). In further support of the scheme, we have observed a few events with multiple mid-to-low (VI↔VII) steps (FIG. 10). In addition, we have observed type A-E events with additional DNAs, both with and without weak secondary structure (D. Japrung, unpublished work). The 92-mer used in the present work is unlikely to possess stem-loop structures, but the existence of helical structure within single-stranded nucleic acids remains a contentious area (Seol, Y., Skinner, G. M., Visscher, K., Buhot, A., & Halperin, A. (2007) Stretching of homopolymeric RNA reveals single-stranded helices and base-stacking. *Phys Rev Lett* 98, 158103).

The Effects of Charge in the Lumen of the Pore

A ring of seven positive charges introduced by site-directed mutagenesis near the internal constriction increased the frequency of translocation of DNA molecules (FIG. 3), and reduced the fraction of events with mid-amplitude components (FIG. 2ab). However, according to our proposed scheme, the DNA is within a Debye length of the residues forming the constriction only as intermediate IV, V or VII (FIG. 6) and cannot sense these charged groups from bulk solution. Therefore, to explain the effect of charge at the constriction, we propose that a DNA molecule enters and quickly exits the top end of the β barrel (sampling, III→IV, FIG. 6) many times before either retracting back into the cis compartment or proceeding to intermediate V, VI or VII. An increase in positive charge at the constriction (Glu-111→Asn or Met-113→Arg) increases the affinity of DNA for the pore at this location. Therefore, in these mutants the number of molecules that return to the vestibule after sampling the β barrel is reduced and the rate of occurrence of direct DNA translocation events (type A) is increased. In addition, since the fraction of time spent as intermediate III is decreased, the probability of observing a mid-amplitude event (VI) is reduced and fewer type B to E events occur. The sampling of the β barrel by ssDNA was observed experimentally at +100 mV for short DNA overhangs protruding from a duplex DNA tethered near the cis entrance of the pore (Howorka S, Bayley H: Probing distance and electrical potential within a protein pore with tethered DNA. *Biophys. J.* 2002, 83:3202-3210). For untethered DNA molecules, we propose that the sampling of the barrel is much quicker and not observed because of bandwidth limitations.

The elimination of a charge at the cis entrance of the pore in the RL2 mutant (Lys-8 Ala) reduced the fraction of type B and C events (Table 2), and decreased the frequency of DNA translocation by an order of magnitude (FIG. 3). We attribute these effects to a reduced affinity of DNA for the pore. A weaker interaction with the pore during collisions with the entrance and visits to the vestibule (intermediates II and III) reduces the overall number of observable captures.

Importantly, we have observed an increased number of capture events with □HL pores with increased internal positive charge with several additional DNAs and RNAs, as described here for the 92-mer, Therefore, the phenomena we describe are not peculiar to a specific DNA sequence.

Role of the β barrel

The depth to which DNA samples the β barrel (step IV) was investigated by introducing a ring of arginines at various positions. When DNA was added from the cis side, we found that the DNA translocation frequency decreased roughly exponentially as the ring was moved from the constriction (M113R-RL2) towards the trans entrance (N123R-RL2) of the pore (FIG. 4), suggesting that DNA molecules can sample the β barrel deeply. When presented from the cis side, the DNA must occasionally come close to residue 119, which is 2.3 nm away from the constriction. Accordingly, when the DNA was added on the trans side of the pore, more translocation events were observed (at −120 mV) when the ring of arginines was closer to the trans entrance (FIG. 9). As the ring of charges is moved towards the trans entrance, the unitary conductance of the pore is decreased by about twofold (Table 4), but this is unlikely to be fully related to the dramatic change in DNA translocation frequency of more than ten-fold. Further, in other cases, the trend is not seen. For example, RL2 has a similar conductance to the WT pore, but a far lower translocation frequency.

Electroosmotic Effect

In the preceding discussion, we have ignored the differences in electroosmotic solvent flow through the various α-HL pores. For example, the WT α-HL pore is slightly anion selective ($P_+/P_-=0.78$, in 1 M NaCl cis and 0.2 M NaCl trans) and, therefore, there will be a net flow of water from cis to trans under a positive potential (Gu L-Q, Cheley S, Bayley H: Electroosmotic enhancement of the binding of a neutral molecule to a transmembrane pore. *Proc. Natl. Acad. Sci. USA* 2003, 100:15498-15503). The M113R-WT pore is more anion selective than the WT pore ($P_+/P_-=0.38$, in 1 M NaCl cis and 0.2 M NaCl trans) and the increased frequency of DNA translocation with this mutant could be due, at least in part, to enhanced electroosmotic flow. A simple calculation, based on equation 2 in Gu, L.-Q., Cheley, S., & Bayley, H. (2003) Electroosmotic enhancement of the binding of a neutral molecule to a transmembrane pore. *Proc. Natl. Acad. Sci. USA* 100, 15498-15503, assuming that five molecules of water are carried per ion, suggests that with a weakly anion selective pore ($P_+/P_-=0.9$) only two additional molecules are transported to the mouth of the pore per second in a 1 μM DNA solution. With a moderately selective pore ($P_+/P_-=0.5$), 23 additional molecules arrive per second and with a more strongly selective pore ($P_+/P_-= 0.1$) an additional 53. These numbers are of a similar order of magnitude to the effects seen here.

However, several lines of evidence suggest that electroosmosis does not have a dominant effect on the frequency of DNA translocation through the α-HL pore at +120 mV. For example, E111N-WT shows a higher DNA translocation frequency than M113R-WT, but it is much less anion selective ($P_+/P_-=0.71$, in 1 M NaCl cis and 0.2 M NaCl trans) (Gu L-Q, Cheley S, Bayley H: Electroosmotic enhancement of the binding of a neutral molecule to a transmembrane pore. *Proc. Natl. Acad. Sci. USA* 2003, 100:15498-15503). The mutant RL2 has a similar ion selectivity to WT α-HL ($P_+/P_-=0.68$, in 0.9 M KCl cis and 0.3 M KCl, trans R. Madathil, unpublished), but the DNA translocation frequency with RL2 is ten-fold lower (Table 4). RL2 also shows the same DNA translocation frequency as N123R-RL2 (FIG. 5), which has a higher anion selectivity ($P_+/P_-=0.24$, in 0.3 M NaCl cis and 1.0 M NaCl trans, R. Madathil, unpublished). Finally, if the trend in DNA translocation frequencies observed when a ring of arginines is placed at different positions within the β barrel were due to electroosmosis, we would not expect the trend to reverse when DNA is threaded from the trans rather than the cis side. Previous workers have recognized the possibilty that electroosmosis might affect the rate of DNA translocation through nanopores (Chen P, Mitsui T, Farmer D B, Golovchenko J A, Gordon R G, Branton D: Atomic layer deposition to fine-tune the surface properties and diameters of fabricated nanopores. *Nano Letters* 2004, 4:1333-1337) while others have ignored the effect (Meller A: Dynamics of polynucleotide transport through nanometer-scale pores. *J. Phys.: Condens. Matter* 2003, 15:R581-R607) or considered it an unlikely contributor under prevailing conditions (Gershow M, Golovchenko J A: Recapturing and trapping single molecules with a solid-state nanopore. *Nat Nanotechnol* 2007, 2:775-779). It is also possible that electroosmosis has a role in decreasing the type B to E events by promoting laminar flow through the vestibule.

Movileanu and colleagues have explored the passage of positively charged peptides through α-HL pores with additional negative charge in the lumen (Wolfe, A. J., Mohammad, M. M., Cheley, S., Bayley, H., & Movileanu, L. (2007) Catalyzing the translocation of polypeptides through attractive interactions. *J Am Chem Soc* 129, 14034-14041; Mohammad, M. M., Prakash, S., Matouschek, A., & Movileanu, L. (2008) Controlling a single protein in a nanopore through electrostatic traps. *J Am Chem Soc* 130, 4081-4088). Both the rate of capture and the translocation time were increased, which they explained in terms of reduced barriers to transit. The differences between nucleic acids, for which the translocation time is not greatly altered (τ, Table 4), and peptides will require further experimentation to resolve, but one obvious distinction is the higher charge density on nucleic acids.

Voltage Dependence of DNA Translocation.

The frequency of DNA translocation events through α-HL pores depends strongly on the applied potential in a non-linear fashion (FIG. 5a). At the low applied potentials of our experiments, the oligonucleotides that visit the vestibule (intermediate III, FIG. 6) do not sense a strong potential drop (<10 mV at an applied potential of +100 mV; Howorka S, Bayley H: Probing distance and electrical potential within a protein pore with tethered DNA. *Biophys. J.* 2002, 83:3202-3210). Further, the contributions of local potentials from fixed charges in the protein are expected to be small, given the high ionic strength. Therefore, only intermediates IV and V (FIG. 6) in which the DNA is inside the β barrel and subjected to a strong electric field are expected to be significantly influenced by the applied potential. The existence of a voltage threshold for DNA translocation and the steep dependence of the frequency of translocation on potential at <150 mV (FIG. 5) suggests that the energy barrier for DNA translocation is large and only a fraction of the DNA molecules that reach the β barrel (intermediate IV) pass through the entire pore. Increasing the charge near the constriction lowers the energy barrier and more DNA molecules can pass through the β barrel (see above). The lower energy barrier is also associated with a lower threshold for DNA translocation (Table 3). Other groups have observed the threshold and the steep voltage dependence with WT α-HL pores and fitted their observations to exponential functions (Henrickson S E, Misakian M, Robertson B, Kasianowicz J J: Driven DNA transport into an asymmetric nanometer-scale pore. *Phys. Rev. Lett.* 2000, 85:3057-3060).

At higher potentials (V>150 mV), the voltage dependence of DNA translocation is less steep (FIG. 5). Other groups, working with the WT α-HL pore, have described a linear dependence on voltage at high potentials (Meller A: Dynamics of polynucleotide transport through nanometer-scale pores. *J. Phys.: Condens. Matter* 2003, 15:R581-R607), but in our case the dependence is stronger. Interestingly, the maximum frequency of DNA translocation ($f_{max}$) for α-HL WT and the mutant pores varies considerably (FIG. 5), the hallmark of electroosmosis (Wong C T, Muthukumar M: Polymer capture by electro-osmotic flow of oppositely charged nanopores. *J Chem Phys* 2007, 126:164903), which may play a greater role under these conditions.

3. Conclusion

We have used site-directed mutagenesis to increase the frequency of ssDNA translocation through α-HL pores, and at the same time the threshold for DNA translocation has been lowered. The most likely mechanisms for the increased rate of translocation are rapid sampling of the interior of the pore by the DNA (FIG. 6), increased electroosmotic flow (Chen P, Mitsui T, Farmer D B, Golovchenko J A, Gordon R G, Branton D: Atomic layer deposition to fine-tune the surface properties and diameters of fabricated nanopores. *Nano Letters* 2004, 4:1333-1337) or a combination of the two that depends on the applied potential. The new engineered pores or derivatives of them will be useful for enhancing the sensitivity of α-HL as a biosensor of nucleic acids. An additional potential application is in nanopore sequencing, where the in a single DNA strand are read off one by one during translocation. An increase in the frequency of ssDNA translocation through α-HL pores, as demonstrated here, might, for example, be used to reduce the deadtime between reads. By analogy, engineered pores might also be used to increase the capture efficiency of individual bases during exonuclease sequencing, which will be vital for accurate reads.

Example 2

Here, we show that the translocation of DNA molecules through the α-HL biological nanopore can be reduced by more than two orders of magnitude by introducing positive charges in the lumen of the pore. Although the ionic current during DNA translocation was almost completely suppressed, we suggest that these nanopores can be used to control the speed of DNA translocation, which, in combination with emerging technologies for DNA analysis, could lead to the development of a robust platform for the sequencing of nucleic acids.

1. Materials and Methods

The same Materials and Methods used in Example 1 were also used in this Example.

2. Results and Discussion 2.1. Ionic Current Through α-HL Nanopores

Individual channels were examined by single-channel current recordings in planar lipid bilayers in 1M KCl, 25 mM Tris.HCl containing 100 µM EDTA at pH 8.0. At +120 mV, all channels displayed stable open pore currents (+120 mV), however, some of the pores showed isolated, short-lived current blockade events, attributed to opening and closing of the pore (Kasianowickz et al., *Proc. Natl. Acad. Sci. USA* 1996, supra). The unitary conductance values (g) varied greatly among nanopores (Table 5).

TABLE 5

DNA translocation through the α-HL nanopores at +120 mV. All experiment were carried out in 1M KCL, 25 mM Tris.HCl containing 100 µM of EDTA. $\tau_G$ is the most likely DNA translocation speed, g is the unitary conductance of the nanopores and $I_{RES}$ is the residual current percent during DNA translocation. All mutants, except for WT and 2N, are in RL2 background (SEQ ID NOs: 3 and 4). Errors are shown in standard deviation.

| Pore | $\tau_G$ (µs/base) | $I_{RES}$ | g, nS (+120 mV) |
|---|---|---|---|
| WT* | 1.52 ± 0.00 | 9.5 | 1.04 ± 0.01 |
|  | (n = 6) | (n = 5) | (n = 23) |
| RL2* | 1.63 ± 0.00 | 10.5 | 1.03 ± 0.02 |
|  | (n = 4) | (n = 4) | (n = 16) |
| 2N | 2.01 ± 0.07 | 26.5 | 1.07 ± 0.05 |
| (E111N-K147N) | (n = 4) | (n = 4) | (n = 4) |
| M113R-RL2* | 1.53 ± 0.10 | 3.0 | 1.19 ± 0.06 |
|  | (n = 4) | (n = 5) | (n = 8) |
| N123R-RL2* | 2.39 ± 0.22 | 3.0 | 0.64 ± 0.02 |
|  | (n = 5) | (n = 4) | (n = 10) |
| 2R◇ | 2.99 ± 0.15 | 2.0 | 0.98 ± 0.05 |
| (M113R-N123R) | (n = 5) | (n = 4) | (n = 6) |
| 2R● | 4.43 ± 0.23 | 2.5 | 0.57 ± 0.03 |
| (N123R-D127R) | (n = 5) | (n = 4) | (n = 5) |
| 2R† | 4.49 ± 0.69 | 2.0 | 1.06 ± 0.06 |
| (M113R-T145R) | (n = 5) | (n = 5) | (n = 5) |
| 3R | 16.0 ± 4.0 | 0.5 | 0.87 ± 0.06 |
| (T115R-G119R-123R) | (n = 7) | (n = 6) | (n = 7) |
| 4R | 29.0 ± 5.5 | 0.5 | 0.70 ± 0.09 |
| (T115R-G119R-N123R-D127R) | (n = 4) | (n = 4) | (n = 6) |
| 7R | 269 ± 14 | 0.5 | 0.87 ± 0.02 |
| (M113R-T115R-T117R-G119R-N121R-N123R-T125R) | (n = 6) | (n = 6) | (n = 6) |
| $7R_6 RL2_1$ | 100 ± 35 | 0.5 | 0.91 ± 0.02 |
|  | (n = 7) | (n = 5) | (n = 7) |
| $7R_5 RL2_2$ | 66.6 ± 10.1 | 0.5 | 0.88 ± 0.09 |
|  | (n = 5) | (n = 5) | (n = 5) |
| $7R_4 RL2_3$ | 51.2 ± 6.1 | 0.5 | 0.86 ± 0.05 |
|  | (n = 5) | (n = 5) | (n = 5) |
| $7R_3 RL2_4$ | 21.4 ± 8.8 | 1.0 | 0.94 ± 0.05 |
|  | (n = 7) | (n = 5) | (n = 7) |
| $7R_2 RL2_5$ | 9.89 ± 2.15 | 1.5 | 0.93 ± 0.07 |
|  | (n = 5) | (n = 5) | (n = 5) |
| $7R_1 RL2_6$ | 5.95 ± 1.10 | 4.0 | 0.99 ± 0.05 |
|  | (n = 5) | (n = 4) | (n = 5) |

*data from Example 1 and Maglia, *Proc. Natl. Acad. Sci. USA*, 2008, supra

All nanopores in this study, with exception of WT and 2N (E111N-K147N), were made by using the RL2 gene (SEQ ID NO: 3) as template, which encodes four amino acid mutations in the β-barrel domain (Val-124→Leu, Gly-130→Ser, Asn-139→Gln, Ile-142→Leu) and one in the cis entrance of the pore (Lys-8→Ala) (SEQ ID NO: 4; Cheley, *Protein Sci.,* 1999, supra). The introduction of positive charges close to the constriction site increased the ionic current of the nanopores with respect to the WT pore, as observed in the homoheptamers formed by M113R and M113R-T145R. By contrast, ionic currents were reduced significantly when positive charges were introduced close to the trans exit of the α-HL pore (Maglia et al., (2008) *Proc. Natl. Acad. Sci. USA*, 105(50): 19720-19725). N123R and N123R-D127R pores displayed the highest decrease in ionic current, with unitary conductance values of 0.64±0.02 nS (n=10, +120 mV) and 0.57±0.03 (n=5, +120 mV), respectively (Table 5). The current rectification ratios, calculated as the value of ionic current at +50 divided by the current at −50, also varied depending on the position of the charges. Nanopores with additional positive charges introduced near the trans exit (after position 121) showed current rectification lower than 1 (e.g. they show higher current at negative applied potentials than at positive applied potentials), while mutants with positive charges introduced close to the cis side displayed similar rectifying behaviour to WT-α-HL (higher than 1). On the other hand, nanopores with no charges at the central constriction displayed almost non-rectifying behaviour (R~1 in 2N)). These results suggest, in agreement with previous results (Wolfe, *J Am Chem Soc*, 2007, supra; Maglia et al., *Proc. Natl. Acad. Sci. USA*, 2008, supra), that the transport of molecules (e.g. ions) through the relatively small dimensions of the α-HL nanopore can be strongly altered by the introduction of charged residues in the β-barrel region of the pore.

2.2 DNA Translocation Through α-HL Nanopores

Figure 11:
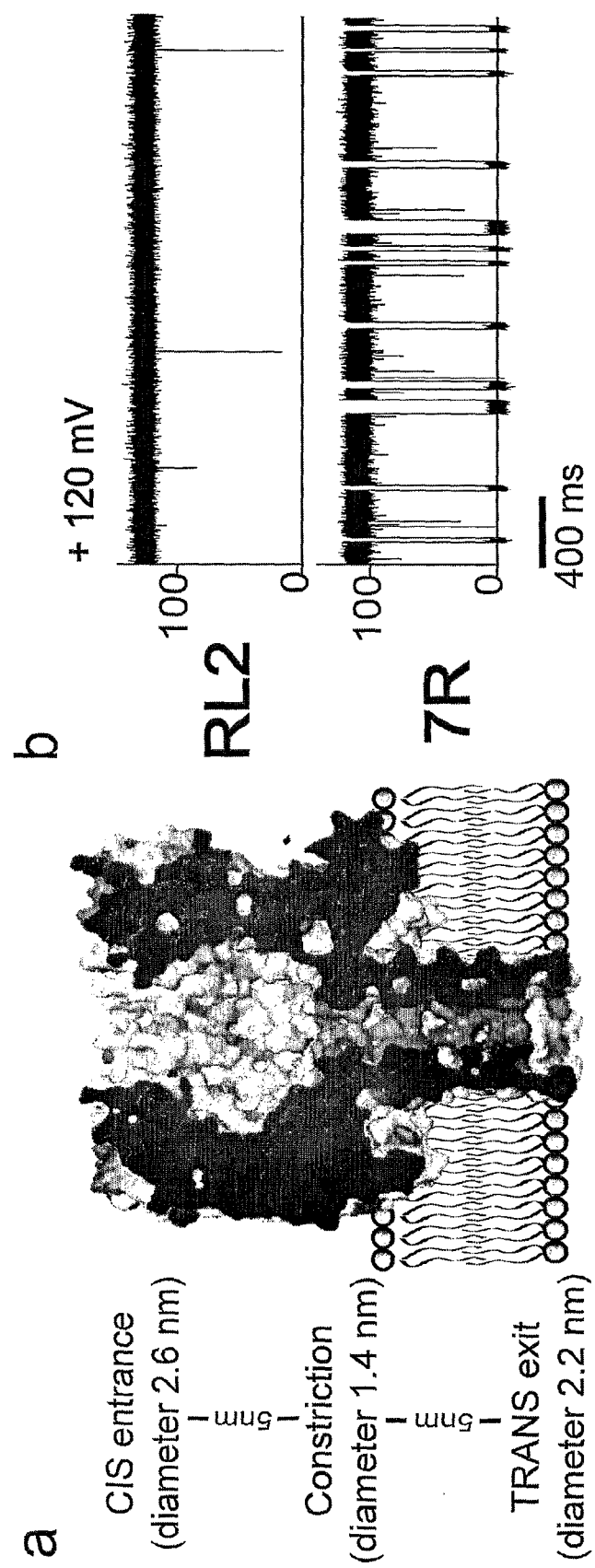
FIG. 11 shows: a) Section through a 7R nanopore. The amino acids at position 113, 115, 117, 119, 121, 123 and 125 were replaced by arginine using PyMOL (DeLano Scientific LLC, v 1.0) software from the WT nanopore (PDB:7AHL). Negative charged residues are coloured in red and positively charged residues in blue. b) Single channel recordings of 7R (top) and RL2-α-HL nanopores (bottom) at +120 mV after addition of 1 μM of ssDNA in the CIS side of the chamber. Experiments were performed at 1M KCl 25 mM Tris.HCl containing 100 uM EDTA at pH 8.
Figure 12:
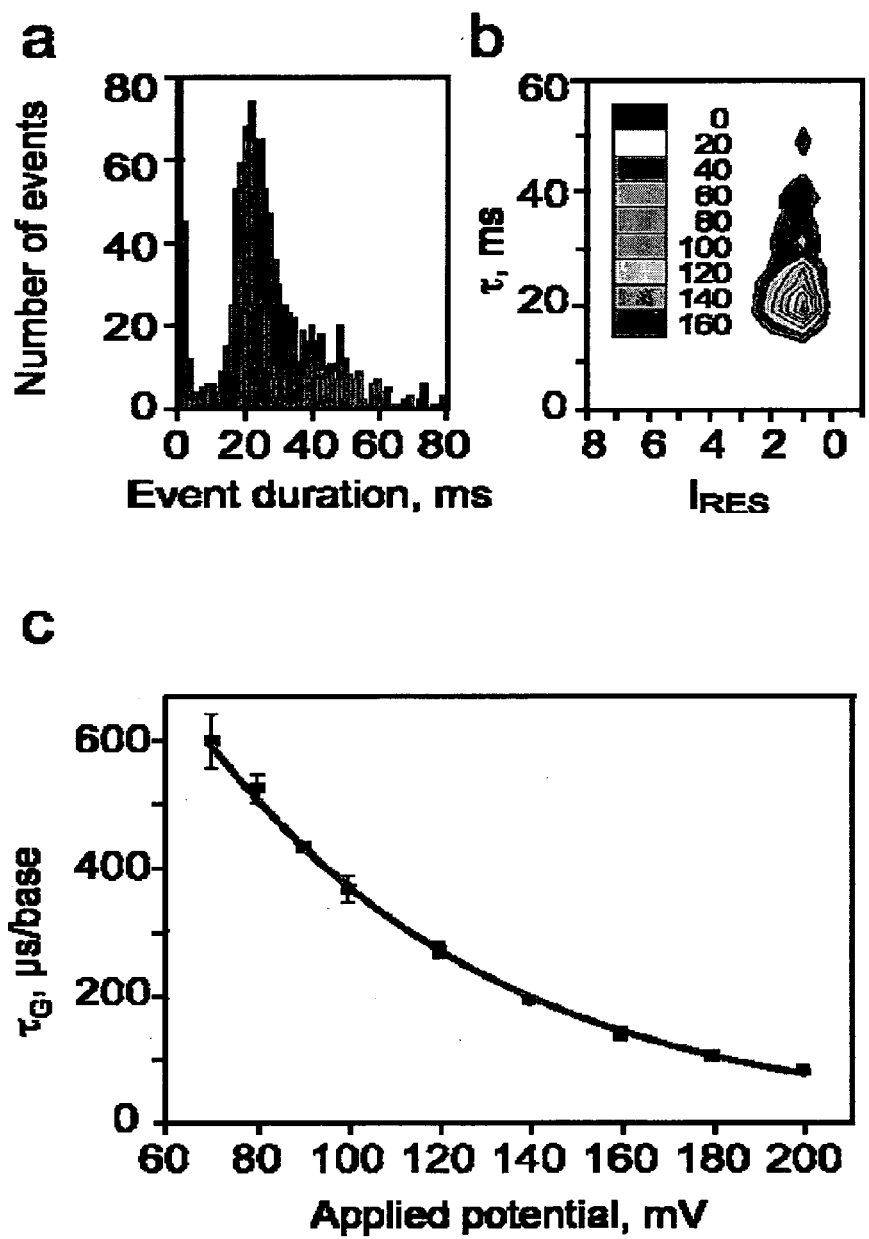
FIG. 12 shows DNA translocation through 7R nanopores. a) Event histogram showing the translocation time distribution through a 7R pore upon addition of 0.7 μM of ssDNA (92mer) to the CIS side of the chamber. Events <5 ms are attributed to the transient gating of 7R nanopore (see SI). b) 2-D distribution plot of DNA translocation events (τ>5 ms) versus the residual current during DNA translocation. The colour represents the density of the events as indicated in the inset. c) Dependence of the most likely DNA translocation speed of DNA through 7R nanopores on the applied voltage. The red line shows a single exponential fit.
Figure 13:
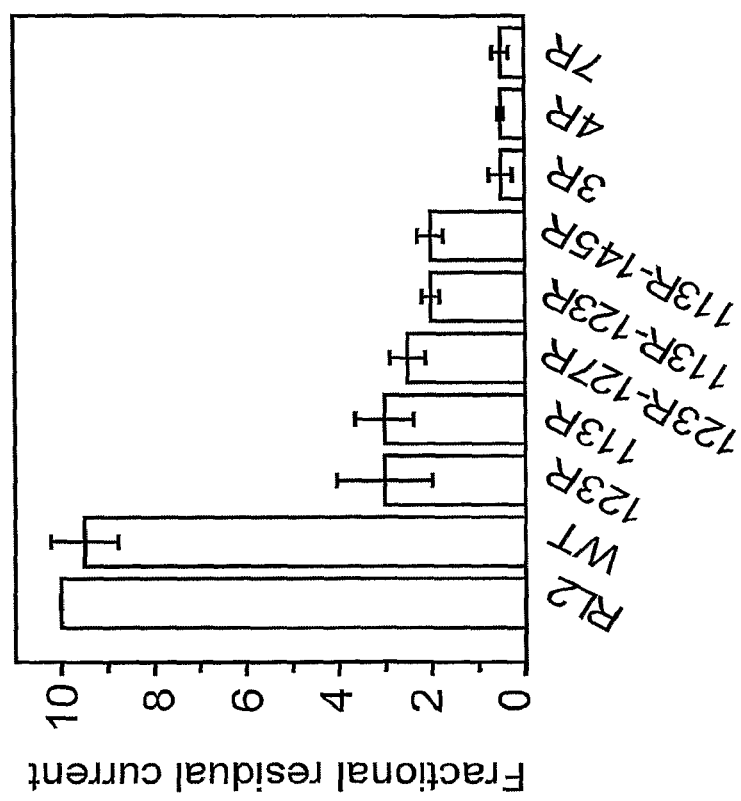
FIG. 13 shows residual current through WT and modified α-HL nanopores during ssDNA translocation at +120 mV. Errors express the standard deviation. All nanopores, except from WT, and 2N are in RL2 background. The fourth to last columns from the left concern the nanopores with additional positive charges.

The addition short ssDNA (92 bases nucleotide in this work) to the CIS side of the chamber under positive applied potential provokes current blockade, which are due to the translocation of single DNA molecules (Kasianowicz, *Proc. Natl. Acad. Sci. USA*, 1996, supra). The most likely translocation time, $\tau_G$, is defined as the peak of the Gaussian fit the histogram of events duration (FIG. 11a). For the WT nanopore, at +120 mV of DNA through the pore $\tau_G$ is of 0.141±0.004 ms, which corresponds to a translocation spped of 1.53±0.00 µs/nt, (n=6). Manipulation of charges in the barrel of the pore altered the interaction between DNA and the pore. The exponential decrease of the dwell time of the current blockades induced by DNA, as shown for example for 7R nanopores (FIG. 12b) indicates, however, that DNA also translocate through the altered nanopores.

The removal of the charges at the central constriction (E111N/147N) or the introduction of single (1R) and double (2R) arginine rings in the pore lumen had a negligible effect on the translocation speeds of DNA through the pore (the most likely translocation speeds in the 2R-α-HL mutants were just 2-3 fold lower relatively to WT-α-HL). The introduction of three (3R-α-HL) and four (4R) rings of arginines in the barrel of the nanopore reduced the most likely translocation speed ~10 and ~20 folds, respectively. The strongest effect was observed upon addition of seven rings of arginines residues in the lumen of the pore (7R), which decreased the translocation speeds of DNA through the pore by more than two orders of magnitude relative to the WT and RL2 α-HL pores (269±14 µs/nt Table 5).

2.3 Residual Current Through α-HL Nanopores

The residual current during the translocation of DNA molecules through α-HL nanopores ($I_{RES}$) is defined as the blocked pore current ($I_B$) divided by the open pore current ($I_O$) expressed in percent. WT nanopores showed a fractional residual current of 11%. In DNA nanopore sequencing, $I_{RES}$ is important because it is the most likely mean to which single bases will be discriminated as they are translocated through the pore. Unfortunately, while introductions of arginine residues allow the control of DNA translocation through α-HL nanopores, the residual current while DNA is translocating is greatly reduced (Table 5). Single and double arginines substitutions in the lumen of the pore reduced the residual current to 4% and 2%, respectively (Maglia, *Proc. Natl. Acad. Sci. USA*, 2008, supra and Table 5), while three or more arginine rings in the barrel reduced $I_{RES}$ to 0.5% (Table 5). By contrast, the replacement of the charged residues at the constriction site with smaller non-charged asparigine residues (E111N-K147N), increased the fractional residual current to 26%.

The effect of amino acids modification in the barrel of the pore on the residual current through the α-HL pore while DNA is in the pore is most likely due to a combination of steric and electrostatic effect. Arginine has a relatively large volume (173.4 Å$^3$) and when replace threonine (116.1 Å$^3$) or glycine (60.1 Å$^3$) residues will reduce the diameter of the pore and thus $I_{RES}$. Similarly, substitution of glutamate (138.4 Å$^3$) and lysine (166.7 Å$^3$) residues at the constriction with asparagine (117.4 Å$^3$) will slightly increase the diameter of the constriction and thus $I_{RES}$. However, electrostatic interactions are likely to play a large role. In the WT and mutants, a reduction of the volume alone can not account for the that positive charges in the barrel of the pore will also provide an additional energy barrier for the passage of positive ion, which provide most of the ionic current during DNA translocation.

2.4 DNA Translocation Through α-HL Hetero-Heptamers

Figure 14:
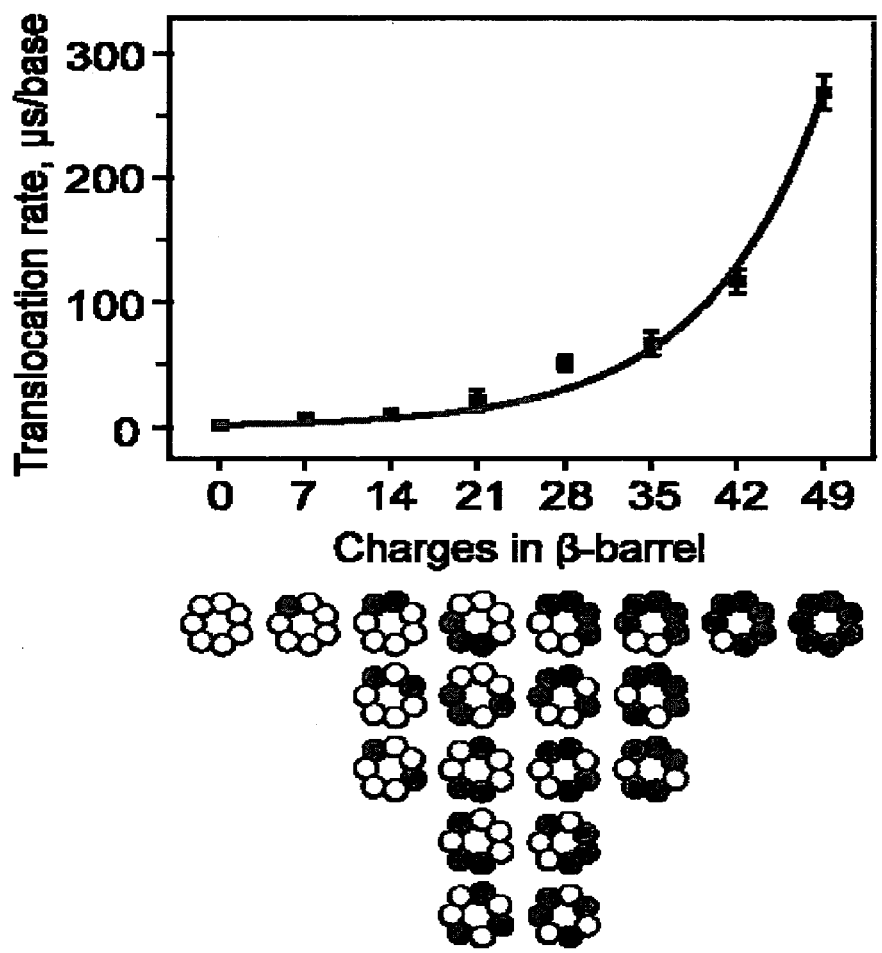
FIG. 14 shows the dependence of the DNA translocation speed on the internal charge of 7R heteromers. The data are fitted to a single-exponential curve (upper panel). Heteromers nanopores were obtained by mixing monomers of RL2 (open circles) with monomer of 7R (purple circles). In this way, eight different classes of heptamers (7RmRL2n-m; n=7, total number of subunits, m=0 . . . 7) containing from 7 to 49 extra positive charges can be created (lower panel).
Figure 15:
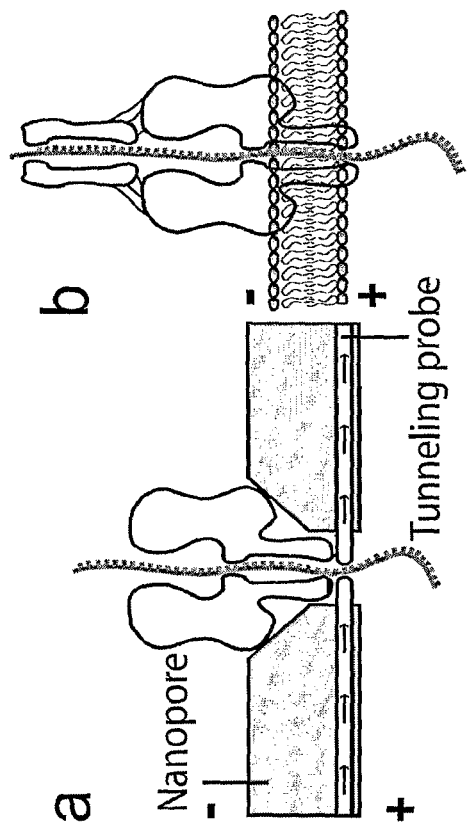
FIG. 15 shows the potential uses of 7R nanopores. a) Single strands are sequenced by reading the tunneling current. The 7R channel is incorporated into solid state nanopore functionalized with tunneling probes. Transverse tunneling currents through a ssDNA that is translocation through the pore are measured for recognition of single bases. 7R will control the time that each nucleotide remains between the tunneling probes. b) Strand sequencing using electrophysiological techniques. A β-barrel containing intrapositive charges is attached to the CIS entrance of the α-HL nanopore for controlling the speed of ssDNA. Differences between single nucleotides are measured by changes in conductance of the nanopore generated by the translocation of DNA.

Hetero-heptamers α-HL pores were prepared by mixing 7R monomers containing a D8 tail at the C termini with RL2 monomers on rabbit red blood cells, and mono-derivatized heptamers were separated by SDS-PAGE (SI). The modified pores contained, therefore, lines of single arginine residues along the barrel of the pore stretching from the constriction to the trans exit of the pore, forming a slide to guide DNA translocation through the α-HL pore. It was hoped that the arginine residues would reduce DNA translocation by interacting strongly with the phosphate groups of DNA, while allowing K+ ions still to pass through the pore, thus allowing base recognition. Derivatized heptamers, however, showed very similar residual current and DNA translocation speeds as homo-heptamers with comparable positive charges in the barrel (Table 5). Interestingly, the translocation speed of DNA through the pore depended exponentially on the internal charge of the barrel (FIG. 14), suggesting a strong polymer-pore interactions (Wanunu, M. Sutin, J. McNally, B. Chow, A. and A. Meller (2008), *Biophys. J.*, 95, 4716-25; Luo et al., (2007), *Phys. Rev. Lett*, 99(14): 148102).

Tables 6 to 13 below set out the sequence information.

TABLE 6

SEQ ID NOs: 1 and 2-Wild-type α-hemolysin from *Staphylococcus aureus*

```
ATGGCAGATTCTGATATTAATATTAAAACCGGTACTACAGATATTGGAAGCAATACTACAGTAA
AAACAGGTGATTTAGTCACTTATGATAAAGAAAATGGCATGCACAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCAAGAAATTC
GATTGATACAAAAGAGTATATGAGTACTTTAACTTATGGATTCAACGGTAATGTTACTGGTGAT
GATACAGGAAAAATTGGCGGCCTTATTGGTGCAAATGTTTCGATTGGTCATACACTGAAATATG
TTCAACCTGATTTCAAAACAATTTTAGAGAGCCCAACTGATAAAAAAGTAGGCTGGAAAGTGAT
```

TABLE 6 -continued

SEQ ID NOs: 1 and 2-Wild-type α-hemolysin from *Staphylococcus aureus*

ATTTAACAATATGGTGAATCAAAATTGGGGACCATACGATCGAGATTCTTGGAACCCGGTATAT
GGCAATCAACTTTTCATGAAAACTAGAAATGGTTCTATGAAAGCAGCAGATAACTTCCTTGATC
CTAACAAAGCAAGTTCTCTATTATCTTCAGGGTTTTCACCAGACTTCGCTACAGTTATTACTAT
GGATAGAAAAGCATCCAAACAACAAACAAAATAGATGTAATATACGAACGAGTTCGTGATGAT
TACCAATTGCATTGGACTTCAACAAATTGGAAAGGTACCAATACTAAAGATAAATGGACAGATC
GTTCTTCAGAAAGATATAAAATCGATTGGGAAAAAGAAGAAATGACAAAT

ADSDINIKTGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTKEYMSTLTYGFNGNVTGDD
TGKIGGLIGANVSIGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 7

SEQ ID NOs: 3 and 4-α-hemolysin RL2

ATGGCAGATTCTGATATTAATATTGCAACCGGTACTACAGATATTGGAAGCAATACTACAGTAA
AAACAGGTGATTTAGTCACTTATGATAAAGAAATGGCATGCACAAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCGCGGAATTC
GATTGATACAAAAGAGTATATGAGT

ACGTTAACGTACGGATTCAACGGTAACCTTACTGGTGATGATACTAGTAAAATTGGAGGCCTTA
TTGGGGGCCCAGGTTTCCCTAGGTCATACACTTAAGTATGTTCAACCTGATTTCAAACAATTCT
CGAGAGCCCAACTGATAAAAAGTAGGCTGGAAAGTGATATTTAACAATATGGTGAATCAAAAT
TGGGGACCATACGATCGAGATTCTTGGAACCCGGTATATGGCAATCAACTTTTCATGAAAACTA
GAAATGGTTCTATGAAAGCAGCAGATAACTTCCTTGATCCTAACAAAGCAAGTTCTCTATTATC
TTCAGGGTTTTCACCAGACTTCGCTACAGTTATTACTATGGATAGAAAAGCATCCAAACAACAA
ACAAATATAGATGTAATATACGAACGAGTTCGTGATGATTACCAATTGCATTGGACTTCAACAA
ATTGGAAAGGTACCAATACTAAAGATAAATGGACAGATCGTTCTTCAGAAAGATATAAAATCGA
TTGGGAAAAAGAAGAAATGACAAATTAA

ADSDINIATGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTKEYMSTLTYGFNGNLTGDD
TSKIGGLIGAQVSLGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 8

SEQ ID NOs: 5 and 6-α-hemolysin M113R-WT

ATGGCAGATTCTGATATTAATATTAAAACCGGTACTACAGATATTGGAAGCAATACTACAGTAA
AAACAGGTGATTTAGTCACTTATGATAAAGAAATGGCATGCACAAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCAAGAAATTC
GATTGATACAAAAGAGTATAGGAGTACTTAACTTATGGATTCAACGGTAATGTTACTGGTGAT
GATACAGGAAAAATTGGCGGCCTTATTGGTGCAAATGTTTCGATTGGTCATACACTGAAATATG
TTCAACCTGATTTCAAAACAATTTTAGAGAGCCCAACTGATAAAAAGTAGGCTGGAAAGTGAT
ATTTAACAATATGGTGAATCAAAATTGGGGACCATACGATCGAGATTCTTGGAACCCGGTATAT
GGCAATCAACTTTTCATGAAAACTAGAAATGGTTCTATGAAAGCAGCAGATAACTTCCTTGATC
CTAACAAAGCAAGTTCTCTATTATCTTCAGGGTTTTCACCAGACTTCGCTACAGTTATTACTAT
GGATAGAAAAGCATCCAAACAACAAACAAATATAGATGTAATATACGAACGAGTTCGTGATGAT
TACCAATTGCATTGGACTTCAACAAATTGGAAAGGTACCAATACTAAAGATAAATGGACAGATC
GTTCTTCAGAAAGATATAAAATCGATTGGGAAAAAGAAGAAATGACAAATTAA

ADSDINIKTGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTKEYRSTLTYGFNGNVTGDD
TGKIGGLIGANVSIGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 9

SEQ ID NOs: 7 and 8-α-hemolysin E111N-WT

ATGGCAGATTCTGATATTAATATTAAAACCGGTACTACAGATATTGGAAGCAATACTACAGTAA
AAACAGGTGATTTAGTCACTTATGATAAAGAAAATGGCATGCACAAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCAAGAAATTC
GATTGATACAAAAAACTATATGAGTACTTTAACTTATGGTTTCAACGGTAATGTTACTGGTGAT
GATACAGGAAAAATTGGCGGCCTTATTGGTGCAAATGTTTCGATTGGTCATACACTGAAATATG
TTCAACCTGATTTCAAAACAATTTTAGAGAGCCCAACTGATAAAAAAGTAGGCTGGAAAGTGAT
ATTTAACAATATGGTGAATCAAATTGGGGACCATACGATCGAGATTCTTGGAACCCGGTATAT
GGCAATCAACTTTTCATGAAAACTAGAAATGGTTCTATGAAAGCAGCAGATAACTTCCTTGATC
CTAACAAAGCAAGTTCTCTATTATCTTCAGGGTTTTCACCAGACTTCGCTACAGTTATTACTAT
GGATAGAAAAGCATCCAAACAACAAACAAATATAGATGTAATATACGAACGAGTTCGTGATGAT
TACCAATTGCATTGGACTTCAACAAATTGGAAAGGTACCAATACTAAAGATAAATGGACAGATC
GTTCTTCAGAAAGATATAAAATCGATTGGGAAAAAGAAGAAATGACAAATTAA

ADSDINIKTGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTK■YMSTLTYGFNGNVTGDD
TGKIGGLIGANVSIGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 10

SEQ ID NOs: 9 and 10-α-hemolysin A8R-RL2

ATGGCAGATTCTGATATTAATATTAAAACCGGTACTACAGATATTGGAAGCAATACTACAGTAA
AAACAGGTGATTTAGTCACTTATGATAAAGAAAATGGCATGCACAAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCGCGGAATTC
GATTGATACAAAAGAGTATATGAGTACGTTAACGTACGGATTCAACGGTAACCTTACTGGTGAT
GATACTAGTAAAATTGGAGGCCTTATTGGGGCCCAGGTTTCCCTAGGTCATACACTTAAGTATG
TTCAACCTGATTTCAAAACAATTCTCGAGAGCCCAACTGATAAAAAAGTAGGCTGGAAAGTGAT
ATTTAACAATATGGTGAATCAAATTGGGGACCATACGATCGAGATTCTTGGAACCCGGTATAT
GGCAATCAACTTTTCATGAAAACTAGAAATGGTTCTATGAAAGCAGCAGATAACTTCCTTGATC
CTAACAAAGCAAGTTCTCTATTATCTTCAGGGTTTTCACCAGACTTCGCTACAGTTATTACTAT
GGATAGAAAAGCATCCAAACAACAAACAAATATAGATGTAATATACGAACGAGTTCGTGATGAT
TACCAATTGCATTGGACTTCAACAAATTGCAAAGGTACCAATACTAAAGATAAATGGACAGATC
GTTCTTCAGAAAGATATAAAATCGATTGGGAAAAAGAAGAAATGACAAATTAA

ADSDINI■TGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTKEYMSTLTYGFNGNLTGDD
TSKIGGLIGAQVSLGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 11

SEQ ID NOs: 11 and 12-α-hemolysin M113K-RL2

ATGGCAGATTCTGATATTAATATTGCAACCGGTACTACAGATATTGGAAGCAATACTACAGTAA
AAACAGGTGATTTAGTCACTTATGATAAAGAAAATGGCATGCACAAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCGCGGAATTC
GATTGATACAAAAGAGTATAAGAGTACGTTAACGTACGGATTCAACGGTAACCTTACTGGTGAT
GATACTAGTAAAATTGGAGGCCTTATTGGGGCCCAGGTTTCCCTAGGTCATACACTTAAGTATG
TTCAACCTGATTTCAAAACAATTCTCGAGAGCCCAACTGATAAAAAAGTAGGCTGGAAAGTGAT
ATTTAACAATATGGTGAATCAAATTGGGGACCATACGATCGAGATTCTTGGAACCCGGTATAT
GGCAATCAACTTTTCATGAAAACTAGAAATGGTTCTATGAAAGCAGCAGATAACTTCCTTGATC
CTAACAAAGCAAGTTCTCTATTATCTTCAGGGTTTTCACCAGACTTCGCTACAGTTATTACTAT
GGATAGAAAAGCATCCAAACAACAAACAAATATAGATGTAATATACGAACGAGTTCGTGATGAT
TACCAATTGCATTGGACTTCAACAAATTGGAAAGGTACCAATACTAAAGATAAATGGACAGATC
GTTCTTCAGAAAGATATAAAATCGATTGGGAAAAAGAAGAAATGACAAATTAA

ADSDINIATGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTKEY■STLTYGFNGNLTGDD
TSKIGGLIGAQVSLGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 12

SEQ ID NOs: 13 and 14-α-hemolysin M113R-RL2

ATGGCAGATTCTGATATTAATATTGCAACCGGTACTACAGATATTGGAAGCAATACTACAGTAA
AAACAGGTGATTTAGTCACTTATGATAAAGAAAATGGCATGCACAAAAAAGTATTTTATAGTTT
TATCGATGATAAAAATCACAATAAAAAACTGCTAGTTATTAGAACAAAAGGTACCATTGCTGGT
CAATATAGAGTTTATAGCGAAGAAGGTGCTAACAAAAGTGGTTTAGCCTGGCCTTCAGCCTTTA
AGGTACAGTTGCAACTACCTGATAATGAAGTAGCTCAAATATCTGATTACTATCCGCGGAATTC
GATTGATACAAAAGAGTATAGAAGTACGTTAACGTACGGATTCAACGGTAACCTTACTGGTGAT
GATACTAGTAAAATTGGAGGCCTTATTGGGGCCCAGGTTTCCCTAGGTCATACACTTAAGTATG
TTCAACCTGATTTCAAAACAATTCTCGAGAGCCCAACTGATAAAAAAGTAGGCTGGAAAGTGAT
ATTTAACAATATGGTGAATCAAATTGGGGACCATACGATCGAGATTCTTGGAACCCGGTATAT
GGCAATCAACTTTTCATGAAAACTAGAAATGGTTCTATGAAAGCAGCAGATAACTTCCTTGATC
CTAACAAAGCAAGTTCTCTATTATCTTCAGGGTTTTCACCAGACTTCGCTACAGTTATTACTAT
GGATAGAAAAGCATCCAAACAACAAACAAATATAGATGTAATATACGAACGAGTTCGTGATGAT
TACCAATTGCATTGGACTTCAACAAATTGGAAAGGTACCAATACTAAAGATAAATGGACAGATC
GTTCTTCAGAAAGATATAAAATCGATTGGGAAAAAGAAGAAATGACAAATTAA

ADSDINIATGTTDIGSNTTVKTGDLVTYDKENGMHKKVFYSFIDDKNHNKKLLVIRTKGTIAGQ
YRVYSEEGANKSGLAWPSAFKVQLQLPDNEVAQISDYYPRNSIDTKEYSTLTYGFNGNLTGDD
TSKIGGLIGAQVSLGHTLKYVQPDFKTILESPTDKKVGWKVIFNNMVNQNWGPYDRDSWNPVYG
NQLFMKTRNGSMKAADNFLDPNKASSLLSSGFSPDFATVITMDRKASKQQTNIDVIYERVRDDY
QLHWTSTNWKGTNTKDKWTDRSSERYKIDWEKEEMTN

TABLE 13

SEQ ID NO: 15-DNA sequence used in the Example

TTCCCCCCCCCCCCCCCCCCCCTTAAAAAAAAAATTCCCCCC
CCCCTTAAAAAAAAAATTCCCCCCCCC

---

The invention claimed is:

1. A method of decreasing translocation speed of a nucleic acid strand through a transmembrane beta-barrel protein pore, comprising:
   (a) increasing the net positive charge of the barrel of the pore by (i) substituting one or more positively charged amino acids into the barrel of the pore or (ii) substituting one or more negatively charged amino acids into the barrel of the pore with one or more uncharged amino acids, non-polar amino acids or aromatic amino acids; and
   (b) passing the nucleic acid strand through the pore, wherein increasing the net positive charge decreases the translocation speed of the nucleic acid strand through the pore, and
   wherein said transmembrane beta-barrel protein pore is selected from the group consisting of β-toxin, α-hemolysin, leukocidin, and outer membrane porin F (OmpF).

2. A method according to claim 1, wherein increasing the net positive charge further:
   (a) increases the frequency of translocation of the nucleic acid strand through the pore;
   (b) decreases the threshold voltage for translocation of the nucleic acid strand through the pore; or
   (c) decreases the number of non-translocation interactions between the nucleic acid strand and the pore.

3. A method according to claim 1, wherein the pore is α-hemolysin, or a variant thereof, and comprises:
   (a) seven subunits each comprising SEQ ID NO: 2 or a variant thereof that is at least 95% homologous to the entire length of the amino acid sequence of SEQ ID NO: 2 based on amino acid identity and retains pore forming activity; or
   (b) seven subunits each comprising SEQ ID NO: 4 or a variant thereof that is at least 95% homologous to the entire length of the amino acid sequence of SEQ ID NO: 4 based on amino acid identity and retains pore forming activity.

4. A method according to claim 1, wherein the one or more positively-charge amino acids are histidine (H), lysine (K) and/or arginine (R).

* * * * *